(12) United States Patent
Yamakawa et al.

(10) Patent No.: US 9,408,579 B2
(45) Date of Patent: Aug. 9, 2016

(54) RADIATION IMAGING APPARATUS AND PHANTOM USED FOR THE SAME

(75) Inventors: Tsutomu Yamakawa, Osaka (JP); Koichi Ogawa, Tokyo (JP); Akitoshi Katsumata, Ichinomiya (JP); Masahiro Tsujita, Osaka (JP); Hideyuki Nagaoka, Osaka (JP)

(73) Assignee: TAKARA TELESYSTEMS CORP., Osaka-Shi, Osaka (JP)

( * ) Notice: Subject to any disclaimer, the term of this patent is extended or adjusted under 35 U.S.C. 154(b) by 461 days.

(21) Appl. No.: 13/696,710

(22) PCT Filed: May 10, 2011

(86) PCT No.: PCT/JP2011/060731
§ 371 (c)(1),
(2), (4) Date: Jan. 21, 2013

(87) PCT Pub. No.: WO2011/142343
PCT Pub. Date: Nov. 17, 2011

(65) Prior Publication Data
US 2013/0114799 A1   May 9, 2013

(30) Foreign Application Priority Data

May 11, 2010   (JP) .................................. 2010-109144

(51) Int. Cl.
*A61B 6/14*   (2006.01)
*A61B 6/02*   (2006.01)
(Continued)

(52) U.S. Cl.
CPC . *A61B 6/14* (2013.01); *A61B 6/027* (2013.01); *A61B 6/583* (2013.01); *A61B 6/588* (2013.01); *G06T 11/006* (2013.01); *A61B 6/469* (2013.01); *A61B 6/547* (2013.01); *G06T 2211/436* (2013.01)

(58) Field of Classification Search
CPC ...... A61B 6/032; A61B 6/583; A61B 6/4035; A61B 6/482; A61B 6/14; A61B 6/588; A61B 6/025; G01N 23/046

USPC ....................... 378/19, 38; 382/128, 131, 132
See application file for complete search history.

(56) References Cited

U.S. PATENT DOCUMENTS

| 2004/0252811 A1* | 12/2004 | Morita et al. ................ 378/207 |
| 2006/0203959 A1 | 9/2006 | Spartiotis et al. |
| 2009/0310845 A1 | 12/2009 | Ogawa et al. |

FOREIGN PATENT DOCUMENTS

| JP | 1982-203430 | 12/1982 |
| JP | 3023633 U | 4/1996 |

(Continued)

OTHER PUBLICATIONS

International Search Report for PCT/JP2011/060731, ISA/JP, mailed Jun. 14, 2011.

(Continued)

*Primary Examiner* — Glen Kao
*Assistant Examiner* — Chih-Cheng Kao
(74) *Attorney, Agent, or Firm* — Harness, Dickey & Pierce, P.L.C.

(57) ABSTRACT

In the imaging space provided by a panoramic imaging apparatus, a phantom is arranged. The phantom is located to a predetermined tomographic plane and includes markers which image known positional information with an X-ray beam. The X-ray beam from an X-ray source is acquired as X-ray transmission data by a detector, and a panoramic image is produced using the data. Based on known positional information of the markers and information of marker positions in the panoramic image, distance information (Rs, Rd) between the X-ray tube and the detector and height information (B1) of the X-ray tube to the detector are calculated. From this calculated results and the acquired data, parameters ($\Delta x/\Delta Fi$, $\theta$, $\Delta\theta/\Delta Fi$, D, A, CX, CY) defining positional relationships among the X-ray tube, the detector, and the tomographic plane are calculated such that amounts of changes in the position connecting the X-ray tube and the detector are considered in the parameters. This allows the parameters to be calibrated for 3D image reconstruction.

20 Claims, 37 Drawing Sheets

(51) Int. Cl.
  *G06T 11/00* (2006.01)
  *A61B 6/00* (2006.01)

(56) References Cited

FOREIGN PATENT DOCUMENTS

| JP | 2005-21675 A | | 1/2005 | |
|---|---|---|---|---|
| JP | EP 1961383 | * | 4/2007 | ............... A61B 6/14 |
| JP | 2007-136163 A | | 6/2007 | |
| JP | 2007-524438 | | 8/2007 | |
| WO | 2004/086972 | | 10/2004 | |

OTHER PUBLICATIONS

International Preliminary Report on Patentability for PCT/JP2011/060731, IB, Geneva, issued Dec. 10, 2012, incorporating the English Translation of the Written Opinion of the ISA, ISA/JP, mailed Jun. 14, 2011.

* cited by examiner (FOR REFERENTIAL-PLANE POSITION)

(FOR OUTER-PLANE POSITION)

FIG.11
(A)
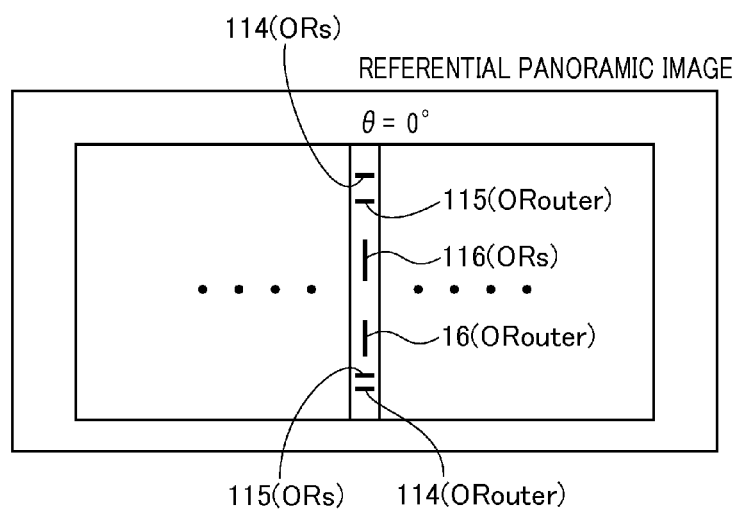
(B)
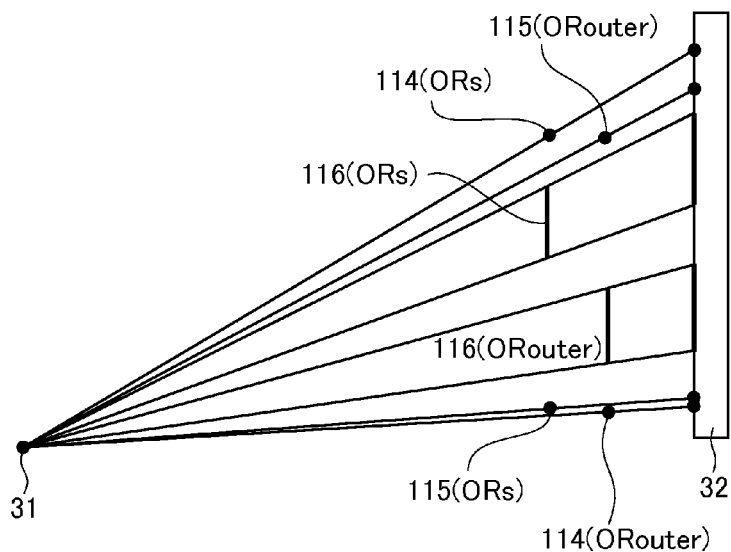

FIG.13
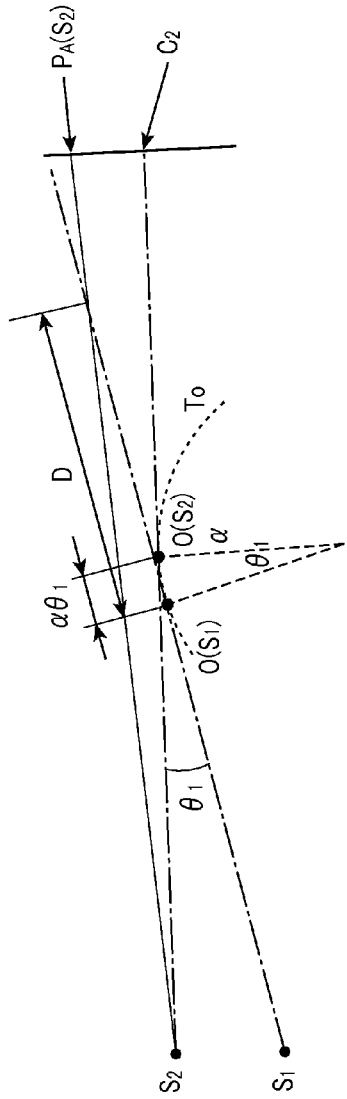
(A)
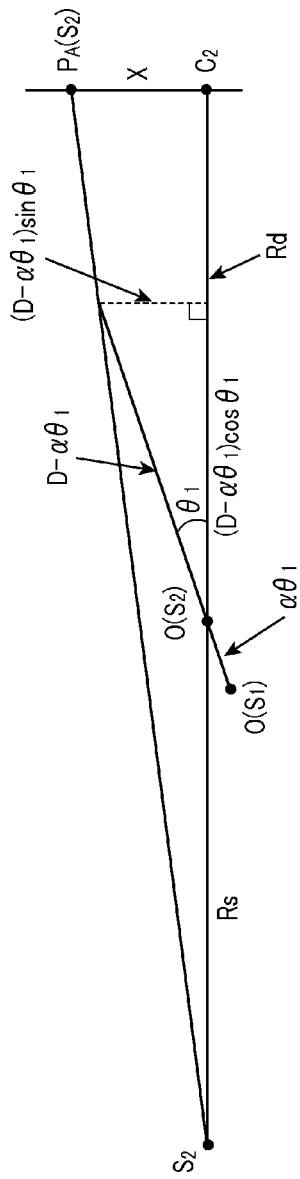
(B)

FIG.29(1)
(A)
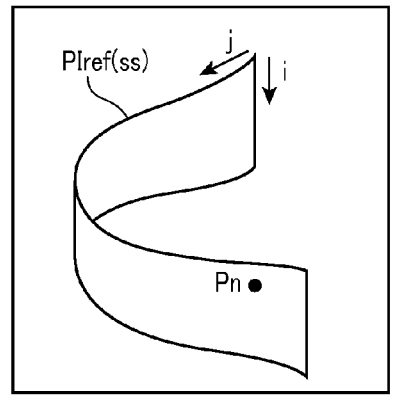
(B)
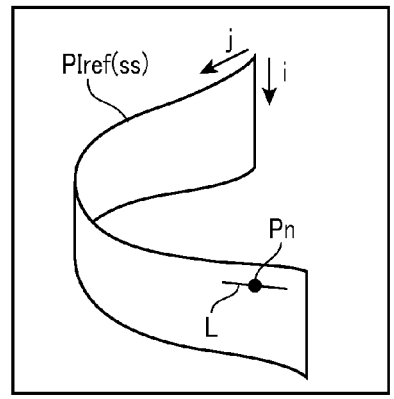
(C)
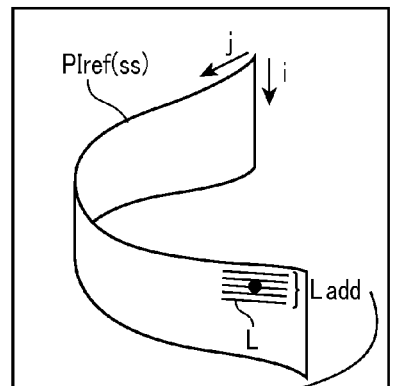
(D)
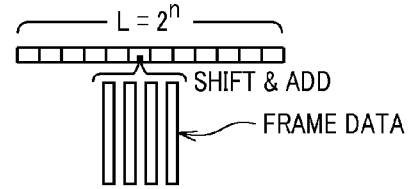

PLANE OF REFERENTIAL PANORAMIC IMAGE (PIst)

PROJECTION

SS

PIfocus

31

PIproj – 2D

ROI (FOR OUTER-PLANE POSITION)

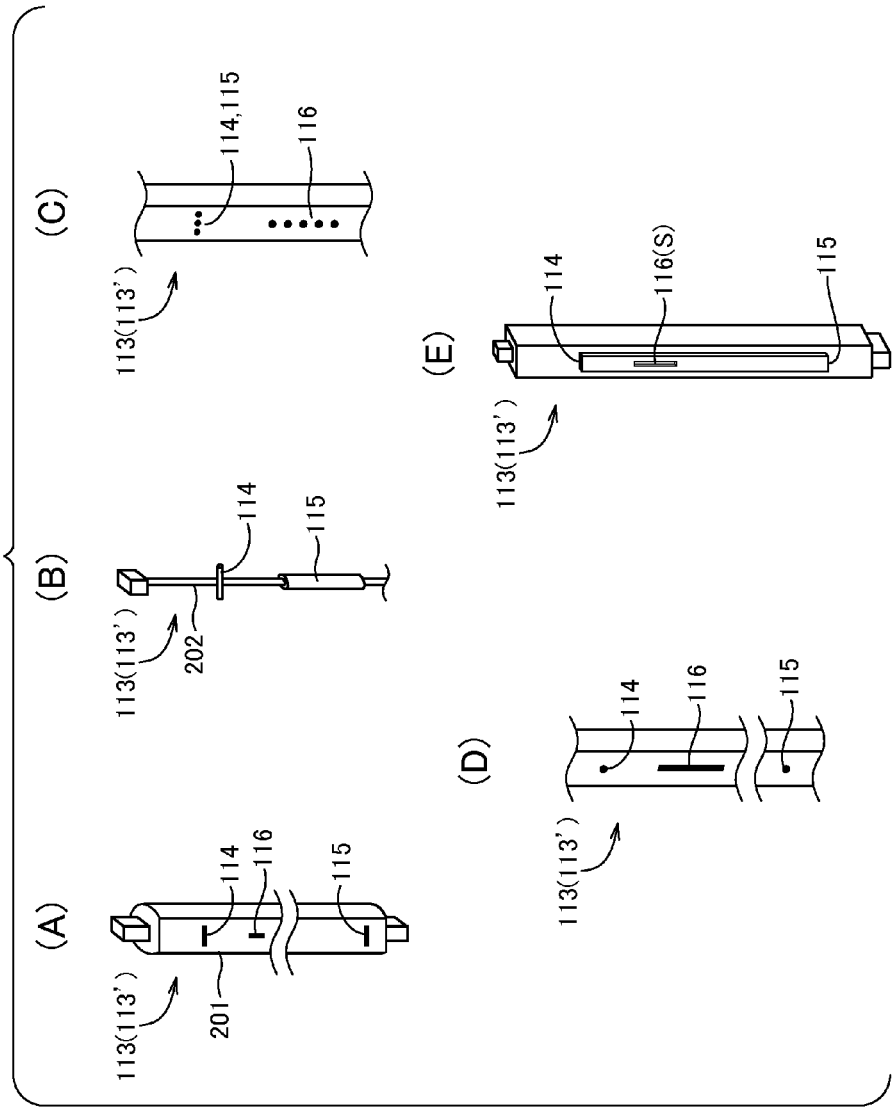

RADIATION IMAGING APPARATUS AND PHANTOM USED FOR THE SAME

CROSS-REFERENCE TO RELATED APPLICATIONS

This application is a 371 U.S. National Stage of International Application No. PCT/JP2011/060731, filed May 10, 2011. This application claims priority to Japanese Patent Application No. 2010-109144, filed May 11, 2010. The disclosures of the above applications are incorporated herein by reference.

FIELD OF THE INVENTION

The present invention relates to a radiation imaging apparatus that images an object using radiation and a phantom used in the apparatus, and in particular, to a radiation imaging apparatus that produces images such as panoramic images of an object according to a tomosynthesis technique and the phantom used by the apparatus for calibration thereof and a structural analysis of the imaging space provided by the apparatus.

BACKGROUND ART

In recent years, tomographic imaging using a tomosynthesis technique has been used actively. The theory of this tomosynthesis technique has been known long before (for example, refer to patent document 1), and recently, tomographic imaging that enjoys ease of image reconstruction performed using the tomosynthesis technique has been proposed (for example, refer to patent documents 2 and 3). Especially, many such cases can be found in dental and mammographic fields (for example, refer to patent documents 4, 5 and 6).

Conventionally, as one of radiation imaging apparatuses that employ the tomosynthesis technique by choice, there is a dental panoramic imaging apparatus. In this panoramic imaging apparatus, since an X-ray detector (hereinafter, referred to as a detector) has a limitation in its movement, the apparatus is designed to focus on a tomographic plane (which is referred to as a referential tomographic plane) according to a trajectory which is set mechanically in an imaging space. The imaging space refers to a space in which there is an X-ray path connecting the X-ray tube and the detector which are rotated around the jaw of a patient.

Therefore, the focuses of produced images are optimized best only when the tooth row exists at and along the referential tomographic plane in the imaging space. However, when the tooth row is out of alignment from the referential tomographic plane, images are produced with poor focusing, so that the images blur. From this point of view, when it is desired to observe blurred portions of produced images at higher resolution, positioning of the patient is performed again to focus the blurred portions more clearly and data are acquired again, or, the blurred portions are subjected to intraoral imaging to obtain clearer images.

Meanwhile, in recent years, an X-ray panoramic imaging apparatus described in patent document 7 has been developed, in which a detector capable of acquiring X-ray detection data at a faster speed (for example, 300 FPS) is used and all the detection data are inputted into a computer to apply the tomosynthesis technique to the detection data. In this apparatus, the detection data are processed based on the tomosynthesis technique to produce panoramic images of tomographic planes. In this apparatus, the position of a tomographic plane can be changed in the front-back direction of the plane and a panoramic image of the changed tomographic plane can be produced. For this image production, information indicative of distances of plural tomographic planes which are spatially parallel to the detection surface of the detection (such information is called as shift & add quantities or gains) is obtained by using a phantom or by theoretical calculation. For imaging, a pair of the X-ray tube and the detector is rotated around the patient's jaw, during which data are acquired. The central position of this rotation approaches to the tooth row and departs from it during the imaging. The acquired data are then subjected to software processing based on the tomosynthesis technique that uses the foregoing distance information, which provides images with less blur.

PRIOR ART REFERENCE

Patent Reference

[Patent Reference 1] JP-A-S57-203430
[Patent Reference 2] JP-A-H6-88790
[Patent Reference 3] JP-A-H10-295680
[Patent Reference 4] JP-A-H4-144548
[Patent Reference 5] JP-A-2008-110098
[Patent Reference 6] US2006/0203959 A1
[Patent Reference 7] JP-A-2007-136163

DISCLOSURE OF THE INVENTION

Issues to be Solved by the Invention

In the panoramic imaging apparatus described in the foregoing patent reference 7, it is assumed that plural tomographic images to be reconstructed exist at positions on lines each connecting the detector and the X-ray tube at each rotational angular position. Under this assumption, the tomosynthesis technique is used to produce panoramic images of respective tomographic planes. Thus, in cases where tomographic planes are changed from one to another, e.g. another tomographic plane is designated for producing its panoramic image, the enlargement factor of the image changes. Due to such changes, a produced image will be distorted in its longitudinal direction (the vertical direction of the tooth row). As images are digitized, it is possible to produce images with less distortion in their vertical and lateral directions provided that the tooth row is exactly positioned at and along the referential tomographic plane.

However, when this positioning condition is not met, distortion always occurs in images. Further, when a tooth row is not positioned along the referential tomographic plane, there will also be caused blur in the lateral direction of a reconstructed panoramic image. In such a case, it is possible to lessen the lateral distortion (blur) if imaging processing is able to provide focused images. However, in that case, due to the fact that the longitudinal distortion is not related to the shift & add quantities, there will be left longitudinal distortion in panoramic images. If there is distortion in an image, a distance between two points in an image cannot be depicted accurately compared with the actual distance. Obviously, there are various inconveniences, such as, being unable to accurately measure a distance between two points, which result in panoramic images which provide poor measurement capabilities.

The reason why the foregoing longitudinal distortion occurs is as follows. During the data acquisition, the X-ray tube and the detector rotate around a patient's tooth row while they are directly opposed to each other at mutually different radiuses. During the rotation, a relative rotation angle of the pair of the X-ray tube and the detector to the tooth row, that is, a radiation angle of X-ray flux radiated from the X-ray tube to the detector, is changed continuously for X-ray scanning. As the rotation angle is changed during the X-ray scanning, the center of rotation of each of the X-ray tube and the detector (i.e., the rotation center: the X-ray tube and the detector both rotate around the rotation center with this rotation center used in common by the X-ray tube and the detector) positionally approaches to and departs from the tooth row. Positional changes of this rotation center will cause the enlargement factor in the longitudinal direction of the tooth row to change position by position in a tooth row direction, which results in longitudinal distortion of panoramic images.

Of course, when tomographic planes are changed from one to another, distortion is unavoidably caused in a panoramic image. From this point of view, panoramic images produced by the panoramic imaging apparatus described by the patent reference 7 are not proper for quantitative measurement. It is also difficult to check time-series changes in subjects depicted in images by using techniques such as a subtraction technique. Clinical applications of the foregoing panoramic imaging apparatus are limited. For such reasons, conventional panoramic imaging apparatuses cannot be used as a true alternative means for intraoral imaging, which is one of reasons that the conventional panoramic imaging apparatuses cannot be superior to dental CT scanners.

By the way, the panoramic imaging apparatus is produced in different design specifications, of course, by different manufactures. Further, even when being manufactured by the same manufacture, each panoramic imaging apparatus has irregularities with regard to its mechanical operations. Especially, in a mechanism that rotates the X-ray tube and the detector, such irregularities influence panoramic images being reconstructed as errors in the images. Thus it is required to have information showing that various factors comply with initial design of each apparatus. Such factors, which are obtained by checking each apparatus, include a positional relationship between the X-ray tube and the detector, how the rotation center of the pair of the X-ray tube and the detector moves, movement speeds thereof, and X-ray radiation directions. To obtain such information means to three-dimensionally understand the structure of the imaging space (i.e., positional relationships to the referential tomographic plane). This information should be obtained by checking every apparatus and obtained information should be reflected into panoramic reconstruction processing. However, conventionally, there is provided no need for obtaining such information. Far from it, the conventional apparatus has no device and means for obtaining and reflecting such information.

The present invention has been made in consideration of the foregoing conditions, and it is an object to provide a radiation imaging apparatus and a phantom used in the apparatus, in which the apparatus is able to accurately check the structure of an imaging system for each radiation angle of radiation relative to a predetermined tomographic plane in the imaging space, that is, the three-dimensional structure of the imaging space through scanning using a phantom, and information indicative of the structure is used to provide images with less distortion and with actual positions of objects three-dimensionally reflected in an accurate manner.

A further object of the present invention is to provide a radiation imaging apparatus and a phantom used in the apparatus, in which the foregoing information about the structure is used to remove or lessen longitudinal distortion in images reconstructed according to the tomosynthesis technique for providing tomographic images in which positions of actual objects are three-dimensionally reflected in an accurate manner.

Means for Solving the Issues

In order to achieve the object, the present invention provides, as one mode, a radiation imaging apparatus including: a radiation source that radiates a radiation; a detector that is arranged to be opposed to the radiation source and that outputs, frame by frame, a frame of digital electric two-dimensional data corresponding to the radiation entering the detector; moving means for relatively moving the radiation source and the detector, the detector, or an object being imaged to a remaining element among the radiation source, the detector, and the object such that a line connecting the radiation source and the detector is positionally changed in an imaging space provided between the radiation source and the detector; and data acquiring means for acquiring, frame by frame, the data outputted from the detector while the radiation source and the detector, the detector, or the object is moved by the moving means, wherein the data acquired by the data acquiring means is used to be produced into a three-dimensional image of an imaging portion of the object, characterized in that the apparatus includes: a phantom arranged in the imaging space to be located at a predetermined tomographic plane in the imaging space and configured to have a marker with which known positional information in the imaging space is imaginable with the radiation; image producing means for producing an image from the data acquired by the data acquiring means in response to the radiation emitted from the radiation source in a state where the phantom is arranged in the imaging space; first calculating means for calculating, based on the known positional information of the marker and information indicative of a position of the marker which is obtained from the image, information indicative of a distance between the radiation source and the detector and information indicative of a height of the radiation source relative to the detector; and second calculating means for calculating, based on results calculated by the first calculation means and the data, a parameter defining a positional relationship among the radiation source, the detector, and the tomographic plane in the imaging space, the parameter taking into account changes in a position of the line.

In addition, to achieve the foregoing object, the present invention provides, as another mode, a phantom arranged between an X-ray source radiating an X-ray beam and a detector detecting an X-ray beam as digital electric signals, the X-ray source and the detector being provided in a panoramic imaging apparatus wherein the X-ray source and the detector are opposed to each other with an object positioned therebetween, the detector outputs the digital electric signals as frame data while the X-ray source and the detector are rotated around the object, and a panoramic image of a tomographic plane of the object is produced based on the frame data, characterized in that the phantom includes a base; a plurality of pillars planted, trajectory by trajectory, at positions on each of a reference-plane trajectory and a further trajectory which is set to be separated from the reference-plane trajectory but runs parallel with the reference-plane trajectory, the reference-plane trajectory being produced by a referential tomographic plane to the base, the referential tomographic plane being set as a tomographic plane in the imaging space, and markers arranged at each of the plurality of pillars and formed to be different in an X-ray transmittance from the pillars themselves.

Effects of the Invention

Accordingly, in the present invention, the structure of an imaging system for each radiation angle of a ration, that is, the three-dimensional structure of the imaging space, is checked accurately through scanning using a phantom. And information indicative of the structure is used provide images of less distortion and of highly accurate reflection of three-dimensional actual positions of objects being imaged.

BRIEF DESCRIPTION OF THE DRAWINGS

In the accompanying drawings:

FIG. 11 shows illustrations explaining positional relationships among the positions of markers imaged in the referential panoramic image, the detector, and the markers;

FIG. 13 shows illustrations explaining the geometrical positional relationships shown in FIG. 13, in a numerical manner;

FIG. 29(2) is a view explaining, together with FIG. 29(1), the process to identify optimally-focused tomographic planes for each of positions on the 3D reference image;

FIG. 45 is a further illustration showing a further modification of the phantom.

DETAILED DESCRIPTION OF PREFERRED EMBODIMENTS

With reference to the accompanying drawings, embodiments of the present invention will now be described.

With reference to FIGS. 1-43, an embodiment of a radiation imaging apparatus and a phantom used by the apparatus, which are according to the present invention, will now be described. In the present embodiment, the radiation imaging apparatus is employed as a dental X-ray panoramic imaging apparatus. The panoramic imaging apparatus will now be detailed.

Figure 1:
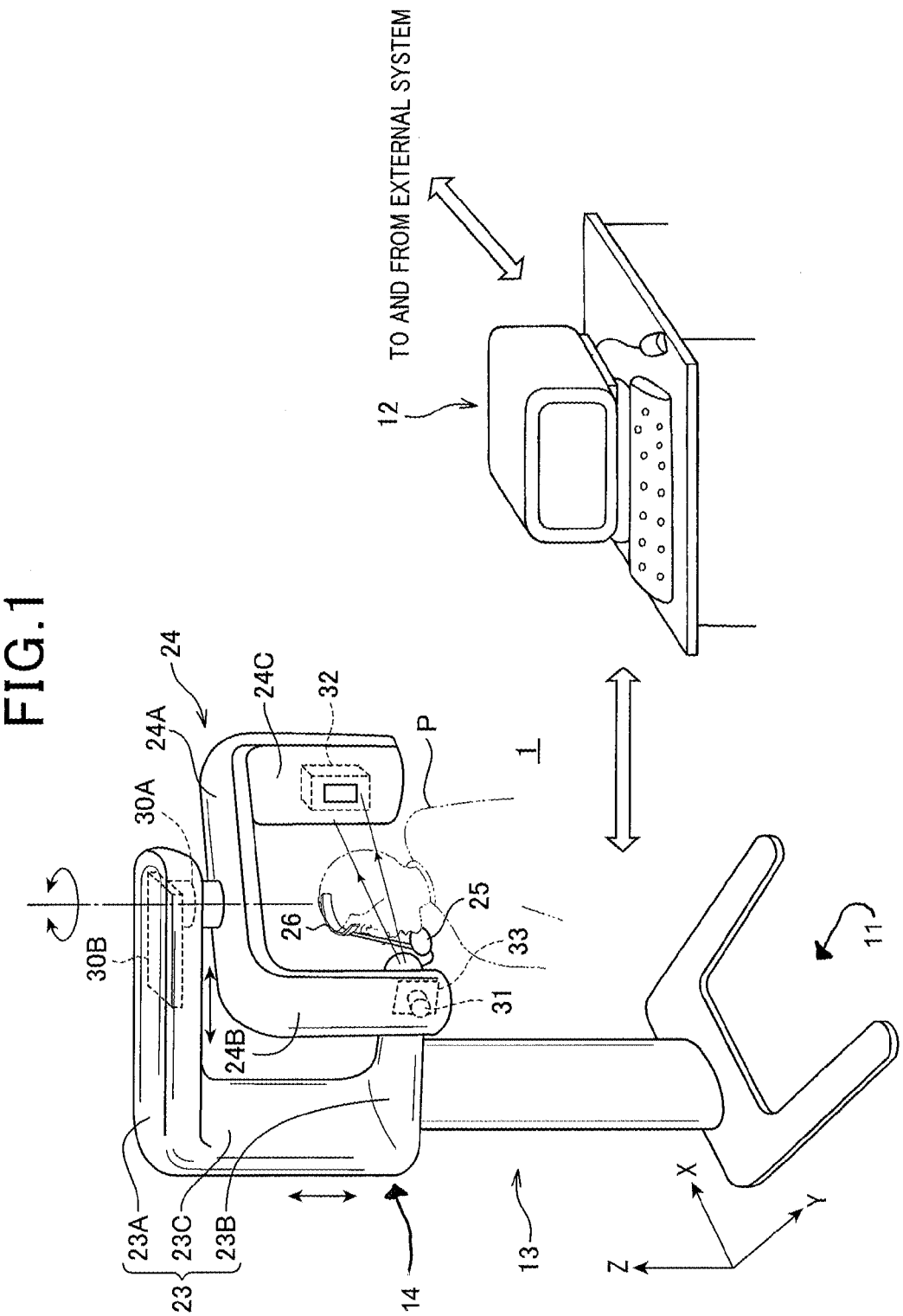
FIG. 1 is a perspective view outlining the whole configuration of an X-ray panoramic imaging apparatus employed as a radiation imaging apparatus according to one embodiment of the present invention.

FIG. 1 outlines the appearance of the panoramic imaging apparatus 1. This panoramic imaging apparatus 1 is able to scan, with an X-ray beam, the jaw of an object to obtain digital-quantity X-ray transmission data, and use the data to specify an actual three-dimensional real position (i.e., actually-existence position) of the tooth row and to produce (or reconstruct) panoramic images of the tooth row, whose irregularities (or differences) caused due to longitudinal enlargement factors are compensated based on a tomosynthesis technique.

The configuration of this panoramic imaging apparatus 1 will now be outlined. As shown in FIG. 1, this apparatus 1 is provided with a frame 11 with which data is acquired from an object (patient) P who is in a standing position, for example, and a control and calculation apparatus 12 realized by use of a computer. The control and calculation apparatus 12 is configured to control data acquisition performed by the frame 11, produce panoramic images based on the acquired data, and post-process the panoramic images in an interactive or manual manner with an operator (doctor or medical operator).

The frame 11 has a standing unit 13 and an imaging unit 14 movable upward and downward relative to the standing unit 13. The imaging unit 14 is attached to the pillar of the standing unit 13 to be movable upward and downward in a predetermined range.

For the sake of easier explanation, the panoramic imaging apparatus is given the XYZ orthogonal coordinate system whose Z-axis is assigned to the longitudinal direction, i.e., the vertical direction, of the standing unit 13. Incidentally, a two-dimensional panoramic image, described later, is represented with its abscissa axis defined as a j-axis and its ordinate axis defined as an i-axis (i.e., Z-axis).

The imaging unit 14 includes a vertical movement unit 23 whose side appearance is approximately C-shaped and a rotation unit 24 rotatably (turnably) supported by the vertical movement unit 23. The vertical movement unit 23 is movable in a given range of height in the Z-axis direction (longitudinal direction) by a not-shown vertical movement mechanism (for example, a motor and a rack/pinion device) arranged in the standing unit 13. A command for this movement is provided from the control/l/calculation apparatus 12 to the vertical movement mechanism.

As described, the vertical movement unit 23 has a side appearance which is approximately C-shaped, and an upper arm 23A and a lower arm 23B located on the upper and lower sides respectively and a longitudinal arm 23C integrally connecting the upper and lower arms 23A and 23B. The longitudinal arm 23C is movably, in the vertical direction, supported on the foregoing standing unit 13. Inside the upper arm 23A, a rotary drive mechanism 30A (for example, an electric motor and a reduction gear) is arranged. The rotary drive mechanism 30A receives a command for rotary drive from the control/l/ calculation apparatus 12. This mechanism 30A has an output shaft, which is the rotation shaft of the electric motor, which is arranged to protrude from the upper arm 23A downward (downward in the Z-axis direction). To this rotation shaft, the rotation unit 24 is rotatably coupled. That is, the rotation unit 24 is arranged downward from the vertical movement unit 23, and rotates responsively to the drive of the rotary drive mechanism 30A.

The rotary drive mechanism 30A is linked with a movement mechanism 30B. This movement mechanism 30B is composed of devices such as a not-shown electric motor and gears. This mechanism 30B is also driven responsively to a command for rotary drive from the control & calculation apparatus 12, and is capable of moving the rotary drive mechanism 30A, i.e., the rotation unit 24 along the X-Y plane. Hence, the rotation center of a pair of an X-ray tube and a detector, which will be described later, can be moved to two-dimensionally follow a later-described trajectory which is along a given path in a predetermined range of the X-Y plane.

Meanwhile, the lower arm 23B has an end on which a chin rest 25 is formed. A head rest 26 is detachably attached to the chin rest 25. An object P, i.e., patient, bites the bite block (simply a bite) such that the chin is placed on the chin rest 25 and the forehead is pushed to the head rest. This allows the oral portion of the object P to be fixedly positioned in a later-described imaging space.

The rotation unit 24 has also an approximately C-shaped appearance when being viewed from one side thereof in its used state, where the rotation unit is rotatably attached to the motor output shaft of the upper arm 23A, with its opened end side directed downward. Practically, the rotation unit has a lateral arm 24A rotatable (turnable) parallel with the lateral direction, that is, the X-Y plane and right and left vertical arms (the first and second vertical arms) extending downward (in the Z-axis direction) from both ends of the lateral arm 24A. The rotation unit 24 is also driven to operate under the control of the control & calculation apparatus 12.

At an inner lower end of the first vertical arm 24B, an X-ray tube 31 is provided which functions as a radiation emitting source. This X-ray tube 31 is for example a rotating anode X-ray tube and has a target (anode) which radially emits X-rays toward the second vertical arm 24C. The focus of an electron beam made to collide with the target is as small in radius as 0.5 mm (to 1 mm), that is, the X-ray tube 31 has a punctuate X-ray source. At a predetermined position on the front side of the X-ray tube 31, there is provided a collimator 33 having a slit. This collimator 33 is able to collimate the X-ray to fit with its detection surface thereof (that is, an actual acquiring window (for example, a window whose width is 5.0 mm), before the X-ray is made to enter the detector.

In contrast, at an inner lower end of the second vertical arm 24C, there is provided, as a radiation detecting means, a digital type of X-ray detector 32 equipped with X-ray detection elements two-dimensionally arrayed (for example, arrayed in a matrix of 64×1500) and produced to detect the incident X-rays through the incidence window. By way of example, this detector 32 has a longitudinally-long shaped detecting portion (for example, 6.4 mm width×150 mm long) which is made of CdTe. In the present embodiment, since the tomosynthesis technique is adopted, it is indispensable to provide the detector 32 with a plurality of X-ray detecting elements in its lateral (width) direction.

The detector 32 is arranged such that its longitudinal direction agrees with the Z-axis direction. The detector 32 has a lateral effective width which is set to, for example, approximately 5.0 mm by the foregoing collimator 33. This detector 32 is capable of acquiring digital-quantity image data in accordance with amounts of incident X-rays at a frame rate of, for example, 300 fps (for example, 64×1500 pixels per frame). The acquired data are called "frame data."

During imaging, the X-ray tube 31 and the detector 32 are located to be opposed directly or obliquely to each other with the oral cavity of the object P therebetween, and driven to rotate together around the oral cavity. "The X-ray tube 31 and the detector 32 are directly opposed to each other" refers to a state where the center axis of an X-ray beam emitted from the X-ray tube 31 (i.e., the center axis formed when the X-ray beam is projected to the XY plane) is orthogonal to the detection surface of the detector 32. Further, "the X-ray tube 31 and the detector 32 are obliquely opposed to each other" refers to a state where the X-ray beam enters the detection surface of the detector 32 such that the center axis of the X-ray beam produces an angle other than 90 degrees (0 degrees<angle<90 degrees) to the detector surface. Therefore, the X-ray tube 31 and the detector 32 can be rotated (moved) in a variety of modes necessary for scanning based on the tomosynthesis technique.

Figure 2:
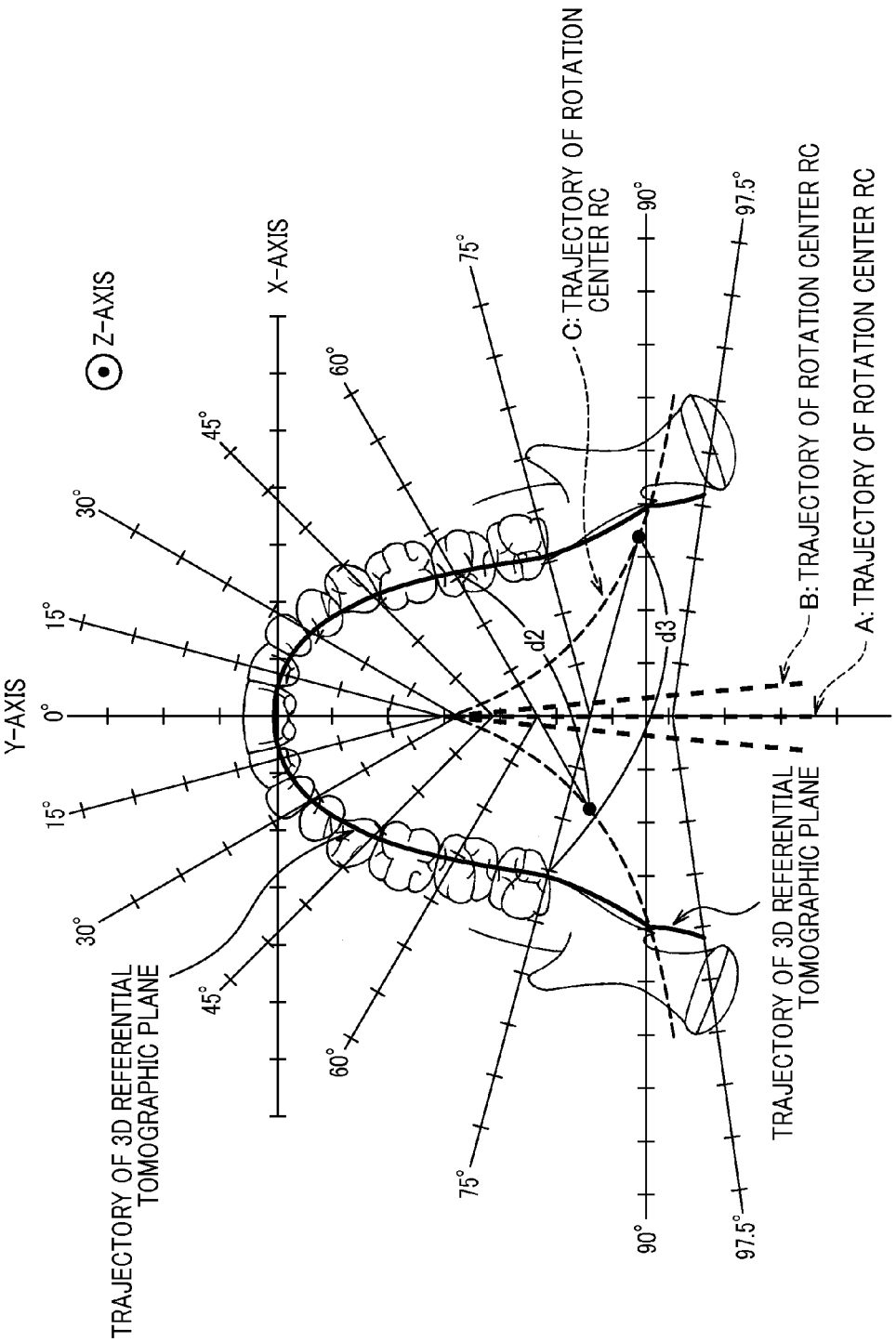
FIG. 2 is a view explaining the tooth row of an object being examined by the panoramic imaging apparatus according to the embodiment, a 3D referential tomographic plane which is set at the tooth row, and a trajectory of a rotation center on which a pair of an X-ray tube and a detector rotates.

However, in the present embodiment, the X-ray tube 31 and the detector 32 are always located to be opposed directly to each other with the oral cavity of the object P therebetween, and, as the paired devices, are driven to rotate together around the oral cavity. However, this rotation is not a rotation to draw a simple circle. That is, in the present embodiment, the pair of the X-ray tube 31 and the detector 32 is driven to rotate around a rotation center RC which is moved (refer to FIGS. 2 and 3). Though described later, a distance from the rotation center RC to each of the X-ray tube 31 and the detector 32 is set with consideration of a longitudinal enlargement factor. As shown in FIG. 2, the rotation center RC is set to draw either a trajectory A which goes and returns approximately linearly from back teeth to anterior teeth in the tooth row or a slightly-angled triangular trajectory B which also goes linearly from back teeth to anterior teeth in the tooth row, but returns at an acute angle and goes back linearly. Hence, the X-ray tube 31 and the detector 32 are rotated with their angular speed curves changed properly in a controlled manner.

The trajectory for the rotation center RC may be a chevron-shaped trajectory C which goes from one of both-side molars portions to anterior teeth to draw a curved path and returns to the opposite-side molars to also draw a curved path. This trajectory C is, in particular, previously designed to enable the X-ray beam to focus on a tomographic plane along a standard shape and size tooth row (hereinafter referred to as a 3D referential tomographic plane) and to follow the 3D referential tomographic plane based on mechanical motions of the paired devices. During the follow of the X-ray focus along the 3D referential tomographic plane SS, the X-ray tube 31 and the detector 32 are rotated with their angular speed curves changed properly.

In this way, the X-ray scanning is performed by rotating the X-ray tube 31 and the detector 32, so that the rotations thereof provides an imaging space defined as an inner space surround by the orbits of the rotations of both the X-ray tube 31 and the detector 32.

Figure 3:
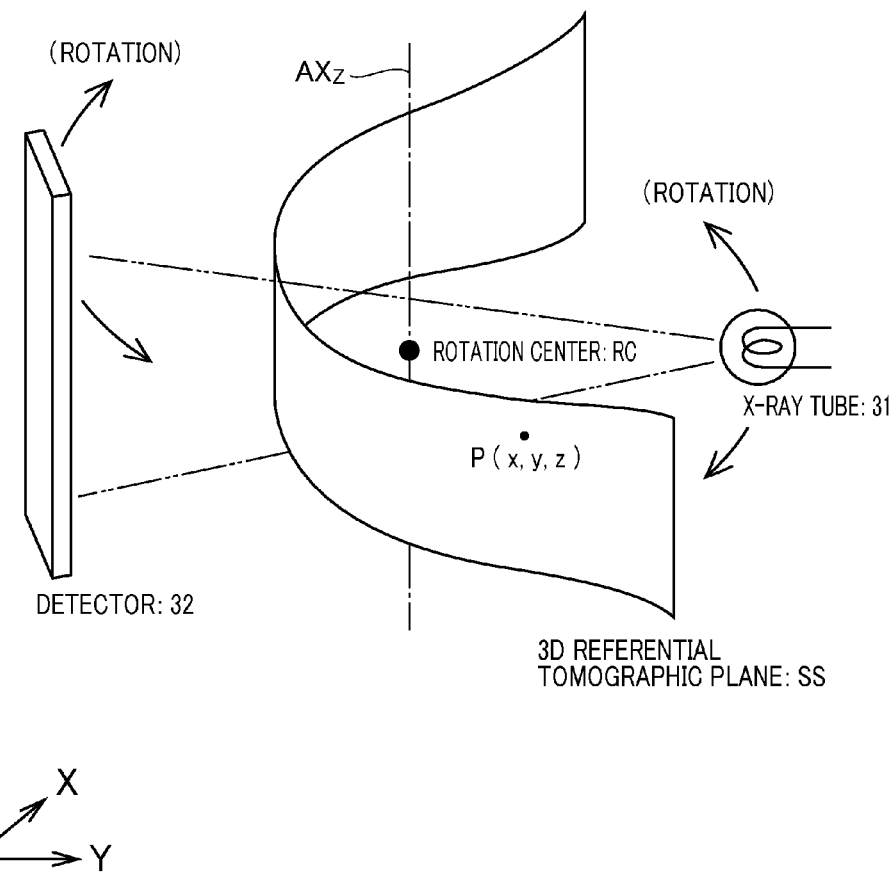
FIG. 3 is a perspective view explaining the geometrical relationship of the X-ray tube, the 3D referential tomographic plane, and the detector in the panoramic imaging apparatus.
Figure 6:
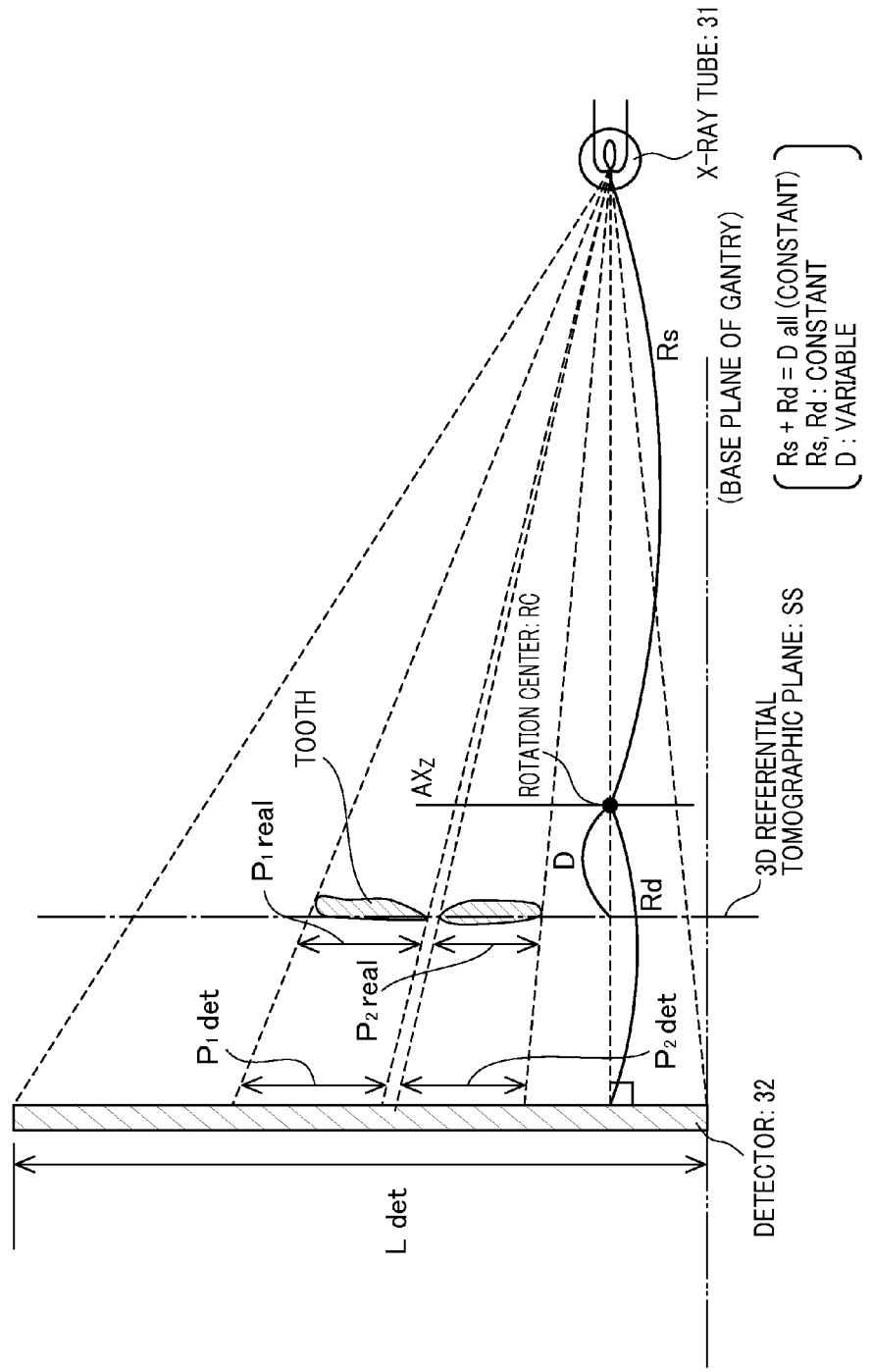
FIG. 6 is a view explaining a positional relationship among the X-ray tube, the 3D referential tomographic plane, the rotation center, and the detector.

The 3D referential tomographic plane presents an approximately horseshoe-shaped trajectory, which is projected on the XY plane, i.e., when being viewed in the Z-axis direction, as described, and an example of such a trajectory is shown in FIG. 2. The trajectory of this 3D referential tomographic plane SS is also known from, for example, a paper "R. Molteni, "A universal test phantom for dental panoramic radiography" MedicaMudi, vol. 36, no. 3, 1991." A geometrical relationship among the X-ray tube 31, the 3D referential tomographic plane SS, the detector 32, and a rotation axis AXz passing through the rotation center(s) RC is shown in FIG. 3. It should be noted that the rotation center RC positionally changes in accordance with the X-ray radiation angles, as shown by the dotted lines A, B and C in FIG. 2. The 3D referential tomographic plane SS is parallel with the incidence window of the detector 32 (i.e., the X-ray detection surface Ldet, as shown in FIG. 6), is a curved section standing along the Z-axis direction, and is set as a strip-like rectangular section when being developed two-dimensionally.

Figure 4:
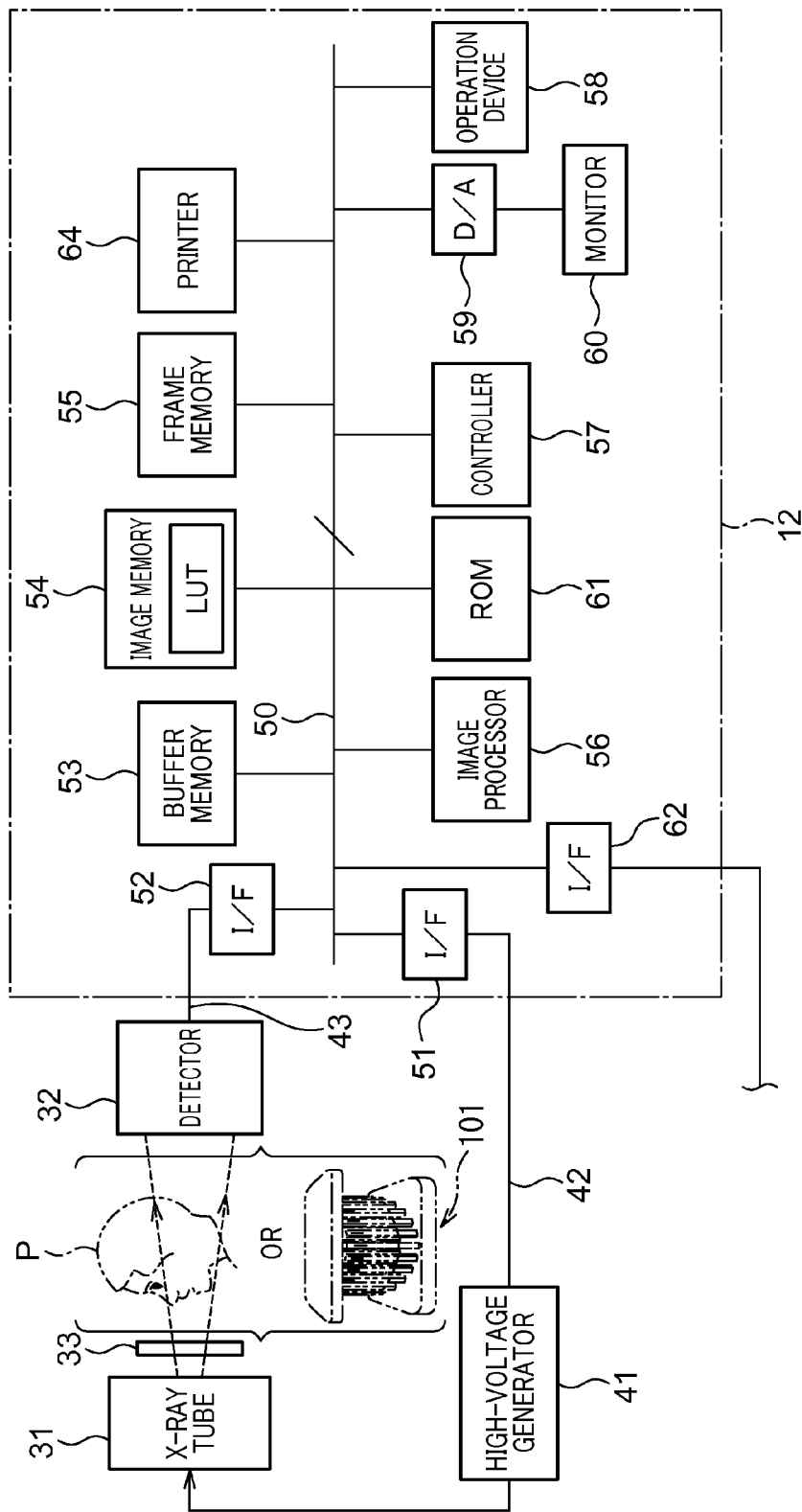
FIG. 4 is a block diagram outlining the electric configuration of the panoramic imaging apparatus.

FIG. 4 shows an electric block form for control and processing performed by this panoramic imaging apparatus. As shown in the figure, the X-ray tube 31 is connected to the control & calculation apparatus 12 via a high-voltage generator 41 and a communication line 42. The detector 32 is connected to the control & calculation apparatus 12 via a communication line 43. The high-voltage generator 41 is arranged at the standing unit 13, the vertical movement unit 23, or the rotation unit 24 and responds to a control signal from the control & calculation apparatus 12 to be controlled according to X-ray radiation conditions such as a tube current and a tube voltage to the X-ray tube 31 and a timing sequence for the radiation.

The control & calculation apparatus 12 is required to process large amounts of image data, and is composed of for example a personal computer which is capable of storing large amounts of image data. The control & calculation apparatus 12 includes, as its essential components, interfaces 51, 52 and 62, a buffer memory 53, an image memory 54, a frame memory 55, an image processor 56, a controller (CPU) 57, and a D/A converter 59, which are mutually communicably connected via an internal bas 50. The controller 57 is communicably connected to an operation device 58, and the D/A converter 59 is also connected to a monitor 60.

Of the above components, the interfaces 51 and 52 are connected to the high-voltage generator 41 and the detector 32 respectively, and responsible for conducting communication on control information and acquired data transmitted from/to the controller 57 to/from the high-voltage generator 41 and detector 32. The other interface 62 connects the internal bas 50 and the communication line, which allows the controller 57 to be communicable with an external apparatus. It is therefore possible for the controller 57 to take in oral images acquired by an external oral X-ray imaging apparatus and outputs panoramic images acquired by the present apparatus, to an external server based on for example the DICOM (Digital Imaging and Communications in Medicine) protocol.

The buffer memory 53 temporarily stores digital-quantity frame data received from the detector 32 via the interface 52.

The image processor 56, which is under the control of the controller 57, has functions of structurally analyzing the imaging space, performing processing for a calibration, producing panoramic images of the 3D referential tomographic plane, and performing processing for post-use of the panoramic images in an interactive manner with an operator. Programs for realizing such functions are stored in the ROM 61 in advance. Hence, the ROM 61 serves as a recording medium in which programs according to the present invention are stored. While such programs can be stored in the ROM 61 in advance as stated above, they can be installed into recording mediums such as a not-shown RAM, via a communication line or a portable memory from an external system in some cases.

In the present embodiment, the 3D referential tomographic plane is prepared previously by the apparatus. Alternatively, the 3D referential tomographic plane may be provided by selecting a desired one from plural tomographic planes prepared previously by the apparatus before performing imaging. In other words, the 3D referential tomographic plane is a fixed section in the imaging space, but the foregoing selection allows the plane to be movably positioned in a limited amount of range in the depth (back-and-forth) direction of a tooth row.

Frame data to be processed or now processed by the image processor 56, image data, and a look-up table (LUT) for calibration are stored in the image memory 54 in a readable and writable manner. The image memory 54 is composed of for example a large-capacity recording medium such as a hard disc (nonvolatile and readable and writable). The frame memory 55 is used to display image data such as panoramic image data reconstructed and panoramic imager data to be post-processed. The image data being stored in the frame memory 55 are read at intervals from the D/A converter 59 to be converted into corresponding analog signals, and displayed on the monitor 60.

The controller 57 controls the operations of all the components of the apparatus based on programs for control and processing, which are previously stored in the ROM 61. The programs are set such that the controller receives interactively information showing operator's operations for respective control items. Hence, the controller 57 is able to command acquisition (scanning) of frame data or other operations, as will be described later.

As shown in FIG. 1, a patient poses a standing position or a seated position with his or her chin seated on the chin rest 25, his or her mouth biting the bite block 26, and his or her head touched to a head rest 28. This allows the patient's head (jaw) to be fixedly positioned in an approximately central part in the space in which the rotation unit 24 rotates. With this patient's fixed posture, under the control of the controller 57, the rotation unit 24 rotates around the patient's jaw portion along the XY plane.

Instead of positioning realized by biting the bite block, another positioning method is provided where a patient bites a soft mouthpiece such as cotton and is fixed using year positioners, and then a mirror placed in front of the patient is used to confirm that the rotation will be straight to the tooth row.

During the rotation, under the control of the controller 57, the high-voltage generator 41 supplies to the X-ray tube 31 a pulse-mode high voltage (designated tube voltage and tube current) at intervals, whereby the X-ray tube 31 is driven on the pulse mode. This allows the X-ray tube 31 to radiate pulsed X-rays at intervals. In this pulse drive, a drive signal produces with half-wave rectification can be used or a drive signal produced with DC drive involving with an inverter circuit can be used. The X-rays transmit through the patient's jaw (including the tooth row portion) positioned at the designated imaging position) and enters the detector 32. Responsively to this, the detector 32 detects the incident X-rays at a very fast frame rate (for example 300 fps) as described, and outputs in sequence, frame by frame, corresponding electric-quantity two-dimensional frame data (for example 64×1500 pixels). The outputted frame data are transmitted to the buffer memory 53 via the communication line 43 and the interface 52 in the control & calculation apparatus 12 for temporal storage therein. The frame data in the buffer memory are then transferred to the image memory 53 for storage therein.

Hence, the image processor 56 is configured to reconstruct (produce), as a panoramic image (a referential panoramic image), a tomographic image, which is a section image, which focuses on the 3D referential tomographic plane SS using the frame data stored in the image memory 53. That is, this referential panoramic image is defined as "a panoramic image obtained under an assumption that a tooth row is present at and along the 3D referential tomographic plane SS." In addition, the image processor 56 uses this referential panoramic image to produce a three-dimensional (3D) referential image and a three dimensional (3D) autofocus image. This processing is outlined in FIG. 5. The 3D referential image is defined as "a three-dimensional image obtained under an assumption that a tooth row is present at and long the 3D referential tomographic plane SS." The 3D autofocus image is defined as "a surface image automatically optimally focusing on the tooth row from the 3D referential image using frame data or data of the referential panoramic image. In other words, the 3D autofocus image is a surface image with less blur and optimally focused, where the real position and actual size of a tooth row is depicted with higher precision.

In particular, it can be said that the 3D autofocus image takes it consideration that 3D autofocus images of individual persons differ person by person in most cases. In practice, it is almost difficult to find that tooth rows of individual persons being imaged are at and along the 3D referential tomographic plane SS (refer to FIG. 6). The tooth rows may partially or entirely offset from the 3D referential tomographic plane SS or may be oblique to that plane. In light of this, the 3D autofocus image is produced by automatically and accurately identifying the actual three-dimensional spatial position and shape of the tooth row of each person being imaged and automatically extracting from the identified results the actual shape of the person's tooth row.

The X-rays emitted from the X-ray tube 31 (of which focus is regard to as being punctuate) are radiated through the collimator 33. The X-rays (i.e., the X-ray flux) are transmitted through the oral cavity of the patient P, and detected by the longitudinally long, but with a lateral width, detector 32 having a given length in the Z-axis direction. Hence, the radiated directions of the X-rays are oblique, as shown in FIGS. 3 and 6. Accordingly, there exists a ratio (referred to as "enlargement factor" in the present embodiment) between the actual size of the tooth and the size of an image produced by the shade of the tooth projected onto the X-ray incident surface $L_{det}$ of the detector 32, and this ratio changes depending on positions of the rotation center RC. The enlargement factor is provided in both longitudinal and lateral directions (that is, normally, in the longitudinal and lateral directions of each tooth). When taking an example about the longitudinal direction shown in FIG. 6, a ratio between a real height $P_{1real}$ and a height $P_{1det}$ projected on the detection surface $L_{det}$ changes depending on where the rotation center RC is located. The rotational orbit of the pair of the X-ray tube 31 and the detector 32 is previously set such that, as exemplified in FIG. 2, the position of the rotation center RC changes during a single series of scanning actions (i.e., a single series of data acquiring actions).

The reason for the orbit is follows. As shown in FIG. 6, a distance $D_s+R_d$ between the X-ray tube 31 and the detector 32 is kept unchanged, and distances $R_s$ and $R_d$ from the rotation center RC to the X-ray tube 31 and the detector 32 are also kept unchanged (in the present embodiment, $R_s>R_d$). Meanwhile, for scanning with focusing on the 3D referential tomographic plane SS, design is made such that, during the one-time scan (i.e., data acquisition), the positions of the rotation center RC change so as to depict, by way of example, as describe before, the acute triangular trajectory B (refer to FIG. 2) relative to the horseshoe-shaped curved tooth row.

Concretely, a distance D from the rotation center RC to the 3D referential tomographic plane SS and a distance $R_d$–D from the detector 32 to the 3D referential tomographic plane SS change depending on advancement of the scanning. Depending on these changes, the rotation center RC comes closer to and recedes from the tooth row, so that the X-ray tube 31 comes closer to and recedes from the tooth row as well. Since the X-ray tube 31 has an X-ray source which can be regarded as a punctate source, the size of a projection image onto the detection surface $L_{det}$ becomes bigger as the X-ray tube 31 comes closer to the tooth row even under a condition where the height of the tooth is the same. That is, the enlargement factor becomes larger in such a case. In the example shown in FIG. 2, compared with a case where the molar teeth (a back teeth portion) are scanned, scanning the anterior teeth allows the rotation center RC to come closer to the tooth row, providing the enlargement factor with larger amounts depending on how much closer to the tooth row. For example, in the case of FIG. 2, the distance d1 is given when one of the anterior teeth is scanned in an X-ray radiation direction of 0 degrees. Meanwhile, in the case of scanning some of the molar teeth, there are provided distances d2 and d3 in the X-ray radiation directions of 60 degrees and 75 degrees respectively, for example. In this example, there are provided relationships of d1<d2, d1<d3, and d2<d3. Although the trajectory of the rotation center RC shown in FIG. 2 is simply an example, it is always true that the rotation center RC comes closer to and then recedes from the tooth row when scanning is made to focus the 3D referential tomographic plane SS by the panoramic imaging apparatus.

In this way, as the enlargement factor changes depending on each position in the tooth row, it is not possible to accurately and quantitatively analyze structures and temporal changes of the oral cavity unless there are provided panoramic images in which influence of this enlargement factor is well corrected.

Moreover, it is rare that, entirely or partially, the tooth row of a patient is positioned along the 3D referential tomographic plane SS. Thus, if it is desired to remove the influence of the enlargement factor, it is necessary to consider how much a tooth row is shifted, part by part, from the 3D referential tomographic plane.

The conventional panoramic images are produced with no consideration of the issues due to changes in the foregoing enlargement factor and shifts of tooth rows from the 3D referential tomographic plane SS. Thus, it is very difficult to quantitatively analyze the structure from the conventional panoramic images. In this regard, it is desired to provide a panoramic imaging apparatus capable of identifying three-dimensional real positions of objects in higher accuracy even when tooth rows are different in shapes and/or positions of objects, and/or regardless of what part of the same tooth row is imaged.

With consideration this, the panoramic imaging apparatus according to the present embodiment has a feature that image distortion due to differences, for every position of the teeth, in the enlargement factor even when the same tooth row can be removed and it is possible to automatically and accurately identify a three-dimensional spatial real position (including a shape) of a patient's tooth row. Thus it is possible to provide three-dimensional panoramic images with higher identification accuracy of positions (shapes).

In the present embodiment, a tomosynthesis technique is used to obtain images of tomographic planes or sections of an object. Practically, a large number of frame data, i.e., sets of pixel data, acquired at intervals by are shifted depending on a mapping position in a two-dimensional panoramic image and mutually added (called shift & add). Hence, an "optimal focus" referred in the present embodiment means that "being best focused or being less defocused", which also means that a region being interested in an image is higher in resolution than other regions thereof or an entire image has a higher degree of resolution.

When a referential panoramic image is produced, data composing this image are stored in the image memory 54 and also displayed by the monitor 60 in an appreciate display mode. The display mode is decided by an operator's intention which is given through the operation device 58.

(Calibration of Parameters Defining the Imaging Space)

Prior to imaging, with reference to FIGS. 7-20, calibration for the imaging space which is performed using a phantom will now be explained. That is, the calibration is for estimating values and changes in the values of geometric parameters showing the three-dimensional structure of an imaging system to the referential tomographic plane in the imaging space. The results of this calibration are reflected in reconstructing images and, if need arises, used for structural analysis and design of the imaging space.

Processing for this calibration is performed by the controller 57 and the image processor 56 in a cooperative manner. Of course, a processor dedicated only to the calibration may be used. In the present embodiment, this calibration is characterized by use of a phantom that models a tooth row of patients P.

(Phantom)

Figure 7:
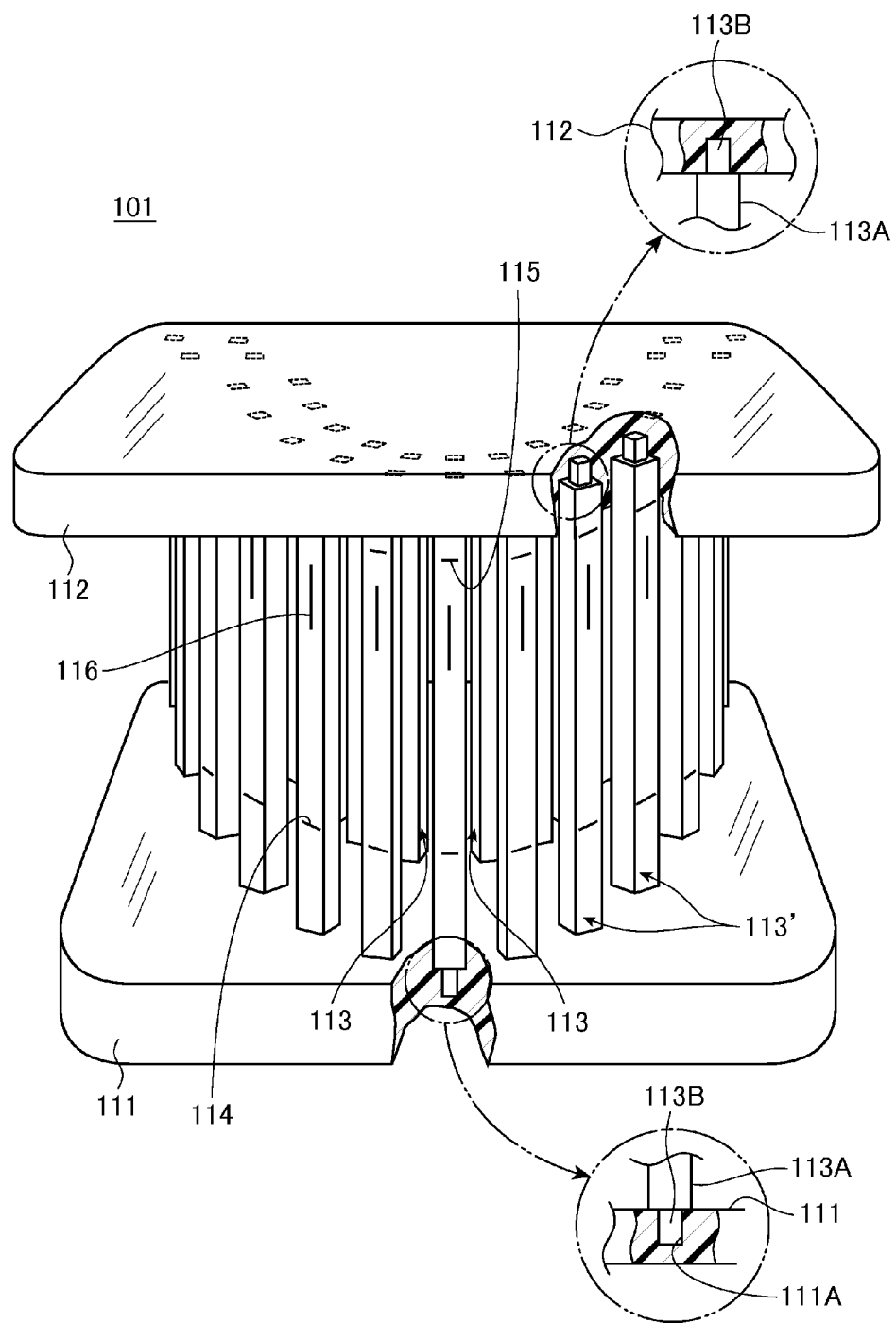
FIG. 7 is a perspective view, with partly cut away, showing an example of a phantom.

FIG. 7 shows the appearance of a partly sectioned phantom 101. This phantom 101 is a single universal phantom with which parameters necessary for the calibration can be measured. However, the phantom for the present invention will not always be limited to such a universal type phantom, but its configuration may be modified in various ways as long as the parameters for 3D image reconstruction can be calibrated as will be described. Some of such modifications will also be described later.

The universal phantom 101 includes a clear resin-made plate-shaped base 111, a clear resin-made top plate 112, and a plurality of pillars 113 held between the base 111 and the top plate 112. As will be described later, these pillars 113 (113') have metal markers of which X-ray transmittance differs from that of resin materials. By way of example, one type of resin is acrylic, but other types of resin may be used provided that the X-ray transmittance is different from that of the markers. The reason for using the clear resin is that it is easier to optically see the markers.

Each of the pillars 113 (113') has upper and lower ends respectively inserted into the base 111 and the top plate 112 and supported there. In the following, this support will be detailed.

Figure 8:
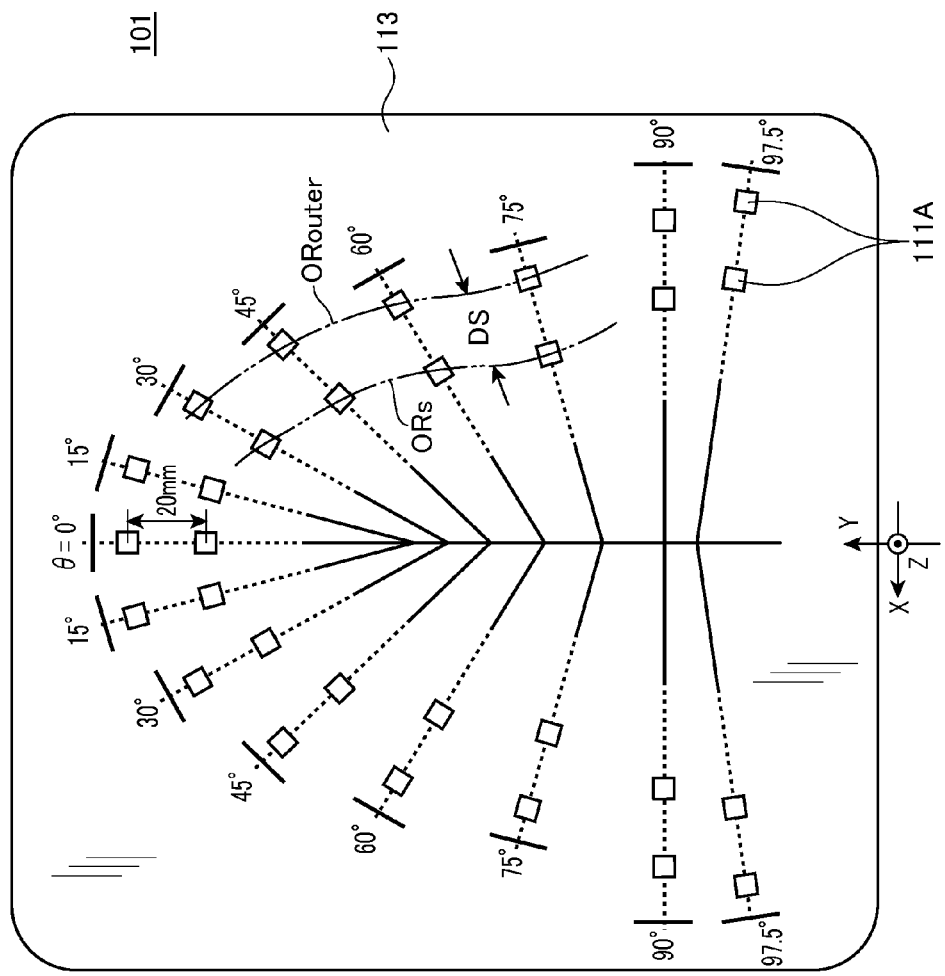
FIG. 8 is a plan view showing the base of the phantom, with which a relationship between planting positions of pillars with markers and positions of tomographic planes used for calibration.

As shown in FIGS. 7 and 8, the base 111 is shaped into a square plate and made of a clear resin material. On the upper surface of the base 111, a reference-plane trajectory $OR_s$ and an outer-plane trajectory $OR_{outer}$ are set, where the reference-plane trajectory $OR_s$ is formed by projecting the 3D referential tomographic plane SS onto the XY plane and the outer-plane trajectory $OR_{outer}$ is formed by drawing, for example, parallely with the reference-plane trajectory $OR_s$, a reference-plane trajectory at a position moved outwards apart from thereof by a predetermined distance DS, for example, 20 mm. These trajectories $OR_s$ and $O_{Router}$ may be depicted on the base 111 as actual lines so that an operator can easily recognize them, or those $OR_s$ and $OR_{outer}$ may be virtual.

On the upper surface of the base 111, there are formed square planting holes 111A at plural intersections at each of which both trajectories $OR_s$ and $OR_{outer}$ intersect with X-ray radiation angles θ produced when the X-ray tube 31 and the detector 32 are rotated to focus on the referential tomographic plane SS. The distance DS between both paths $OR_s$ and $OR_{outer}$ is not necessarily set to 20 mm, but may be another value provided that the parameters later described can be calculated accurately within limited size relations of the phantom.

Figure 9:
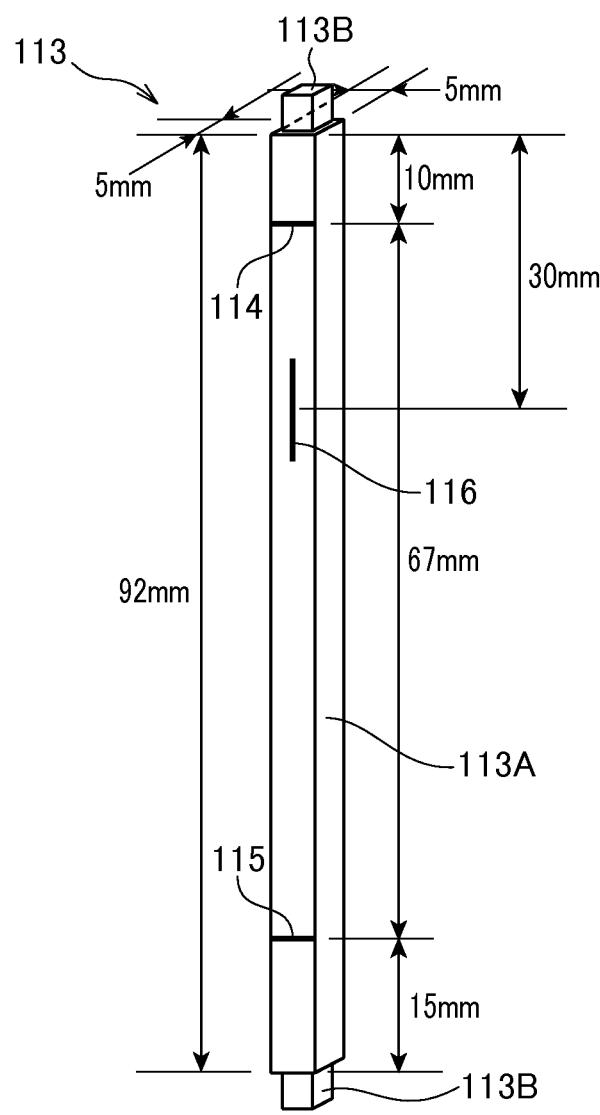
FIG. 9 is a perspective view explaining an example of the pillar being planted at the positions of the referential tomographic plane.
Figure 10:
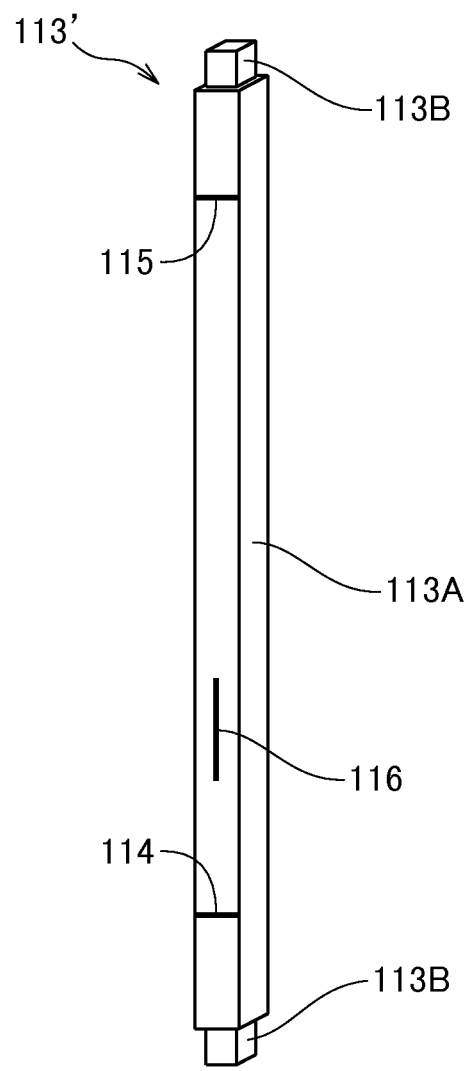
FIG. 10 is a perspective view explaining an example of the pillar being planted at the positions of an outer tomographic plane.
Figure 12:
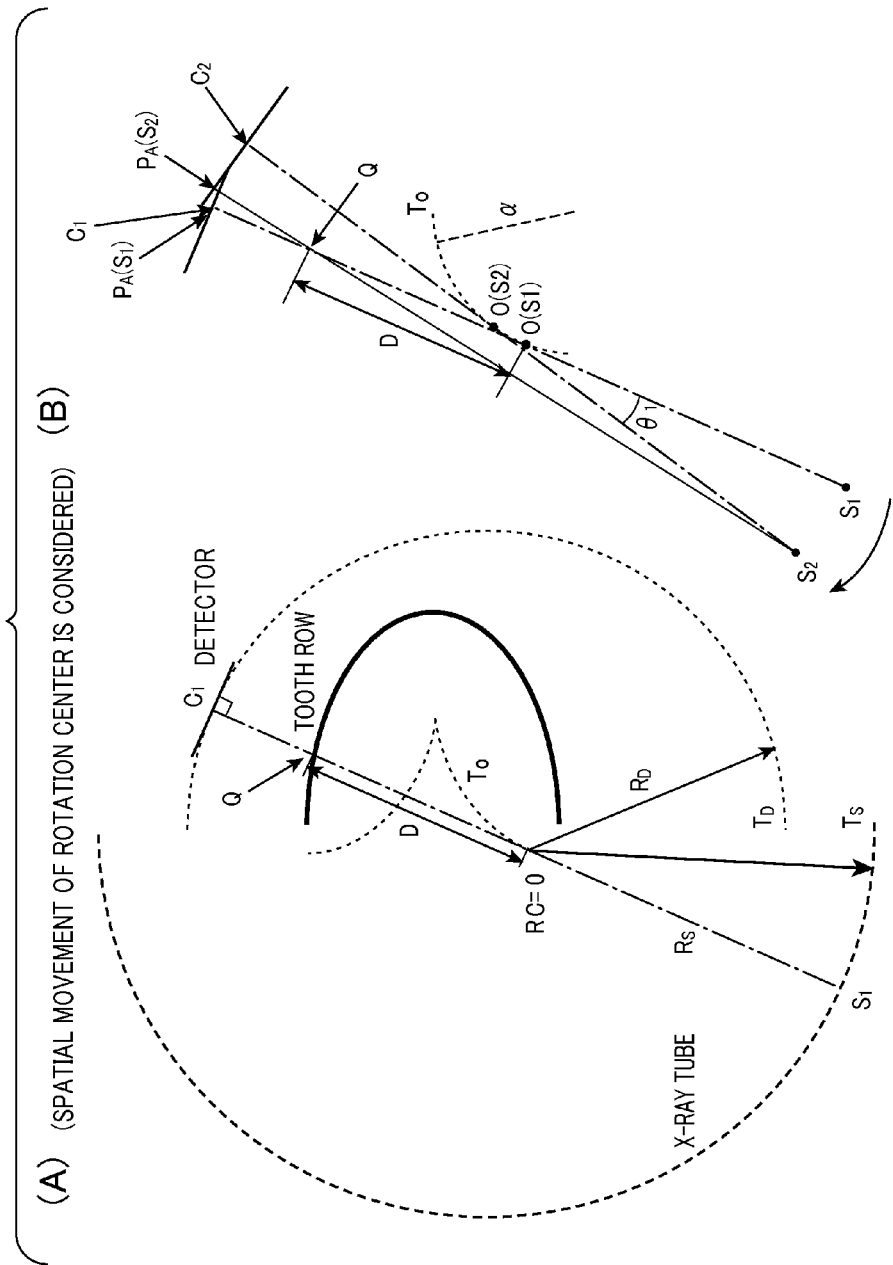
FIG. 12 shows illustrations explaining the principle of reconstruction of panoramic images according to the present invention.

As shown in FIGS. 9 and 10, each of the plural pillars 113 is a prismatic body which is made of resin such as acrylic. Each pillar 113 includes a prismatic pillar body 113A of a specific length and square prismatic protrusions 113B which are integrally protruded from the upper and lower ends of the prismatic pillar body. Each pillar body 113A has a section of a size of 5 mm×5 mm, for example, which is perpendicular to the longitudinal direction of the pillar body, and has a length of 92 mm. Each protrusion 113B has a section size smaller than that of the pillar body 113A, and for example, has a height of approximately 5 mm.

Each pillar body 113A has one surface on which first, second and third markers 114, 115 and 116 are arranged for calibration. These markers 114, 115 and 116 all are produced as small-diameter rods made of aluminum or brass, and have a diameter of 0.6 mm for example. Of these markers, the first and second markers 114 and 115 are laterally arranged at positions apart from the upper and lower ends of the pillar body 113A, respectively, by specific distances of, for example, 10 mm and 15 mm. On the surface of the pillar body 113A, there are provided semicircle-section notches of which diameters are for example 0.6 mm. The first and second markers 114 and 115, which are the small-diameter rods, are secured in the notches.

Moreover, as shown in FIG. 9, the third marker 116 is longitudinally arranged and centered at a position apart from the upper end of the pillar body 113A by a distance of 30 mm, for example. This third marker 116 has a specific length, for example, 20 mm. This third marker 116 is also planted in the same way as the first and second markers 114, 115.

The foregoing pillar 113 and the foregoing marker positions are simply examples, and design can be made with other appropriate sizes.

As described above, as shown in FIG. 7, the pillars 113 are arranged along the reference-plane trajectory $OR_s$.

On the other hand, the phantoms 113' arranged on the outer-plane trajectory $OR_{outer}$ are constructed as shown in FIG. 10. Interestingly, the phantom 113 shown in FIG. 32 can be reversed longitudinally to provide the phantom 113' shown in FIG. 10. Namely, on each of the phantoms 113', the second and first markers 115 and 114 are laterally located close to the upper and lower ends and the third marker 115 is located longitudinally at a position close to the first marker 114. How to plant the markers are totally the same as the foregoing, so that, when the phantom 101 is assembled, it is sufficient that the planting orientations of the pillars are reversed between the reference-plane trajectory $OR_s$ and the outer-plane trajectory $OR_{outer}$. That is, sharing of the pillars can be realized, whereby manufacturing cost can be reduced. Of course, another marker indicating each of the upper and lower ends may be provided to the pillars so as not to confuse the longitudinal orientations. Such additional markers should not influence X-ray transmission trough the pillars. Another variation for preventing such confusion is that the shapes of both planting protrusion 113B and planting hole 111A are differentiated between the base 111 and the top plate 112.

As described, the first and second markers 114, 115 are different in their planting orientations and their lengths from the third marker 116. The reason is that the calibration needs measurement of different parameters so that different types of markers are needed depending on shapes according to the attributes of the parameters. In the present embodiment, one of the features is that, as described, all necessary types of markers are efficiently arranged in space on the single phantom 101. It is therefore advantageous not to use plural phantoms respectively depending on parameter types.

Although being described later, the first and second markers 114 and 115 are used for acquiring both information indicative of distance relationships among the X-ray tube 31, the detector 32, the rotation center RC, and the 3D referential tomographic plane SS and information indicative of a height position of the X-ray tube 31 to the detector 32. In contrast, the third marker 116 is used for measuring amounts (=ΔX/ΔFi) called gains described later and actual projection angles respectively corresponding to the X-ray radiation angle θ.

To be specific, the first, second and third markers 114, 115 and 116 which are present along the reference-plane trajectory $OR_s$ and the outer-plane trajectory $OR_{outer}$ are imaged in both a referential panoramic image and an outer-plane panoramic image. This situation can be understood for example at an X-ray radiation angle θ=75°. In this example, the imaging of, for example, the referential panoramic images is depicted as shown in FIG. 11(A). That is, based on geometric relationships shown in FIG. 11(B), the referential panoramic image depicts in black, serially from the top, the first marker 114 ($OR_s$) located at the reference-plane trajectory $OR_s$, the second marker 115 ($OR_{outer}$) located at the outer-plane trajectory $OR_{outer}$, the third marker 116 ($OR_s$) located at the reference-plane trajectory $OR_s$, the third marker 116 ($OR_{outer}$) located at the outer-plane trajectory $OR_{outer}$, the second marker 115 ($OR_s$) located at the reference-plane trajectory $OR_s$, and the first marker 114 ($OR_{outer}$) located at the outer-plane trajectory $OR_{outer}$.

Conversely, the distance of the outer-plane trajectory $OR_{outer}$ to the reference-plane trajectory ORs and the longitudinal positions of the respective markers are set so as to provide such a serial arrangement of depiction of the markers. It should be noted that in this case, the images of the markers 114 ($OR_{outer}$), 115 ($OR_{outer}$) and 116 ($OR_{outer}$) located at the outer-plane trajectory $OR_{outer}$ blur more than that of such markers located at the reference-plane trajectory $OR_s$. Incidentally if shift & add amounts for reconstructing a panoramic image are changed so as to focus on the outer tomographic plane, the relationship showing a degree of the blur, i.e., an optimal focusing becomes opposite to each other between both paths.

In the panoramic image, the images of the four markers 114 ($OR_s$), 115 ($OR_{outer}$), 115 ($OR_s$), and 114 ($OR_{outer}$) are depicted as lateral black lines. These images are used to measure parameters showing distance relationships among the X-ray tube 31, the detector 32, the rotation center RC, the referential tomographic plane SS, and parameters showing a height position of the X-ray tube 31 to the detector 32. Images of the two markers 116 ($OR_s$) and 116 ($OR_{outer}$) are depicted as longitudinal black lines and used to measure a later-described amount (=$\Delta X/\Delta Fi$) called gain and actual projection angles respectively corresponding to the X-ray radiation angle θ. In cases where an X-ray radiation angle is different from a designed or specified value, an actual projection angle is also different from such a value. In this case, the longitudinal black lines imaged as the two markers 116 ($OR_s$) and 116 ($OR_{outer}$) are positionally not matched to each other, being shifted from one the other in the lateral direction. Calculating such a shift amount will lead to measurement of an actual projection angle.

In this way, the phantom 101 can provide, through the single scan, necessary and sufficient positional information concerning the distances and heights of the imaging system positioned in the imaging space. Thus this phantom 101 provides general versatility that allows different types of parameters to be measured with the sole phantom.

In the foregoing phantom construction, it is not always necessary to arrange the top plate 112. However, preferably, it is desired to arrange the top plate 112, as the plural pillars 113 planted on the base 111 need to keep spatially accurate positions of the markers 114, 115 and 116. To prevent the pillars 113 from tilting, moving, and being damaged during installation and storing of the phantom, it is preferable to have the top plate 112. Alternatively, resin-made pillars just for supporting both upper and lower plates may be installed between the top plate 112 and the base 111.

(Principle of Reconstruction)

Principle of reconstruction performed by the panoramic imaging apparatus will now be described mathematically.

FIG. 12(A) illustrates the X-ray tube 31 and the detector 32 which are opposed to each other and rotate (move) along mutually different curved orbits $T_S$ and $T_D$ around an approximately horseshoe-shaped tooth row. The X-ray tube 31 rotates along one of the orbits, $T_S$, while the detector 32 rotates the other orbit $T_D$. That is, the X-ray tube 31 and the detector 32 rotate as paired device, and the center of rotation (rotation center) RC of the paired devices is also moved. In the example shown in FIG. 12(A), the rotation center RC moves along a chevron-shaped trajectory C shown in FIG. 2, but this is just an example. The same principle described here is also true of the trajectory A and the trajectory B, which are shown in FIG. 2.

It is now assumed that, as shown in FIG. 12(A), the rotation center RC of the paired X-ray tube 31 and detector 32 is present at a position O, the focus position of the X-ray tube 31 is $S_1$, the position of the center in the width direction of the detector 32 is $C_1$, the rotation radius of the X-ray tube 31 (hereinafter referred to as an X-ray tube—rotation center distance) is $R_S$, the rotation radius of the detector 32 (hereinafter referred to as a detector—rotation center distance) $R_D$, a distance from the rotation center RC, i.e., position O, to a point Q in the tooth row (hereinafter referred to as a rotation center—referential tomographic plane distance is D, and a trajectory drawn by the rotation center RC is $T_O$. The distances $R_s$ and $R_d$ are fixed amounts.

Further FIG. 12(B) shows a state where the focus position S of the X-ray tube 31 is rotated and moved from $S_1$ to $S_2$, and in response to this movement, the trajectory $T_O$ of the rotation center RC moves along a circle of a radius α at an angular speed curve ω so that the rotation center RC moves from $O(S_1)$ to $O(S_2)$. In this case, an angle $\theta_1$ made between the two positions $O(S_1)$, $O(S_2)$ of the rotation center RC and the positions S1, S2 which are the focus positions is $\theta_1=\omega t$ (t: time). During such movement, a projected point of the point Q of the tooth row, which is projected to the detector 32, changes from $P_A(S_1)$ to $P_A(S_2)$. During this movement, the center position of the width direction of the detector 32 also moves $C_1$ to $C_2$.

The geometrical relationship shown in FIG. 12(B) includes a relationship between the movement of the rotation center RC which is from the positions $O(S_1)$ to $O(S_2)$ and the trajectory $T_O$, so that such included relationship can be focused and described as shown FIG. 13(A). As a distance between both positions $O(S_1)$ and $O(S_2)$ is minute, the distance can be denoted as $\theta_1\alpha$ by using the angle $\theta_1$ and the radius α. This results in that all of the rotation center positions $O(S_1)$, $O(S_2)$, the X-ray focus position $S_2$, and the reconstruction position Q can be expressed using distance relationships, which can be shown as in FIG. 13(A). To be specific, when a distance between the X-ray tube position $S_2$ and the rotation center position $O(S_2)$ equals the X-ray tube–rotation center distance $R_s$ and a distance between the rotation center $O(S_2)$ and the detector center position $C_2$ equals the detector–rotation center distance $R_d$, a distance between the rotation center positions $O(S_1)$ and $O(S_2)$ is $\alpha\theta_1$, a distance between the rotation center position $O(S_2)$ and the reconstruction position Q is $D-\alpha\theta_1$, a segment produced by drawing a vertical line from the reconstruction position Q to the segment $o(S_2)$-C2 is $(D-\alpha\theta_1)\sin\theta$, and a distance between an intersection B of the vertical line and the rotation center position $O(S_2)$ is $(D-\alpha\theta_1)\cos\theta_1$.

In the present embodiment, it is a feature that calculation for calibrating parameters, which are necessary for an analysis of geometrical positional relationships of the imaging system operated in the imaging space (that is, a structural analysis) and 3D image reconstruction that extracts an actually existing position of a tooth row located in the imaging space (that is, autofocus), takes into account the distance α between the rotation center positions $O(S_1)$ and $O(S_2)$.

(Calculation of Gains)

Using the distance relationships shown with FIG. 13(B), an amount which is referred to as a gain (=$\Delta X/\Delta Fi$) will now be obtained.

From the geometrical relationships shown in FIG. 13(B), a formula of $$x=[(Rs+Rd)/\{Rs+(D-a\theta_1)\}]\cdot(D-\alpha\theta_1)\sin\theta_1 \quad (1)$$

is realized. When understanding $\alpha\theta_1$ as a correction term $M(=\alpha\theta_1)$, an approximated formula of $$\Delta x/\Delta\theta=\{(Rs+Rd)/(Rs+(D-M))\}(D-M) \quad (2)$$

is realized, where $\theta_1$ and x are minute and negligible.

When the frame data outputted from the detector 32 are denoted as Fi, a formula of $$\Delta x/\Delta\theta=(\Delta x/\Delta Fi)(\Delta Fi/\Delta\theta) \quad (3)$$

is obtained, so that a formula of $$\Delta x/\Delta Fi=(\Delta\theta/\Delta Fi)\{(Rs+Rd)/(Rs+(D-M))\}(D-M) \quad (4)$$

is obtained.

The left-had side $\Delta x/\Delta Fi$ of the formula (4) is called a gain (i.e., change rates in shift & add amounts). Namely this gain $\Delta X/\Delta Fi$ shows change rates in shift & add amounts used by the tomosynthesis technique (that is, shift & add calculation), where plural frame data are mutually shifted and added under the tomosynthesis technique.

Further, in the right-hand side of the formula (4), the term $R_S+R_D$ shows a distance between the detector and the X-ray tube (the detector–X-ray tube distance), the term $R_S+(D-M)$ shows a distance between the X-ray tube and the focus (the focus–X-ray tube distance), which is corrected by an amount corresponding to the movement distance $\alpha\theta_1$ between the rotation center positions $O(S_1)$ and $O(S_2)$. Additionally, the term (D−M) shows a distance between a new rotation center position from which an amount corresponding to the movement distance $\alpha\theta$ is deducted, and the reconstruction point Q.

In this way, a curve of gains $\Delta X/\Delta Fi$ (simply, a "gain curve") can be calculated on the basis of the detector–X-ray tube distance $R_S+R_D$, the focus position–X-tray tube distance $R_S+(D-M)$, the rotation center–reconstruction point distance (D−M), and an angular speed curve $\Delta\theta/\Delta Fi$ (refer to FIG. 17) indicating a relationship between frame data Fi and rotation angles θ. This gain curve is subjected to integration with the center of the anterior teeth located at the center of an image, a panoramic image focusing on the position apart from the rotation center RC by the distance D can be reconstructed at each of the rotation angles.

As described in JPA-2007-136163, the foregoing gain $\Delta X/\Delta Fi$ is different in a concept of magnitudes from a gain used in normal electric circuits. In this embodiment, the larger the gain $\Delta X/\Delta Fi$, the smaller an overlapped amount (shift amount) applied to frame data to be added pixel by pixel to each other. In this embodiment, as the gain $\Delta X/\Delta Fi$ becomes smaller, the overlapped amount becomes larger.

In the present embodiment, parameters necessary for a structural analysis of the imaging space and for calibration are obtained using the calibration phantom and the foregoing gain formula (4). Hence, the calibration phantom will now be described in terms of its construction and functions, prior to a description of imaging.

(Calculation of Parameters)

Figure 14:
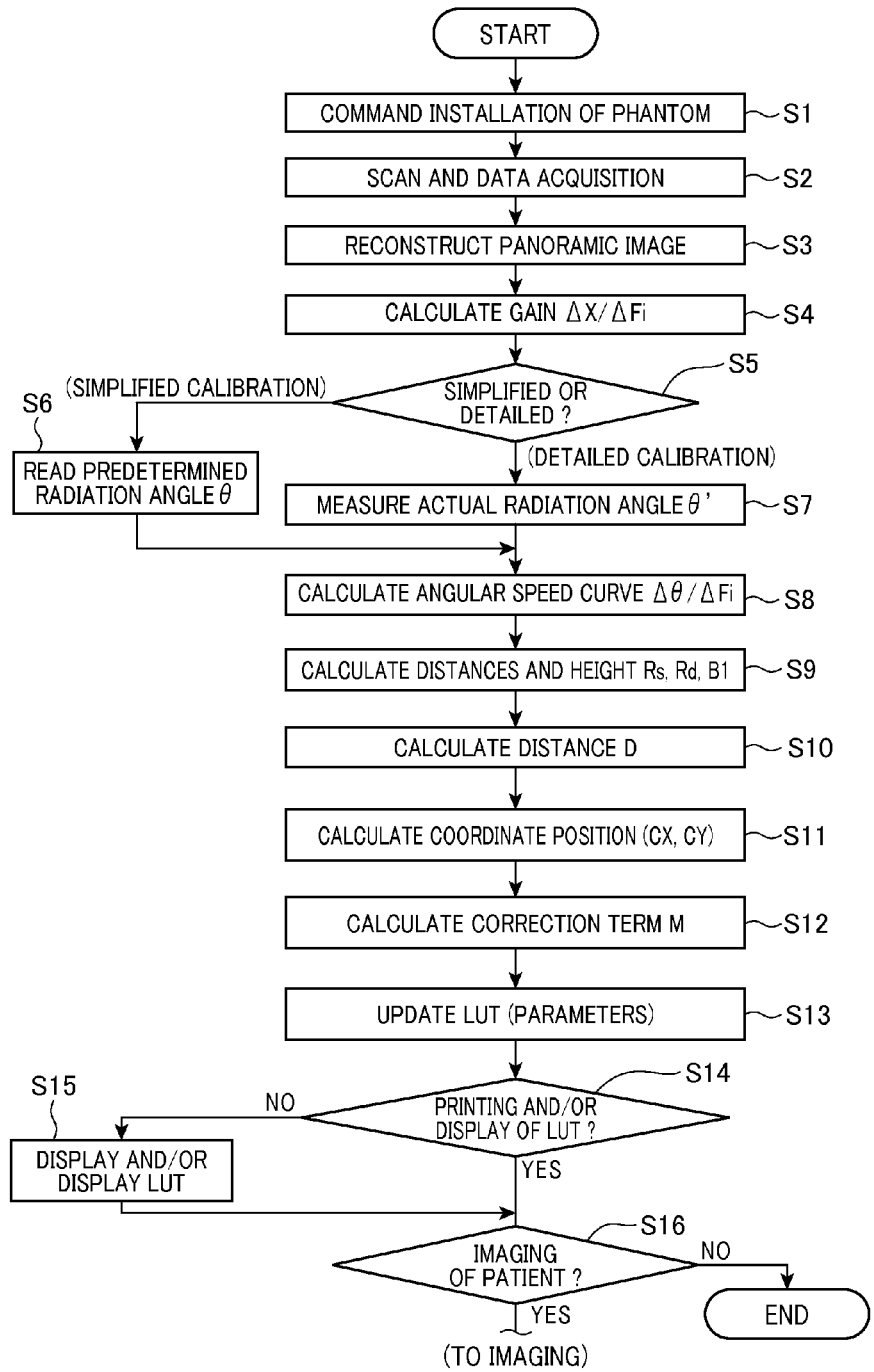
FIG. 14 is a flowchart outlining steps for a structural analysis of the imaging space and the calibration, which is executed cooperatively by the controller and the image processor.
Figure 15:
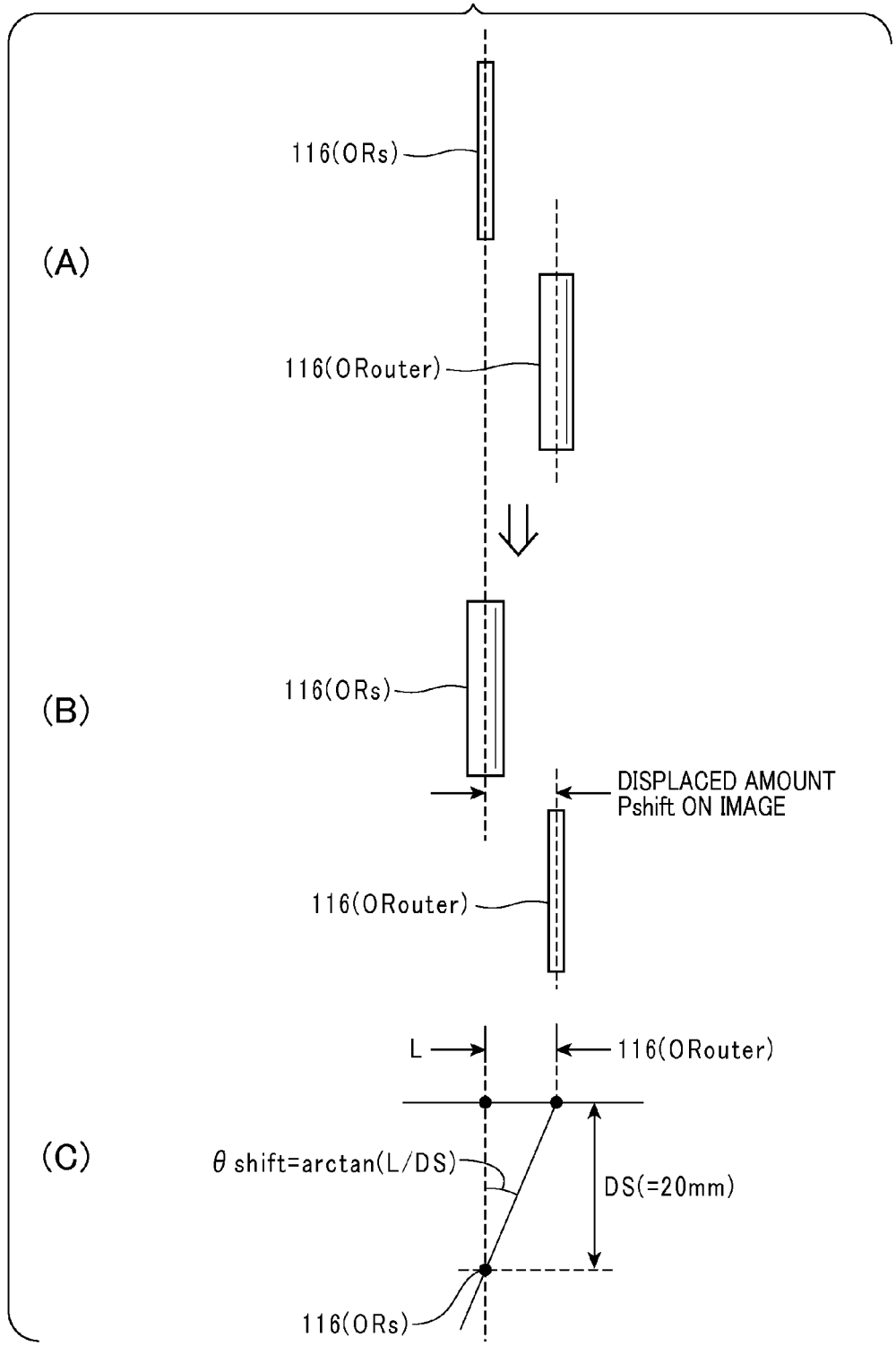
FIG. 15 shows illustrations explaining steps for measuring shifts in the radiation (projection) angle of an X-ray.

Referring to FIG. 14, calculation for measuring the parameters necessary for a structural analysis of the imaging space and for calibration will now be described. The parameters being measured here are the X-ray tube–rotation center distance Rs, the detector–rotation center distance Rd, and the Z-axial height B1 of the X-ray tube 31 to the detector 32, which are used for the structural analysis; and the gain $\Delta x/\Delta Fi$, the X-ray radiation angle θ, the angular speed curve $\Delta\theta/\Delta Fi$, the rotation center–referential tomographic plane distance D, the correction term M, and the coordinate (CX, CY) of the moving rotation center RC in the X-Y plane, which are used for the calibration.

Among them, the parameters for the calibration "$\Delta x/\Delta Fi$, θ, $\Delta\theta/\Delta Fi$, D, M, (CX, CY)" are stored and updated in a look-up table LUT of the input values Fi.

Processing for calculating these parameters is performed through the following processes.

Process 1: installation of the phantom and X-ray radiography (scan) for the calibration;
Process 2: calculation of a profile of the gain $\Delta x/\Delta Fi$;
Process 3: calculation of a displacement of the X-ray radiation angle θ (i.e., an actual X-ray projection angle θ');
Process 4: calculation of the angular speed curve θ=f(Fi): $\Delta\theta/\Delta Fi$
Process 5: calculation of the parameters Rs, Rd, B1;
Process 6: calculation and update, that is, calibration of parameters $\Delta x/\Delta Fi$, θ, $\Delta\theta/\Delta Fi$, D, M, (CX,CY); and
Process 7: 3D reconstruction with actual positions of a tooth row depicted. These processes are performed during the performance of a flowchart shown in FIG. 14, which is performed cooperatively by the controller 57 and the image processor 56.

<Process 1>

The controller 57 commands an operator to install the phantom 101 at a predetermined position in the imaging space, via screen display and/or sound messages (step S1). The predetermined position referred here is a position on the chinrest 25 on which the jaw of a patient P will be rested during imaging.

The controller 47 then commands the apparatus to perform a calibrating scan via the operation device 48 (step S2). Responsively to this command, the controller 57 reads a program for the calibrating scan, which is previously stored in the ROM 61, into a work area of the controller. The controller 57 executes steps of the program, which makes the X-ray tube 31 with the collimator 33 and the detector 32 rotate around the phantom. During this rotation, for example, pulsed X-rays are radiated from the punctate X-ray focus of the X-ray tube 31, and the pulsed X-rays are collimated into a fan-shaped X-ray beam by the collimator 33. This X-ray beam is transmitted through the phantom, and enters the detection surface of the detector 32. Hence, the detector 32 detects the X-ray beam which has been transmitted through the phantom, and outputs at intervals (for example, 300 fps) electric digital frame data corresponding to the detected X-ray beam.

The rotation of both the X-ray tube 31 and the detector 32 is not a simple circulation around the phantom. As shown in FIG. 12(A), with the X-ray 31 and the detector 31 always kept to be opposed to each other, the X-ray 31 and the detector 31 are rotated such that the rotation center RC in a line connecting both devices positionally trances a trajectory which first moves closer to a frontal portion of the phantom and then moves away from the phantom. That is, during an actual scan, the rotation center RC moves closer to the tooth row as advancing toward the anterior teeth of the tooth row, so that the rotation center RC is positionally shifted. To allow this movement, rotated positions and angular speed curves of both the X-ray tube 31 and the detector 32 are controlled individually.

The frame data outputted from the detector 32 are temporarily stored in the buffer memory 53. The image processor 53 uses such frame data to reconstruct a referential panoramic image of the referential tomographic plane SS under the tomosynthesis technique (step S3).

<Process 2>

The image processor 56 then calculates the gain $\Delta X/\Delta Fi$ (step S4).

First, in the reconstructed referential panoramic image, the numbers of frame data $Fi_0$ is decided. This decision is performed by an operator who visually views the referential panoramic image, in such a manner that each of such reconstructed frame data provides a panoramic image in which the markers on each of the pillars of the phantom 101 are centered and depicted. As described, the pillars are arranged at each of the X-ray radiation angles θ along the referential plane positions tracing the path of the referential tomographic plane SS. Incidentally, this referential panoramic image includes images of the phantoms secured to the pillars arranged at each of the X-ray radiation angles θ along outer plane positions tracing the path of the outer plane located outside by 20 mm from the referential tomographic plane SS.

For the phantoms of each of the pillars standing at the referential plane positions, an amount of overlapping (i.e., a shift & add amount) of frame data Fi, which provides best focus, is then decided. This is also decided by the operator who visually observes the referential panoramic image during which the operation device 58 is manipulated. This observation and manipulation is repeatedly performed by trial and error, in which frame data Fi on both sides of the center frame data $Fi_0$ are overlapped on one another to check a degree of blur in an overlapped image. In this way, the center frame data $Fi_0$ respectively directed to the markers on each of the pillars standing along the referential tomographic plane SS and optimum amounts of overlapping for each of the center frame data have been decided. Such decided data are smoothly connected with each other to obtain a profile Px of the amounts of overlapping. This profile Px is the used to obtain a gain X/ΔFi at each of the X-ray radiation angles θ which have been set.

A modification is provided, where the amounts of overlapping are taken as an abscissa axis and statistic amounts of edges of the marker images (for example, half bandwidths) are taken as an ordinate axis. It may be possible to estimate an overlapping amount which provides a peak to the edge statistic amounts of the marker images. Such estimated overlapping amount provides an optimum overlapping amount. Hence, by positionally specifying the marker images depicted in the referential panoramic image via ROIs for example, it is possible to almost automatically calculate optimum overlapping amounts at the specified positions.

The image processor 56 then responds to a command from the controller 57 to receive a command of what type of calibration should be performed. In the present embodiment, there are provided two types of calibration. One type is a simplified calibration with which no calibration is performed for the X-ray radiation angles θ, but default amounts for the respective X-ray radiation angles θ, which are previously provided by the system, are employed as they are. The other type of calibration is a detailed calibration with which the phantom 101 is scanned to obtain a panoramic image and, from this panoramic image, the X-ray radiation angles θ are also calibrated. Thus, prior to calibration, the controller 57 enables the monitor 60 to display an image to ask the operator to desire which type of calibration, i.e., the simplified calibration or the detailed calibration. When receiving a command from the controller 57, the image processor 56 determines whether a desired calibration technique is the simplified type or the detailed type (step S5).

When it is determined to perform the simplified calibration, the image processor 56 reads values of radiation angles θ=0°, ±15°, ±30°, . . . , which are previously set as shown in FIG. 2, for example, and sets those values to the radiation angles, as they are (step S6). In contrast, when it is determined that the detailed calibration technique be employed, displacements of X-ray radiation angles θ, that is, actual radiation angles θ', are calculated from a panoramic image.

<Process 3>

Then, a displaced amount $θ_{shift}$ of each of the actual radiation angles (projection angles) θ' in relation to the X-ray radiation angles θ is calculated (step S7).

Through this calculation, similarly to that at step S4, concerning with the markers on the pillars arranged every X-ray radiation angle θ at the outer-plane positions which are along an outer tomographic plane, which is separated 20 mm outside of the referential tomographic plane SS, a gain ΔX/ΔFi for each X-ray radiation angle and a profile of the gains ΔX/ΔFi are produced based on the reconstructed referential panoramic image. The data of this profile is used to reconstruct an outer-plane panoramic image of a section separated 20 mm outside of the referential tomographic plane SS. In this outer-plane panoramic image, a physical lateral center position of each phantom on each of the pillars 113' located at the outer plane positions is decided. The lateral direction corresponds to a lateral direction in a two-dimensional referential panoramic image. This decision is also performed by an operator who visually observes the panoramic image.

Figure 16:
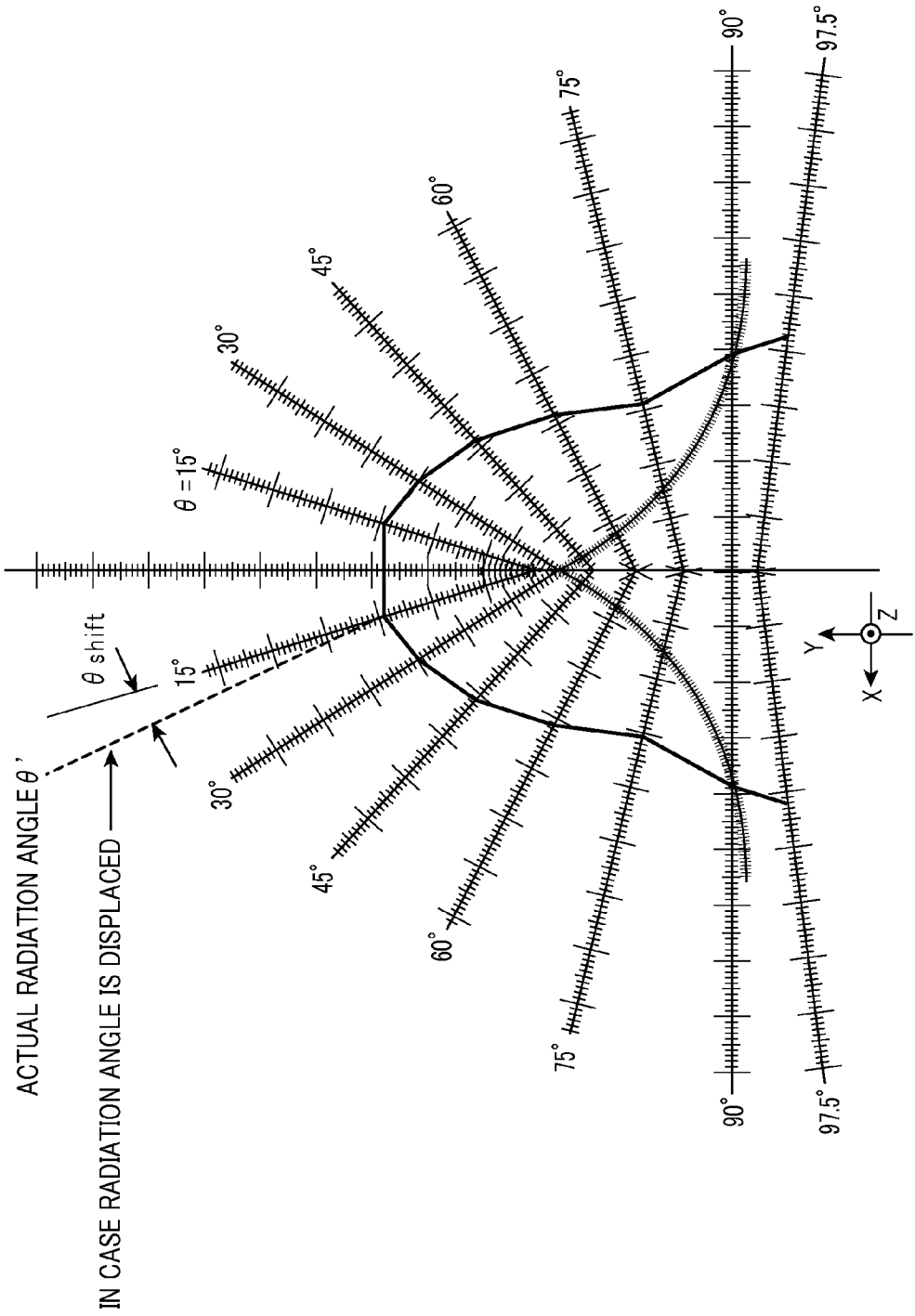
FIG. 16 shows an illustration explaining a displacement in the radiation angle of the X-ray.

The number $Fi_0$ of the central frame data imaging the markers on each pillar standing at each reference plane position has already been decided at step S4. Hence, from the lateral position (refer to FIG. 15(A)) of each marker in the outer-plane panoramic image (the lateral direction of the two-dimensional referential panoramic image), which marker is imaged in the center frame data, and from the lateral position (refer to FIG. 15(B)) of each outer-plane-positioned marker 116 in the outer-plane panoramic image, a displacement amount $P_{shift}$ between both markers in the images is calculated. This displacement amount $P_{shift}$ is converted to an actual-size displacement amount L (refer to FIG. 15(C)). Using this displacement amount L and the known distance DS (20 mm in the present embodiment) between both paths $OR_s$ and $OR_{outer}$, a displacement amount $θ_{shift}$=arctan (L/DS) for the actual radiation angle θ' is calculated. This calculation is carried out every angle θ (=0°, ±15°, ±30°, . . . ). Hence, at each of the X-ray radiation angles θ which are set every predetermined angle, the displacement amount $P_{shift}$ for the actual radiation angle θ' can be obtained. FIG. 16 exemplifies this displacement amount $P_{shift}$.

<Process 4>

The image processor 56 then calculates a projection angle curve θ=f(Fi), i.e., the angular speed curve Δθ/ΔFi (step S8).

In the detailed calibration, the displacement amount $θ_{shift}$ of the actual radiation angle θ', which shows a displacement from each X-ray radiation angle θ, has already been obtained. This displacement amount $θ_{shift}$ is used to obtain a radiation angle θ' of each of the markers located along the referential tomographic plane SS. In the simplified calibration, designed default angles θ, which can be employed easily, are used without any correction.

Figure 17:
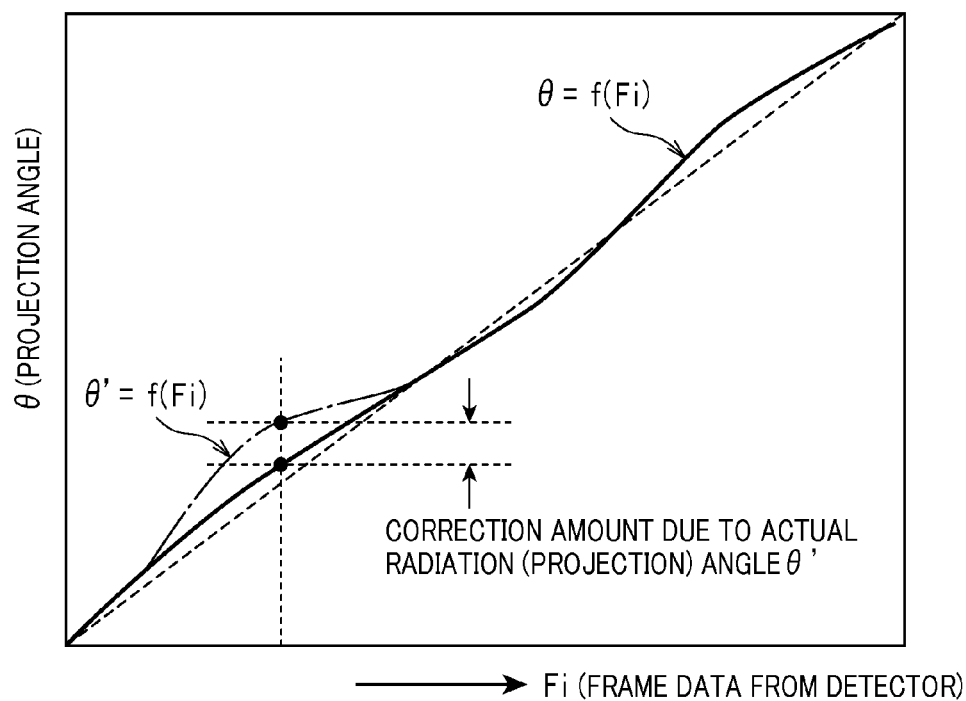
FIG. 17 is a view explaining an example of an angular speed curve and correction of the curve according to shifts in actual radiation angles.

As described, at the foregoing step S4, the number of the center frame data $Fi_0$ centering on each of the markers at the X-ray radiation angle θ, which markers are along the referential tomographic plane SS, has been known. Connecting frame data Fi acquired at the actual radiation angles θ or the designed default radiation angles θ and smoothing the connected frame data provides a projection angle curve θ=f(Fi). FIG. 17 exemplifies this projection angle curve θ=f(Fi). In this figure, a projection angle curve θ=f(Fi) shows that the original projection angle curve θ=f(Fi) is corrected in accordance with the actual radiation angle θ'.

<Process 5: Calculation of Constant Parameters at an X-Ray Radiation Angle θ=0 Degrees>

Then, from the panoramic image, the image processor 56 calculates, as constant parameters, the X-ray tube–rotation center distance $R_s$, the detector–rotation center distance $R_d$, and the height information B1 of the focus position of the X-ray tube, all of which are provided at an X-ray beam radiation angle of 0 degrees (step S9).

Figure 18:
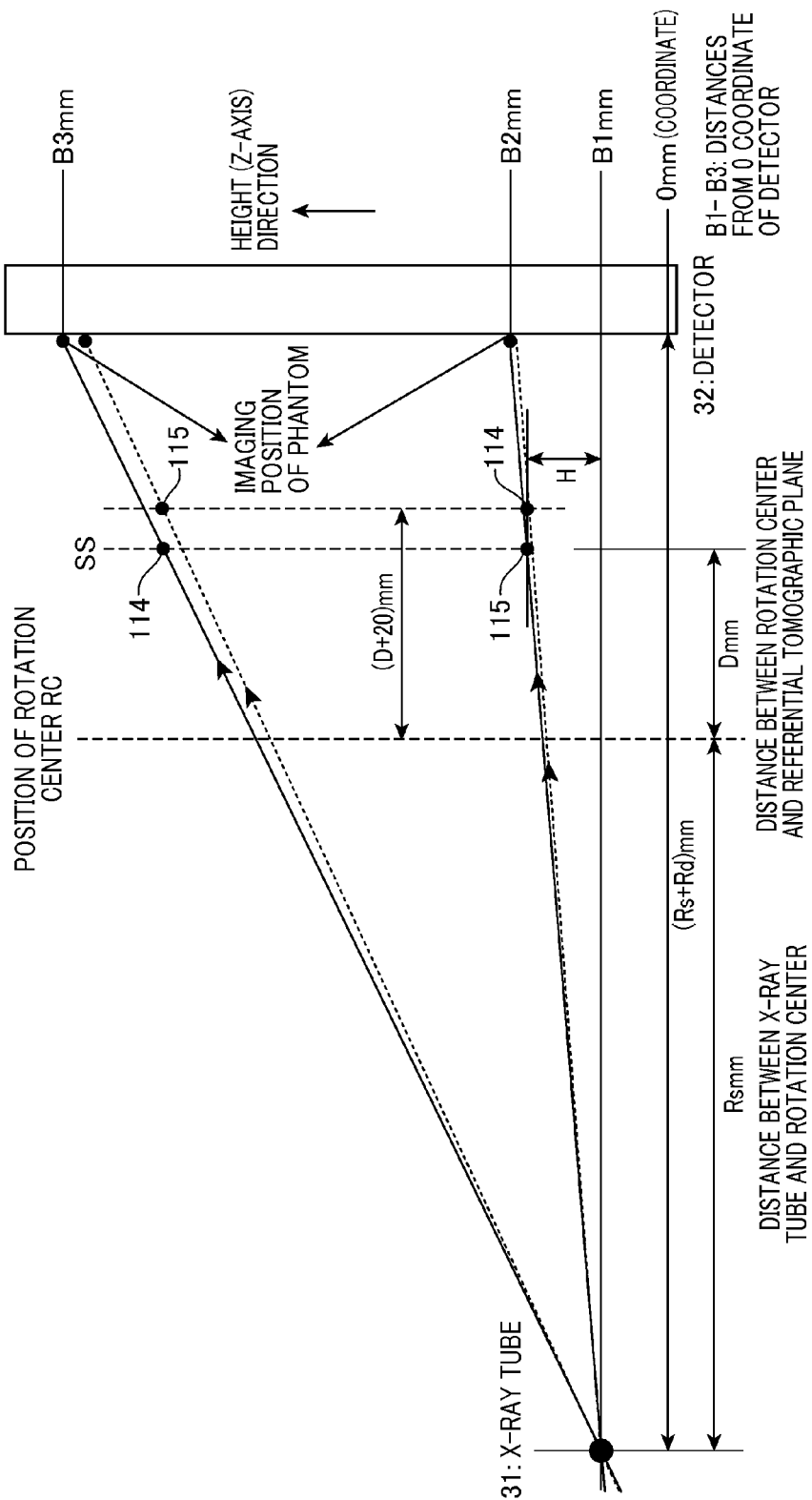
FIG. 18 is a view explaining a positional relationship between the marker at an X-ray radiation angle of 0 degrees and an imaging position of the marker.

As shown in FIG. 18, the X-ray tube 31 and the detector 32 are located to be opposed to each other, between of which the rotation center RC and the referential tomographic plane SS are positioned. At the position where the referential tomographic plane SS is present, the two markers 114 and 115 exist which are mutually separated 67 mm in the vertical direction. The X-ray focus of the X-ray tube 31 is small enough so as to be a punctate X-ray source (for example, a diameter of 0.5 mm). The radiation angle θ of this X-ray beam is 0 degrees. That is, the X-ray beam collimated by the collimator 33 is radiated to a central portion of anterior teeth of a tooth row assumed to be located along the referential tomographic plane SS. This X-ray beam is obliquely transmitted through the two markers 114 and 115, the transmitted beam is projected to the detection surface of the detector 32. This projection produces projected points at positions of heights B2 and B3 on the detection surface. Concretely the heights up to the markers 114 and 115 are enlarged in the longitudinal (Z-axis) direction and projected onto the projected points B2 and B3 being imaged. The lowermost end position of the detection surface of the detector 32 is set to the coordinate of 0, i.e., the origin, and the X-ray focus position has a height B1 when being calculated from a horizontal plane (X-Y plane) passing through the origin. Hence, along the detection surface of the detector 32, positions showing the origin of which coordinate is 0, the X-ray focus height B1, and the projection heights B2, B3 of the markers 114, 115 are mapped in this order from its lower end.

The foregoing gain formula (4) of $$\Delta x/\Delta Fi = (\Delta\theta/\Delta Fi)\{(R_s + R_d)/(R_s + (D-M))\}(D-M)$$

is applied to the geometrical relationship at the X-ray radiation angle of $\theta=0°$ which is pictorially shown in FIG. 18. In this X-ray radiation angle of $\theta=0°$, as can be understood from (A) and (B) of FIG. 13, the correction term M is regarded as 0 (M=0). Hence, the formula (4) can be converted to $$\Delta x/\Delta Fi = (\Delta\theta/\Delta Fi)\{(R_s + R_d)/(R_s + D)\}D \quad (5).$$

Based on calculation of enlargement factors of the markers 114 and 115 in the image, a relationship of $$(R_s + R_d)/(R_s + D) = (B3_{(D)} - B2_{(D)})/67 = K_{(D)} \quad (6)$$

is provided, wherein an enlargement factor $K_{(D)}$ is a known value. Specifically, this factor $K_{(D)}$ can be known from projected positions B2 and B3 detected by the detector 32, where such projected positions are given by the markers 114 and 115 located along the referential tomographic plane and at the X-ray radiation angle of $\theta=0°$.

Similarly, a relationship of $$(R_s + R_d)/(R_s + D + 20) = (B3_{(D+20)} - B2_{(D+20)})/67 = K_{(D+2)} \quad (7)$$

is provided, wherein an enlargement factor $K_{(D+20)}$ is also a known value. Specifically, this factor $K_{(D+20)}$ can be known from projected positions B2 and B3 detected by the detector 32, where such projected positions are given by the markers located along the plane separated 20 mm outside of the referential tomographic plane and at the X-ray radiation angle of $\theta=0°$.

Hence, the foregoing formulae (6) and (7) still provide $$(R_s + R_d)/(R_s + D) = K_{(D)} \quad (8)$$

$$(R_s + R_d)/(R_s + D + 20) = K_{(D+20)} \quad (9).$$

When a relationship of $$X = R_s + R_d, Y = R_s + D \quad (10)$$

is used, there are provided $$X/Y = K_{(D)} \quad (11)$$

$$X/(Y+20) = K_{(D+20)} \quad (12),$$

from which values of X and Y can be calculated.

Further, using the formula (8), the formula (5) can be converted to $$\Delta x/\Delta Fi = (\Delta\theta/\Delta Fi) \cdot K_{(D)} \cdot D \quad (13).$$

In this formula (13), amounts of terms other than the rotation center–referential tomographic plane distance D are all known, so that the formula (13) provides such a distance D at the X-ray radiation angle $\theta=0°$. When this distance D becomes known, the formula (10) can be used, as the values of X and Y have been known, which provides respective amounts of both the X-ray tube–rotation center distance $R_s$ and the detector–rotation center distance $R_d$ at the X-ray radiation angle $\theta=0°$.

After obtaining the distances D, $R_s$, and $R_d$, solving two formulae of $$(B2_{(D+20)} - B1)/H = K_{(D+20)} \quad (14)$$

$$(B2_{(D)} - B1)/H = K_{(D)} \quad (15),$$

which are geometrically realized in FIG. 18, can provide values of both the position B1 of the X-ray tube 31 in the longitudinal (Z-axis) direction and the height H up to the lower phantoms from the X-ray tube 31.

<Process 6: Calculation of Functional Parameters Whose Input is Frame Data Fi, at X-Ray Radiation Angles Other than an Angle $\theta=0$ Degrees>

Figure 19:
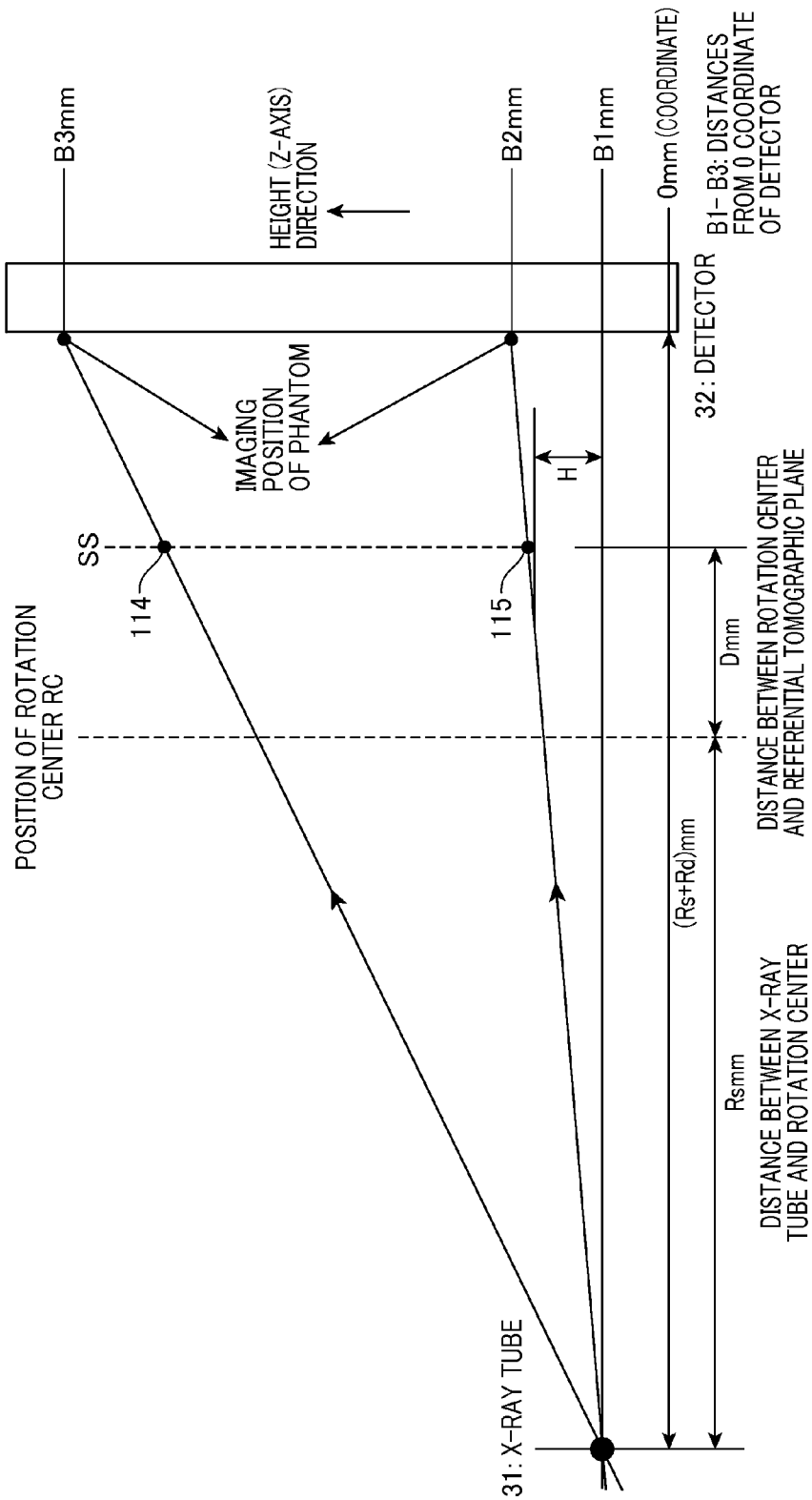
FIG. 19 is a view explaining a positional relationship between the markers at angles other than an X-ray radiation angle of 0 degrees and imaging positions of the markers.
Figure 20:
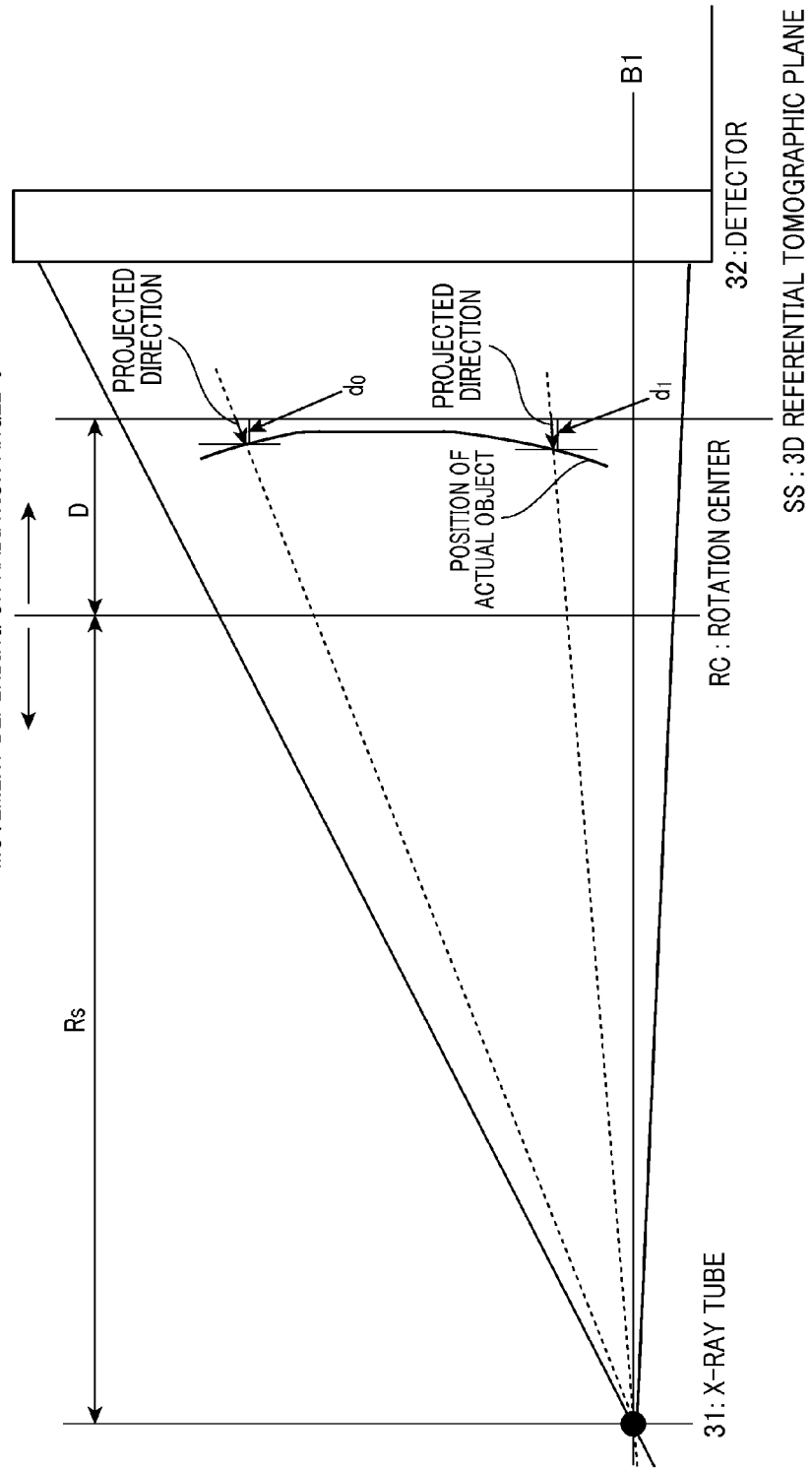
FIG. 20 is a view outlining three-dimensional projection along a direction viewing the X-ray tube position, with consideration of correction of the longitudinal enlargement factor, in the present embodiment.

In this case, at each radiation angle $\theta$, a geometrical relationship among the X-ray detector 31, the detector 32, the rotation center RC, and the phantom (markers) can be shown as in FIG. 19.

Even at X-ray radiation angles other than the angle $\theta=0$ degrees, the foregoing formulae (6) and (8) are realized. Hence, projected images $B3_{(D)}$ and $B2_{(D)}$ produced at positions B2 and B3 by the markers 114 and 115 are obtained at each of the radiation angles $\theta$. Hence, using the formulae (6) and (8), the rotation center–referential tomographic plane distance D is calculated at each radiation angle $\theta$(step S10). This known distance D are the already known X-ray radiation angle $\theta$ or its actual value $\theta'$ which has also been known are used to positional coordinates (CX, CY) of the rotation center RC (step S11).

Moreover, at the X-ray radiation angles $\theta$ other than 0 degrees, it is necessary to take the correction term M ($\neq 0$) into consideration, as can be understood from (A) and (B) of FIG. 13. Hence, it is necessary to replace the foregoing formula (4) with $$\Delta x/\Delta Fi = (\Delta\theta/\Delta Fi)\{(R_s + R_d)/(R_s + (D-M))\}(D-M).$$

As the terms other than the correction terms have been calculated, such known values are applied to the replaced formula (4) to obtain an amount of the correction term M (step S12). In this way, through steps S10 to S12, the functional parameters $\Delta x/\Delta Fi$, $\theta$, $\Delta\theta/\Delta Fi$, D, M, and (CX, CY) are calculated at each X-ray radiation angle $\theta$.

The image processor 56 then updates the values of the functional parameters, which are stored in the image memory 54, with the newest ones calculated this time (step S13). This can calibrate the parameters necessary for 3D image reconstruction.

After the foregoing calculation for the structural analysis and calibration, the image processor 56 determines, responsively to operator's manipulation information, whether or not it is necessary to output, through printing or display, the constant parameters $R_d$, $R_s$ and B1 and the functional parameters $\Delta x/\Delta Fi$, $\theta$, $\Delta\theta/\Delta Fi$, D, M and (CX,CY), which have been calculated (step S14). If it is determined that such output is necessary, the image processor 56 prints or displays the amounts of such parameters (step S15).

After the parameter output is completed or when such output is unnecessary, the processing is continued by the computer 57. This computer determines if imaging of a patient is need interactively with the operator (step S16). When the imaging is not required, the processing is completed. In this way, the simplified type or detailed type of calibration as well as the structural analysis of the imaging space is completed.

Meanwhile, when it is required to image the jaw of a patient, 3D image reconstruction is performed which allows an accurate understanding of actual positions of a patient's tooth row located in the imaging space. In this reconstruction outlined in FIG. 20, components are projected along the oblique radiation directions of the X-ray beams, which view the X-ray tube 31 obliquely from each point of the 3D referential tomographic plane SS. This provides accurate identification of three-dimensional positions of an object being imaged (actual object), such as a tooth row. Hereinafter, imaging which involves processes for the positional identification will now be described.

<Imaging of Object>

Referring back to FIG. 5, processing performed cooperatively by the controller 57 and the image processor 56 will now be described. This processing includes, as described before, data acquisition by scanning, reconstruction of a referential panoramic image which is a pre-process, and production of 3D autofocus image (surface image) which is a main process, and display and/or measurement based on various modes which use the 3D autofocus images.

(Data Acquisition and Reconstruction of Referential Panoramic Image)

Figure 5:
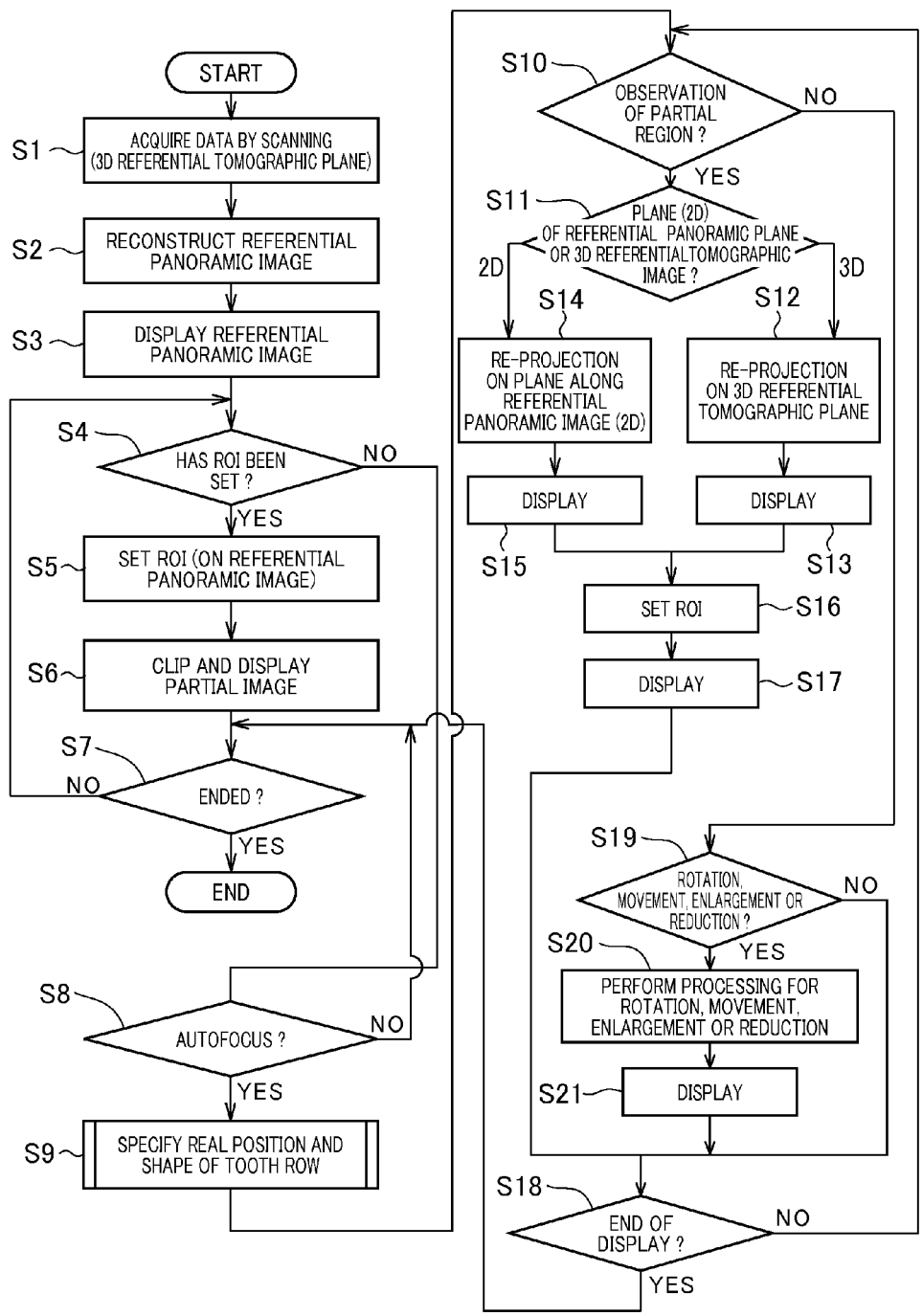
FIG. 5 is a flowchart showing an outline of processing for imaging performed cooperatively by a controller and an image processor provided in the panoramic imaging apparatus.

After finishing various imaging preparations such as positioning of an object (patient) P, the controller 57 responds to an operator's command given through the operation device 58 to command scanning for acquiring data (in FIG. 5, Step S1). By this command, the rotary drive mechanism 30A, the movement mechanism 30B, and the high-voltage generator 41 are commanded to be driven according to a predetermined control sequence. As a result, during rotation of the pair of the X-ray tube 31 and the detector 32 around the jaw of the object P, the X-ray tube 31 radiates a pulsed or a continuous-wave X-ray at intervals or continuously. As described before, the pair of the X-ray tube 31 and the detector 32 is driven to rotate under a given drive condition so as to optimally focus on the 3D referential tomographic plane SS (refer to FIG. 6). The X-ray radiated from the X-ray tube 31 thus is transmitted through the object P to be detected by the detector 32. Accordingly, the detector 32 outputs, for example, at a rate of 300 fps, digital frame data (i.e., pixel data) in which amounts of X-ray transmission are reflected. The outputted frame data are temporarily stored in the buffer memory 53.

After the command for the scanning, the next command for the processing is provided to the image processor 56. The image processor 56 reads, from the look-up table LUT, every frame number Fi for each X-ray radiation direction, the newest amounts of the radiation angle, the angular speed curve, the rotation center–referential tomographic plane distance D, and the correction term M, and uses the read amounts to correct the 3D referential tomographic plane SS. This enables the plane SS to be positionally, part by part, changed in the front-back direction, so that the plane is smoothed (step S2A). The image processor 56 reconstructs a referential panoramic image $PI_{st}$ based on the shift & add process based on the tomosynthesis technique according to spatial positions in the corrected 3D referential tomographic plane SS, and the respective pixel values of the reconstructed image are stored (step S2B).

In this reconstruction process, the reconstructed image is multiplied by coefficients such that, similarly to the conventional, longitudinal and lateral enlargement factors at the center of the anterior teeth become equal to each other.

Figure 21:
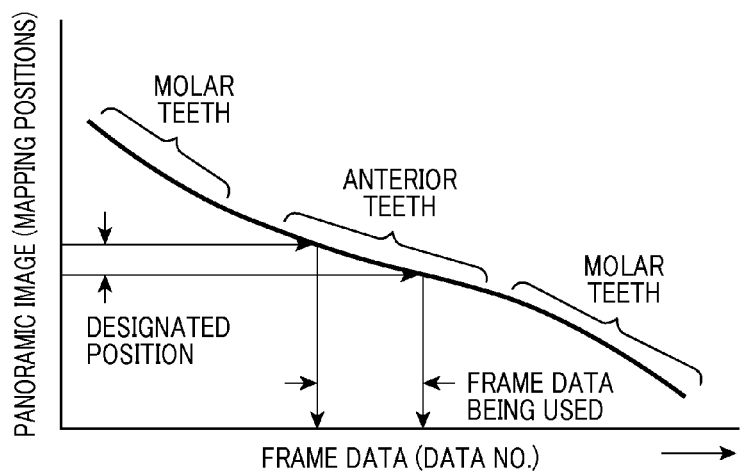
FIG. 21 is a graph explaining a relationship between frame data and mapping positions of the frame data to produce a panoramic image.

Although how to reconstruct an image is known, this will now be described a little. A set of frame data used for the reconstruction is obtained from a mapping characteristic which shows, as shown in FIG. 21 for example, mapping positions in the lateral direction of a panoramic image and a set of frame data which will be subjected to mutual addition for producing an image at the mapping positions. A curve showing this mapping characteristic consists of two curved portions which are steeper depending on molar teeth on both sides in the frame data direction (abscissa axis) and a curved portion which is gentler than those of the two curved portions for the molar teeth depending on the anterior teeth. As shown, in this projection characteristic is used to designate a desired mapping position in the lateral direction of the panoramic image. Based on this designation, the set of frame data used to produce an image at the designated mapping position and amounts of shift (i.e. degrees of overlapping necessary frame data, which is a gradient of the curve) are designated. The designated frame data (i.e., pixel values) are shifted in accordance with the designated shift amounts to be overlapped on one another and added to each other, thus providing data of a longitudinally extending image at the designated mapping position. By repeating the designation of mapping positions and shift & add calculation through the entire range in the lateral direction of the panoramic image, it is possible to reconstruct the referential panoramic image $PI_{st}$ which focuses on the 3D referential tomographic plane SS.

Figure 22:
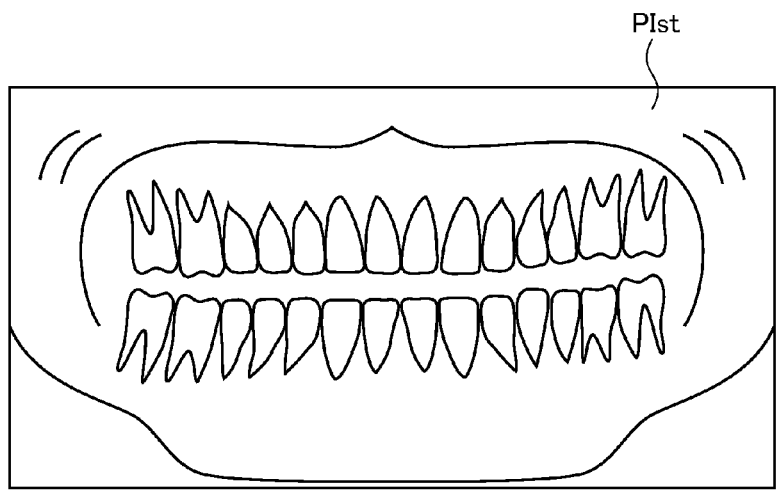
FIG. 22 is a view pictorially showing an example of a reference panoramic image.

The image processor 56 then displays the constructed referential panoramic image $PI_{st}$ on the monitor 60 (step S3), of which example is pictorially shown in FIG. 22.

Since the referential panoramic image $PI_{st}$ is an image produced by shifting the frame data to be overlapped on one another and mutually adding them, this image is two-dimensional rectangular. Longitudinal and lateral distortion at the anterior teeth in this image $PI_{st}$, which is due to a difference of the enlargement factor in the longitudinal and lateral direction, is improved to some extent similarly to the conventional, because the image is multiplied by the coefficients so as to make the longitudinal and lateral enlargement factors equal to each other at the center of the anterior teeth. However, as advancing to and through the molar teeth, the longitudinal and lateral ratios of teeth become shifted from the correct ones. That is, the molar teeth are depicted to be less in size than the real size thereof. In many conventional cases, doctors are obliged to suffer such panoramic images with distortion.

(Setting ROI on Referential Panoramic Image)

Then, the image processor 56 determines whether or not the operator uses the operation device 58 to set a ROI (a region of interest) on the referential panoramic image $PI_{st}$ (step S4). For example, the ROI shows a rectangular partial region in which the interpreter has a special interest. The ROI is not always limited to rectangular. In addition, the ROI can be set on the panoramic image automatically focused, which will be described later.

Figure 23:
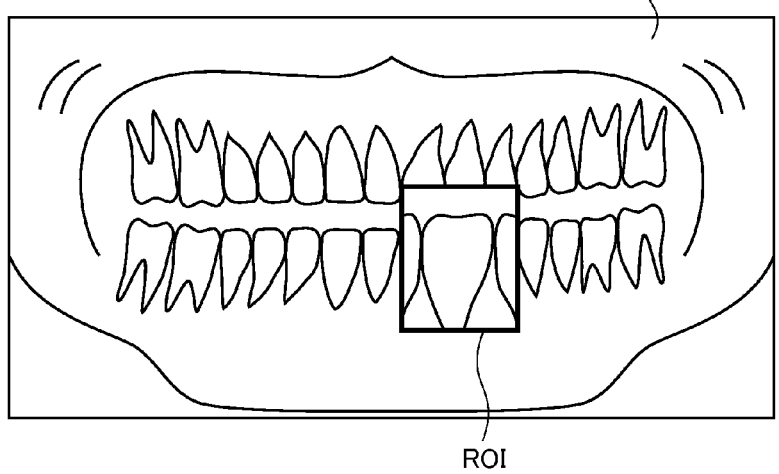
FIG. 23 is a view pictorially showing an example of the reference panoramic image on which a ROI is set.

When the determination at step S4 is YES, the image processor 56 responds to operational information from the operator to set the ROI on the referential panoramic image $PI_{st}$ (step S5). Then a partial image, which corresponds to the partial region sectioned by the ROI, is clipped out, and the partial image is displayed in a magnifying scale for example (step S6). For example, as shown in FIG. 23, this partial image is displayed in a superposed manner on the original referential panoramic image $PI_{st}$. Alternatively, one or more partial images can be displayed by being mapped in a template in which blocks arranged to pictorially depict partial tooth rows in both the upper and lower teeth are arranged in a predetermined order.

Then the image processor 56 determines whether or not the processing should be ended. This determination depends whether or not there is operational information from the operator (step S7). When it is determined to continue the processing (NO at step S7), the processing is returned to step S4 for repetition of the foregoing steps. In contrast, when the determination shows completion of the processing, the processing shown in FIG. 5 is ended.

Meanwhile, when the determination at step S4 is NO, that is, when the ROI will not be set, the image processor 56 proceeds to the next step. Practically, it is determined based on operational information from the operator whether or not production of a 3D autofocus image is performed as a main process (step S8). If it is determined that this production will not be performed (NO at step S8), the processing is made to return to step S7 to determine the end of the processing similarly as described.

(Specification of Position of Optimally Focused Section)

In contrast, when it is determined that production of the 3D autofocus image is desired (YES at step S8), the processing proceeds to a subroutine provided at step S9. The processing executed at step S9 provides one of the features of the present invention, which is automatic identification of the real position and shape of a tooth row. In the identification, changes of the rotation center RC are taken into consideration and longitudinal distortion of the tooth row is corrected in oblique projection directions $DR_x$ which are directed from respective pixels to the X-ray focus of the X-ray tube 31.

Figure 24:
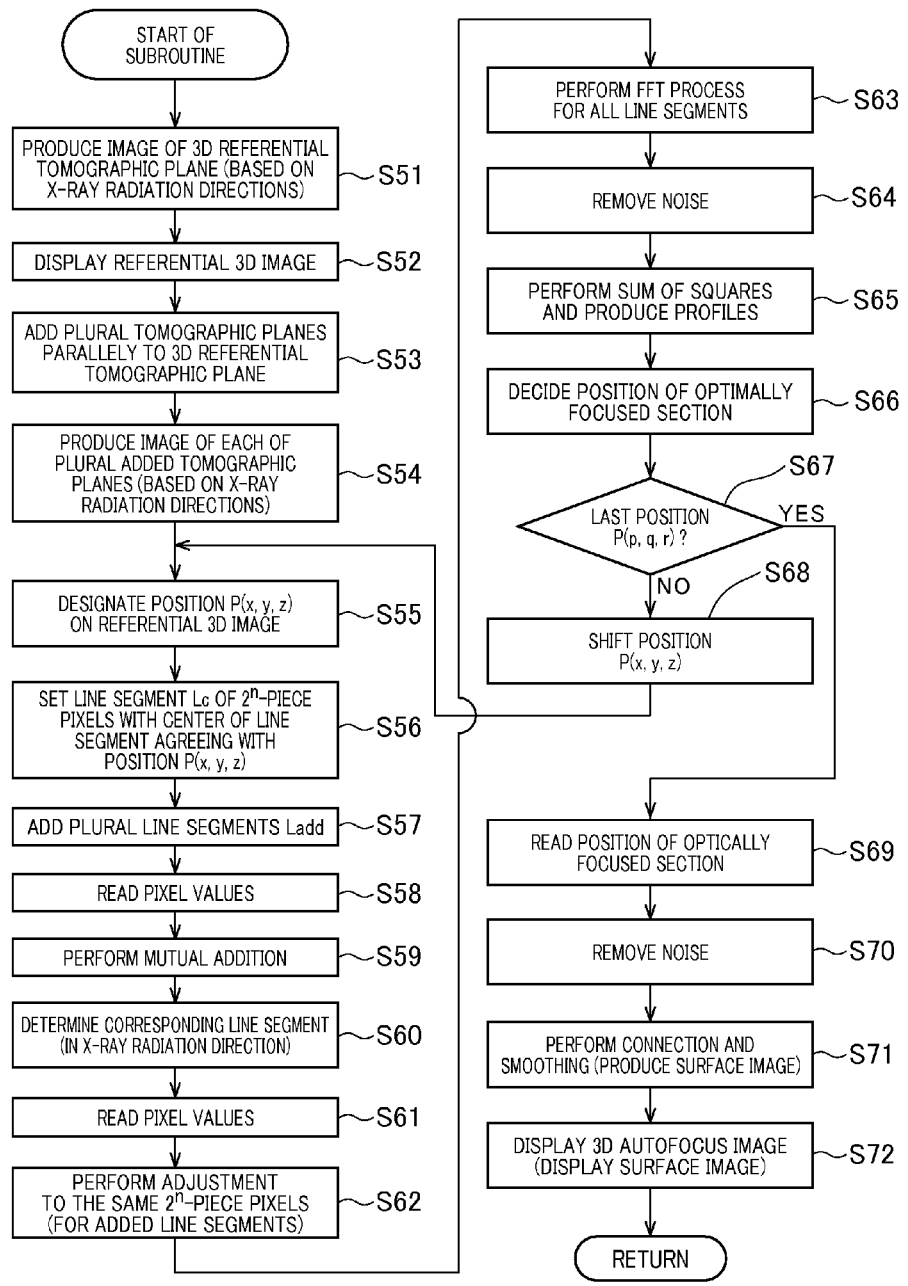
FIG. 24 is a flowchart outlining a process to identify the real positions and shapes of teeth, which is performed by an image processor.

FIG. 24 shows processing of the subroutine for such identification.

First, the image processor 56 coordinate-converts, only once, the referential panoramic image $PI_{st}$ (rectangular) onto a curved plane parallel with the 3D referential tomographic plane SS (a curved plane), thus producing a 3D panoramic image. The image processor then reads, from the look-up table LUT, every frame number Fi, both the radiation angle θ and the newest values of the coordinate position (CX, CY) of the rotation center. The image processor further extends the direction from the coordinate position (CX, CY) by an amount of the X-ray–rotation center distance $R_s$, so that the position of the X-ray tube 31 is calculated every X-ray radiation angle θ. Oblique projection directions $DR_x$ are then set which are always oriented from the respective pixels of the produced 3D panoramic image to the X-ray focus of the X-ray tube 31. After this, calculation for changing tomographic planes is performed to obtain frame data, and the obtained frame data are projected to the 3D referential tomographic plane SS through coordinate conversions along each of the projection directions $DR_x$. This provides a projected image along the curved 3D referential tomographic plane SS (step S51). The pixel values of this projected image are stored in the image memory 54.

Figure 25:
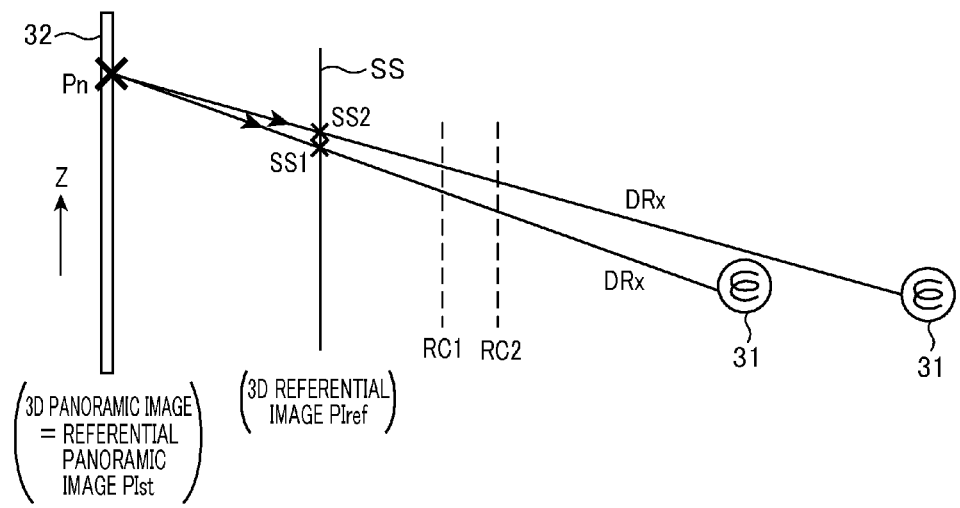
FIG. 25 is a view explaining a difference between angles from the same position in the Z-axis direction on a 3D panoramic image to the X-ray tube, which angles are caused by positional changes in the rotation center of the pair of the X-ray tube and the detector.

The projection is performed, as shown in FIG. 25, along each of the oblique projection directions $DR_x$ directed to the rotation center RC(RC1, RC2), that is, the position where the X-ray tube 31 is present. When referring to the example in FIG. 25, a pixel located at a position Pn in the height direction (the Z-axis direction) of the 3D panoramic image will be projected to different positions SS1 and SS2 on the image of the 3D referential tomographic image SS, which is due to differences of positions at each of which the X-ray tube 31 is located.

The projection image produced by this projection is called a 3D referential image $PI_{ref}$ in the present embodiment. This 3D referential image $PI_{ref}$ is produced by oblique projection with consideration of characteristics of the foregoing enlargement factor, in which the oblique projection is performed every pixel of the referential panoramic image $PI_{st}$. By this oblique projection, enlargement of teeth belonging to the anterior teeth, which have large enlargement factors, is corrected to have real sizes thereof, while enlargement of teeth belonging to the molar teeth on both sides of the tooth row, which have small enlargement factors, is also corrected to have real sizes thereof. Hence, in the 3D referential image $PI_{ref}$, the teeth are depicted with their real sizes and have no or less distortion which is due to the largeness of the enlargement factors caused by the moved rotation center RC during the scanning. However it should be noted that this 3D referential image PIref is produced on the assumption that the tooth row is present at and along the 3D referential tomographic plane SS. It is rare that actual teeth are present at and along the plane SS, so that it is required to perform further processing to identify the real spatial positions and shapes of the teeth.

Figure 26:
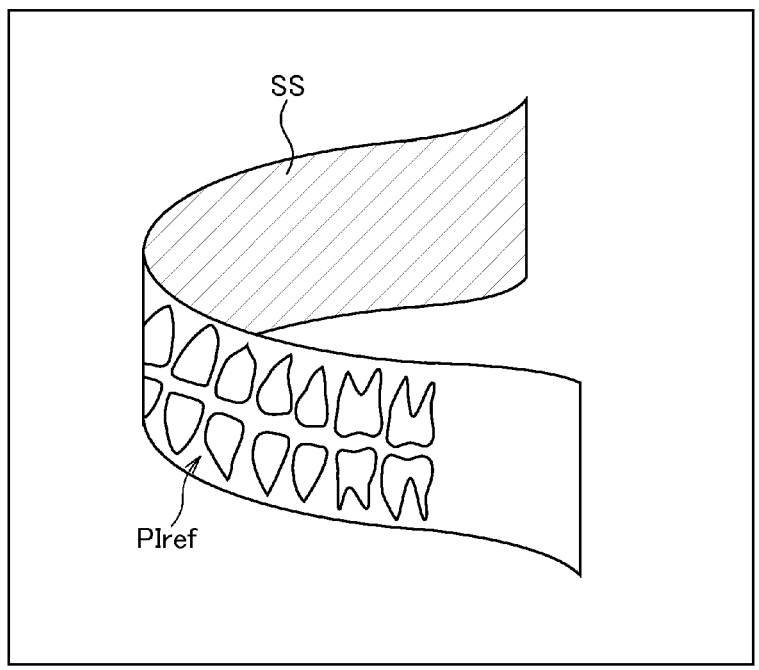
FIG. 26 is a view pictorially showing an example of a 3D reference image.

The image processor 56 displays the 3D referential image $PI_{ref}$ on the monitor for operator's reference (step S52). This is shown in FIG. 26.

Figure 27:
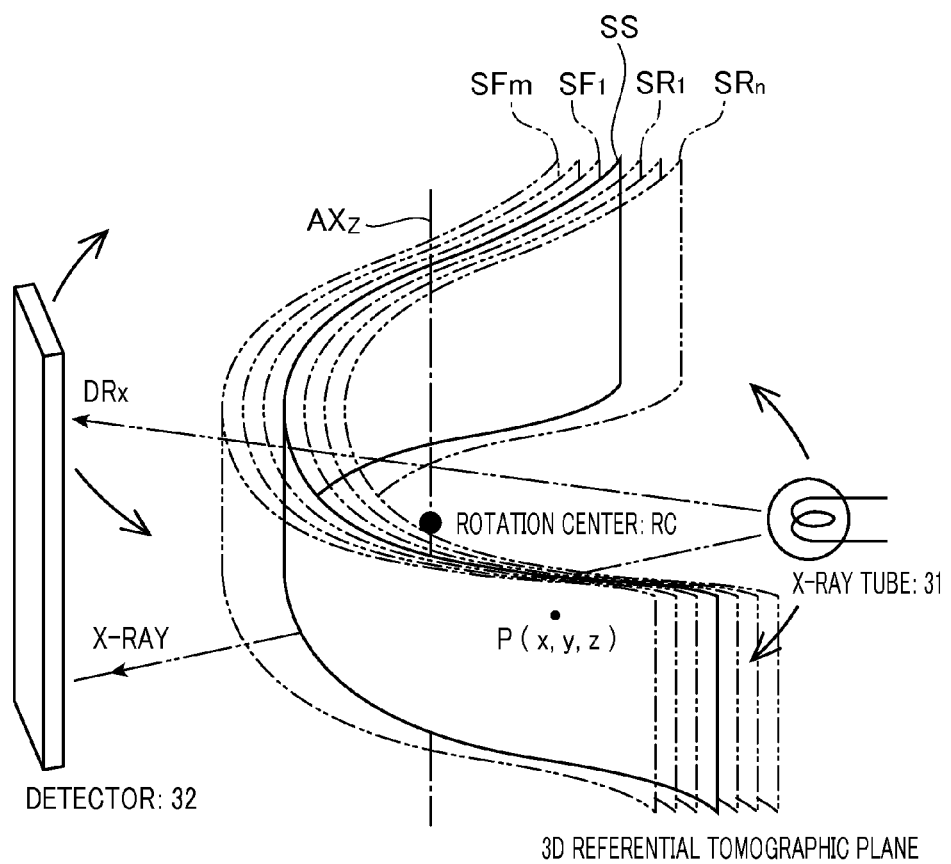
FIG. 27 is a perspective view explaining a plurality of parallel tomographic planes added to a 3D referential tomographic plane.
Figure 28:
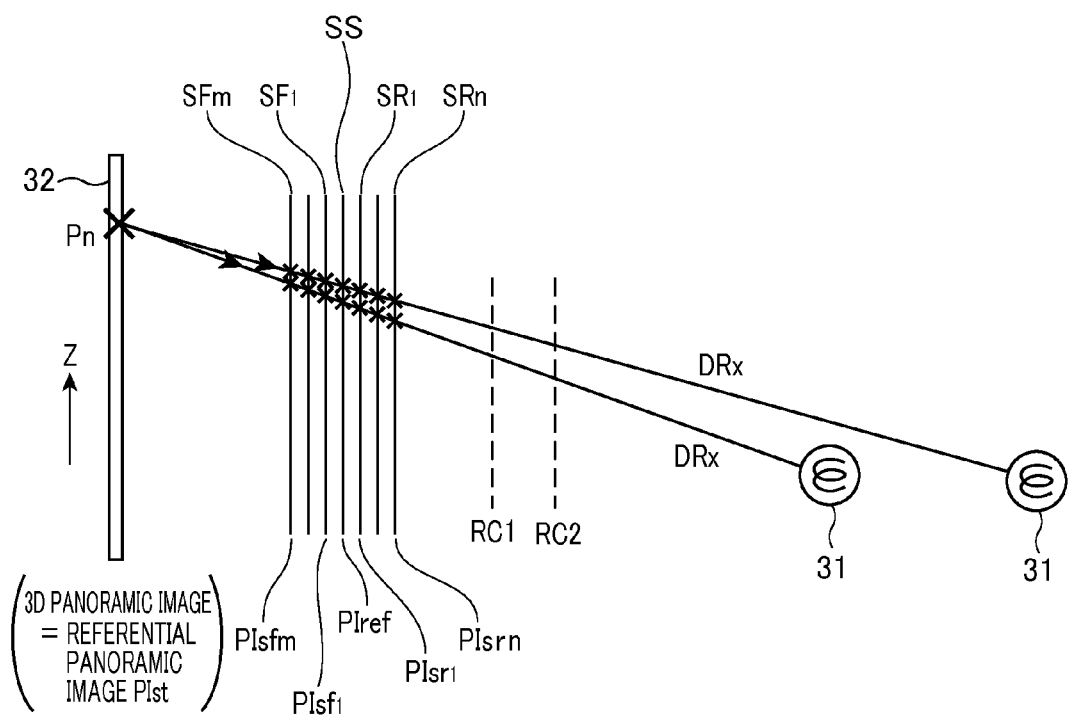
FIG. 28 is a view explaining differences of positions projected on the plurality of tomographic planes, which positions are obtained when the same Z-axial position on a 3D panoramic image is projected to portions of the X-ray tube, wherein the positional differences are caused by positional changes in the rotation center of the pair of the X-ray tube and the detector.

The image processor 56 then adds a plurality of curved and parallel tomographic planes (sections) to the 3D referential tomographic plane SS (step S53). This is shown in FIG. 27. As shown, a plurality of tomographic planes are added to the 3D referential tomographic plane SS such that such tomographic planes are set before and after the plane SS respectively in the X-ray radiation directions $DR_x$ (i.e., the depth direction of the tooth row). Each of these plurality of tomographic planes is also partially corrected in positions in the front-back directions hereof, in accordance with amounts corrected by the rotation center–referential tomographic plane distance D and the correction term M which have been applied to the 3D referential tomographic plane SS.

By way of example, plural tomographic planes $SF_m$-$SF_1$ are located on the front side of the 3D referential tomographic plane SS at intervals of D1 (for example, 0.5 mm), while plural tomographic planes $SR_1$-$SR_n$ are located on the rear side of the plane SS at intervals of D2 (for example, 0.5 mm). The intervals D1 and D2 may be equal to each other or different from each other. In addition, the number of tomographic planes to be added may be one on the front and rear sides of the plane SS respectively (i.e., m, n=1) or may be one or plural on either the front side or the rear side of the plane SS.

Incidentally, position data indicative of the virtually added tomographic planes $SF_m$-$SF_1$ and $SR_1$-$SR_n$ are previously stored in the ROM 61 together with positional data of the 3D referential tomographic plane SS, so that the image processor 56 can perform the addition through reading of the positional data and loading them into a work area of the image processor 56. The heights of the tomographic planes $SF_m$-$SF_1$, SS, and $SR_1$-$SR_n$ are decided appropriately in consideration of the maximum gradient of the X-ray radiation directions $DR_x$ and the height of the tooth row. Every time the identification processing is performed, the positions (the intervals D1, D2) of the tomographic planes to be added and the number thereof may be changed interactively.

Further, similarly to the processing at step S51, the image processor 56 calculates projection directions $DR_x$ depending on changes in the coordinate positions (CX, CY) of the rotation center RC. And along the calculated projection directions $DR_x$, the image processor 56 projects the referential panoramic image $PI_{st}$ onto each of the added tomographic planes $SF_m$-$SF_1$ and $SR_1$-$SR_n$ by obtaining frame data through calculation of changes of tomographic planes and coordinate-changing the obtained frame data (step S54). As a result, images projected to the respective added tomographic planes $SF_m$-$SF_1$ and $SR_1$-$SR_n$ are produced. The pixel values of such projection images are stored in the image memory 54.

In the present embodiment, the produced projection images are referred to as 3D added images $PI_{sfm}$, $PI_{sf1}$, $PI_{sr1}$, $PI_{srn}$. Each of these 3D added images $PI_{sfm}$, ..., $PI_{sf1}$, $PI_{sr1}$, ..., $PI_{srn}$ is also produced by the oblique projections performed through the individual pixel positions of the referential panoramic image PIst, in which the oblique projections take into account of the foregoing differences in the longitudinal enlargement factors. This is exemplified in FIG. 28, in which the same pixel existing at a position Pn in the height direction of a 3D panoramic image (i.e., the Z-axis direction) is projected onto different positions on the respective 3D added images $PI_{sfm}, \ldots, PI_{sf1}, PI_{sr1}, \ldots, PI_{srn}$, which are due to differences in positions where the X-ray tube 31 is located.

Hence, the teeth depicted in the 3D added images $PI_{sfm}, \ldots, PI_{sf1}, PI_{sr1}, \ldots, PI_{srn}$ are depicted with their real sizes and distortion due to the largeness of the enlargement factors, which is due to the movement of the rotation center RC during the scanning, is removed or suppressed from such 3D added images. It should be noted however that the 3D added images $PI_{sfm}, \ldots, PI_{sf1}, PI_{sr1}, \ldots, PI_{srn}$ are produced on the assumption that the tooth row is present at and along each of the 3D added images $PI_{sfm}, \ldots, PI_{sf1}, PI_{sr1}, \ldots, PI_{srn}$.

As a modification, the plural 3D added images $PI_{sfm}, \ldots, PI_{sf1}, PI_{sr1}, \ldots, PI_{srn}$ thus produced can be displayed on the monitor 60 as three-dimensional images as they are or displayed on the monitor 60 as rectangular two-dimensional images produced through coordinate conversion.

The image processor 56 then designates an initial position P(x, z) on the 3D referential image $PI_{ref}$, that is, the 3D referential tomographic plane SS (step S55; refer to FIG. 29(A)). After this, the image processor designates a line segment Lc of a given length centering the designated position P(x, y, z) on the 3D referential image $PI_{ref}$ (step S56; refer to FIG. 29(B)). This line segment Lc has the given length corresponding to $2^n$ pieces (n=1, 2, 3, . . . ; for example 128 pieces). As modifications, the line segment Lc can be drawn along a part of the curved 3D referential tomographic plane SS so that the lien segment is curved or can be drawn in a limited range regarded as being liner.

Then the image processor 56 virtually adds plural line segments Ladd on the upper and lower sides of the designated line segment Lc(x, y, z) on the image, respectively, in which the plural line segments $L_{add}$ have the same length as that of the line segment Lc(x, y, z) (step S57; refer to FIG. 29(C)).

The image processor then reads, from the image memory 54, the pixel values $P_{ij}$ of respective $2^n$-piece pixels composing each of the foregoing line segment Lc and plural line segments $L_{add}$, and assigns the read pixel values to the respective line segments (step S58). The pixel values $P_{ij}$ have been already acquired and stored through the foregoing steps S51 and S54.

The image processor then mutually add the pixel values $P_{ij}$ of the pixels corresponding to the line segment Lc and line segments $L_{add}$ to obtain $2^n$-piece pixel values $P_{ij}*$ that composes the line segment Lc(x, y, z), the 2n-piece pixel values $P_{ij}*$ being for a frequency analysis (step S59; refer to FIG. 29(D)). This addition makes it possible to reduce statistical noise in a later-described frequency analysis of changes in the pixel values, even if the pixel values of the line segment Lc(x, y, z) originally contain the statistical noise.

Figure 29:
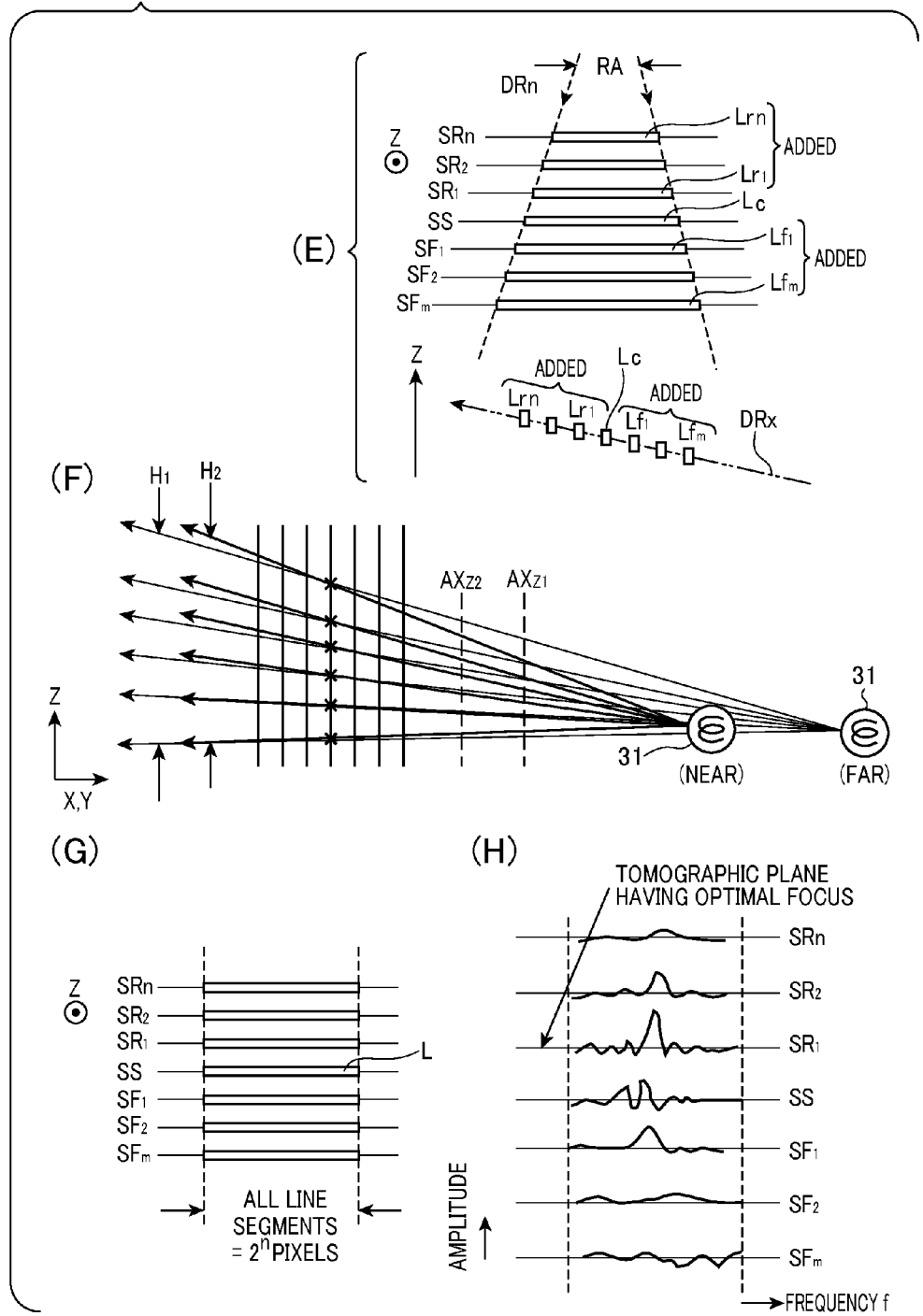
FIG. 29(1) is a view explaining, together with FIG. 29(2), the process to identify optimally-focused tomographic planes for each of positions on the 3D reference image.

Then, on each of the 3D added images $PI_{sfm}, \ldots, PI_{sf1}$ and $PI_{sr1}, \ldots, PI_{srn}$, the image processor 56 calculates the spatial positions of the line segments $L_{fm}$-$L_{f1}$ and $L_{r1}$-$L_{rn}$ that face the line segment Lc(x, y, z) designated currently on the foregoing 3D referential image $PI_{ref}$ in the X-ray radiation direction $DR_x$ passing through the currently designated position P(x, y, z) (step S60; refer to FIG. 29 (E)). In this case, the current center position P(x, y, z) and the length of the line segment Lc, and the rotational positions of the X-ray tube 31 during the scanning are known. Hence, it is possible to calculate an X-ray radiation range RA which is fan-shaped when being viewed in the Z-axis direction, in which this range RA is formed by connecting each of both ends of the line segment Lc to the X-ray tube 31. As a result, as long as the position P(x, y, z) is designated, the special positions of the line segments $L_{fm}, \ldots, L_{f1}$ and $L_{r1}, \ldots, L_{rn}$ limited by the X-ray radiation range in compliance with the designated position can also be designated by the image processor.

The process of step S60 to designate the position the position P(x, y, z) on the 3D referential image $PI_{ref}$ is repeated until the same process for all the positions thereon is completed. Hence, in terms of effective X-ray radiation, the X-rays radiated from the X-ray tube 31 whose position comes near and farer transmit through the virtually set tomographic planes $SF_m$-$SF_1$, SS, and $SR_1$-$SR_n$ within a range of H1 to H2 (a Z-axial range) in the fan shape (refer to FIG. 29 (F)). With consideration this fact, the tomographic planes $SF_m$-$SF_1$, SS and $SR_1$-$SR_n$ themselves may be horseshoe-shaped sections having heights which change in every scanning direction and being parallel with each other.

When the line segments $L_{fm}$-$L_{f1}$ and $L_{r1}$-$L_{rn}$ have been set as above, the image processor 56 reads pixel values $P_{ij}*$ of such line segments from the image memory 54 (step S61).

As shown in FIG. 29(E), since the X-ray tube 31 has a punctate X-ray source, the X-ray radiation range RA becomes a fan shape (when being viewed along the Z-axis direction). Hence, the pixels of each of the line segments $L_{fm}$-$L_{f1}$ and $L_{r1}$-$L_{rn}$ are not $2^n$-pieces in number. Thus the image processor 56 multiplies each of the line segments $L_{fm}$-$L_{f1}$ and $L_{r1}$-$L_{rn}$ by a coefficient depending on the distances D1 and D2 in such a manner that the number of pixels of each of the added line segments $L_{fm}$-$L_{f1}$ and $L_{r1}$-$L_{rn}$ becomes equal to the number of pixels, $2^n$, of the referential line segment Lc(x, y, z). Accordingly, as pictorially shown in FIG. 29(G), all the line segments $L_{fm}$-$L_{f1}$, Lc and $L_{r1}$-$L_{rn}$ are formed to be parallel with each other and to have the same number of pixels, $2^n$.

After this, the image processor 56 applies a frequency analysis to changes in the values of pixels of each of all the line segments $L_f$-$L_{fm}$, Lc, and $L_{r1}$-$L_{rn}$ (step S63). Thus, as shown in FIG. 29(H), as to the line segments $L_{fm}$-$L_W$, Lc and $L_{r1}$-$L_{rn}$, there are provided analyzed results consisting of an abscissa axis showing frequencies and a vertical axis showing Fourier coefficients (amplitudes).

In the present embodiment, the frequency analysis is performed using fast Fourier transformation, but wavelet transformation may be adopted as such frequency analysis. Moreover, instead of such frequency analysis, a Sobel filter to calculate the first derivation for edge extraction can be used for the equivalent process to the above. In using this filter, the position of a tomographic plane which provides an edge with a maximum filtered value can be regarded as an optimally focused position.

Figure 30:
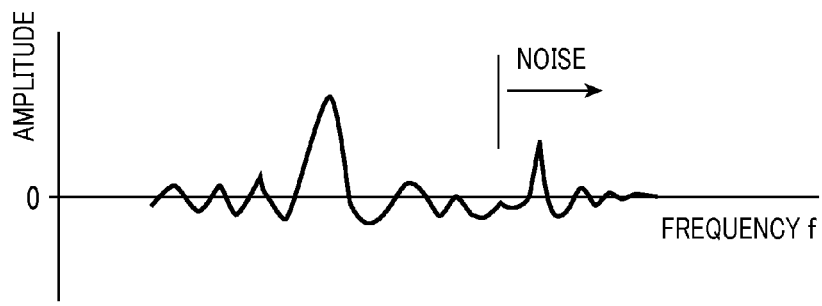
FIG. 30 is a graph exemplifying a frequency analysis result in an identification process for the optimally focused positions.
Figure 31:
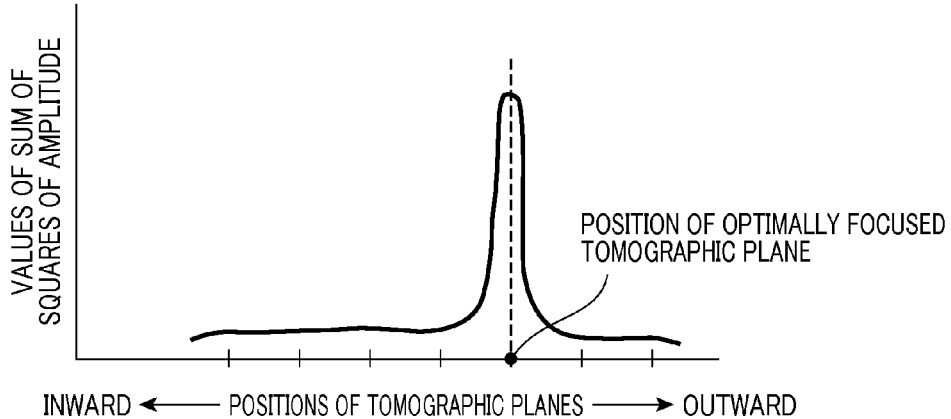
FIG. 31 is a graph exemplifying the position of an optimally focused tomographic plane obtained in the identification process for the optimally focused positions.

The image processor then removes noise from the frequency analyzed results for all the line segments $L_{f1}$-$L_{fm}$, Lc, and $L_{r1}$-$L_{rn}$ (step S64). FIG. 30 exemplifies the frequency analyzed characteristic for one line segment. Coefficients of frequency components which belong to a given frequency range beyond a maximum frequency of the analysis are removed, with coefficients of the remaining high-frequency components adopted. The reason for such removal is that frequency components which are present in the given frequency range beyond the maximum frequency provide noise components.

Further the image processor 56 calculates sums of squares for the coefficients of the frequency analyzed characteristic of each of the line segments, and produces a profile having a vertical axis to which the values of sums of squires are assigned and an abscissa axis to which the positions of the respective tomographic planes $SF_m$-$SF_1$, SS, and $SR_1$-$SR_n$ are assigned, where the X-ray radiation direction DRx passing through the initial position P(x, y, z)=P(0, 0, 0) passes through the positions of such tomographic planes (step S65). This profile is exemplified in FIG. 31. In this profile, the positions of the tomographic planes mean the positions the plural tomographic planes $SF_1$-$SF_m$, SS, and $FR_1$-$FR_n$ in the X-ray radiation direction $DR_x$ (i.e., the depth direction of the tooth row).

Figure 32:
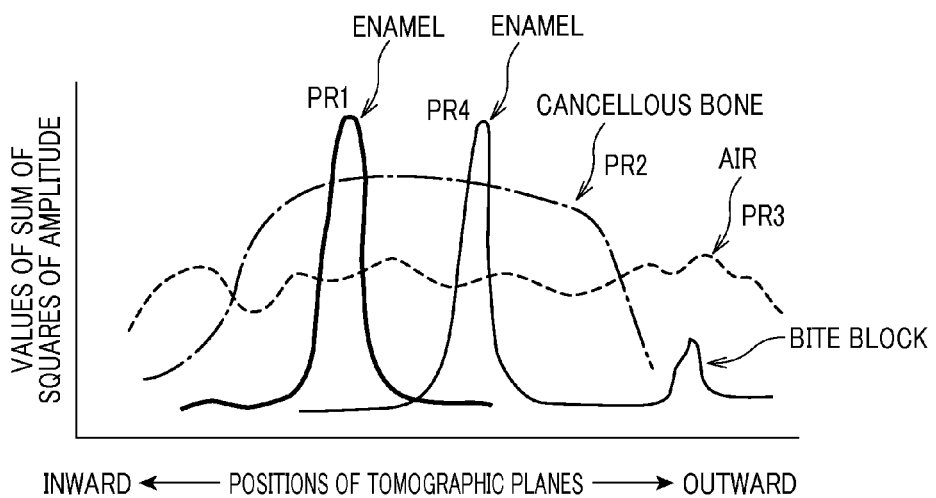
FIG. 32 is a graph exemplifying frequency characteristic patterns changing depending on tomographic plane positions.
Figure 33:
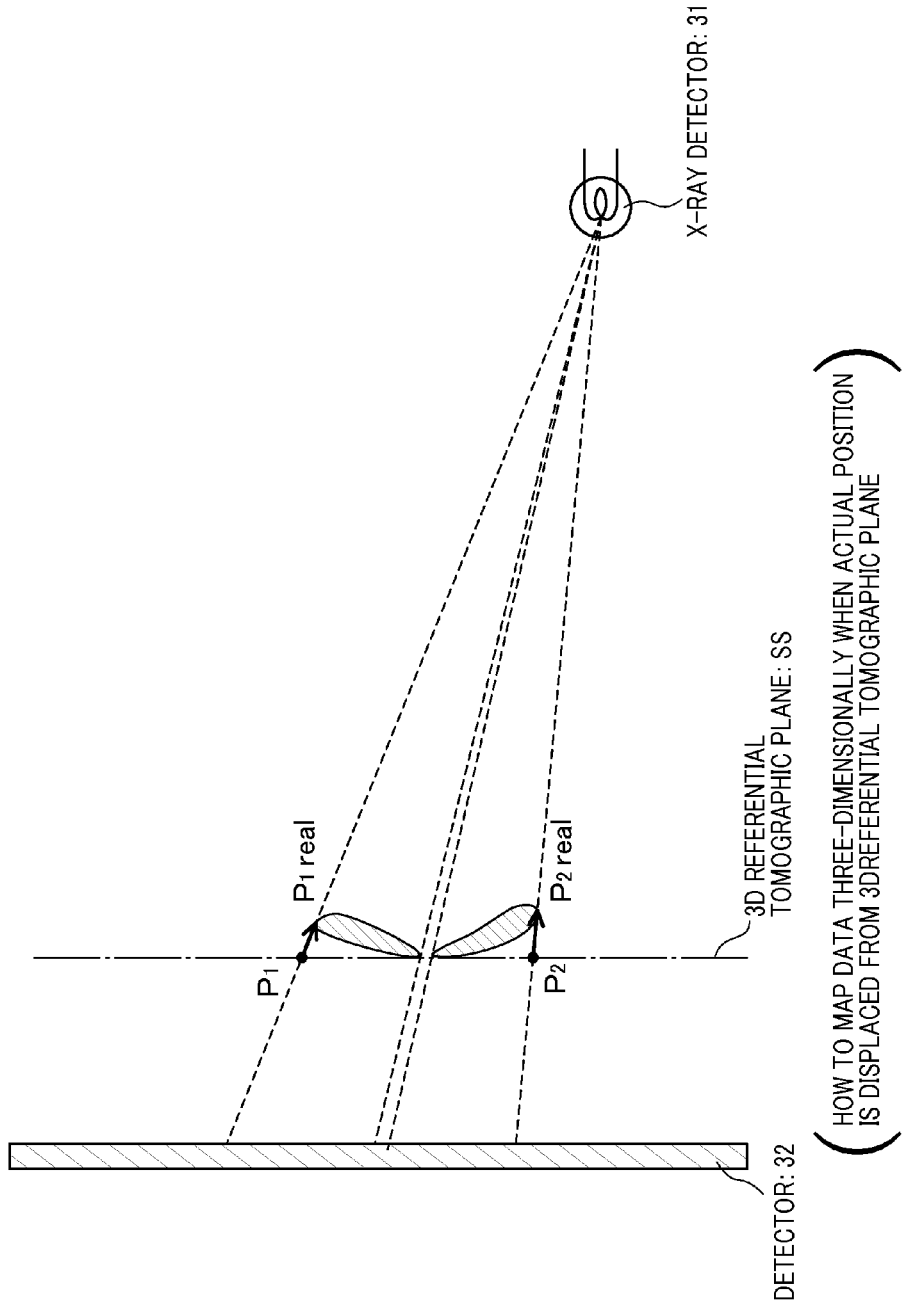
FIG. 33 is a view explaining a state where the real positions of teeth are deviated from the 3D referential tomographic plane.
Figure 34:
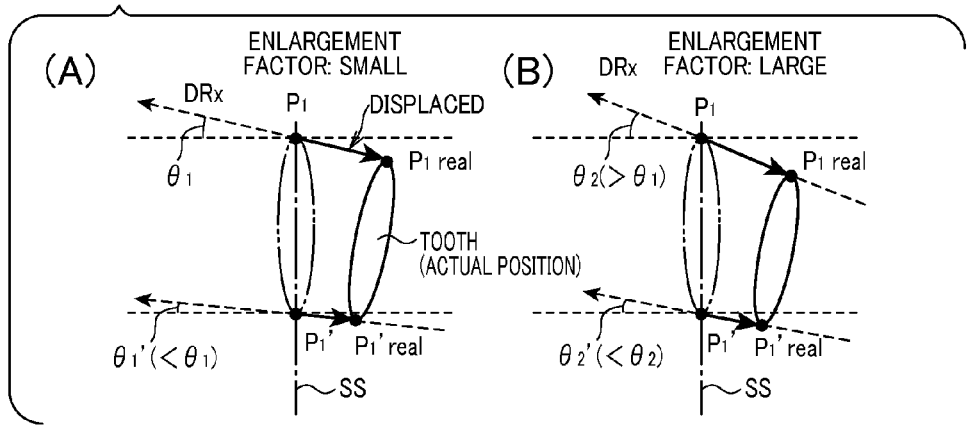
FIG. 34 is a view explaining a state where a tooth is shifted from the position of the 3D referential tomographic image to its real position depending on the value of an enlargement factor.
Figure 35:
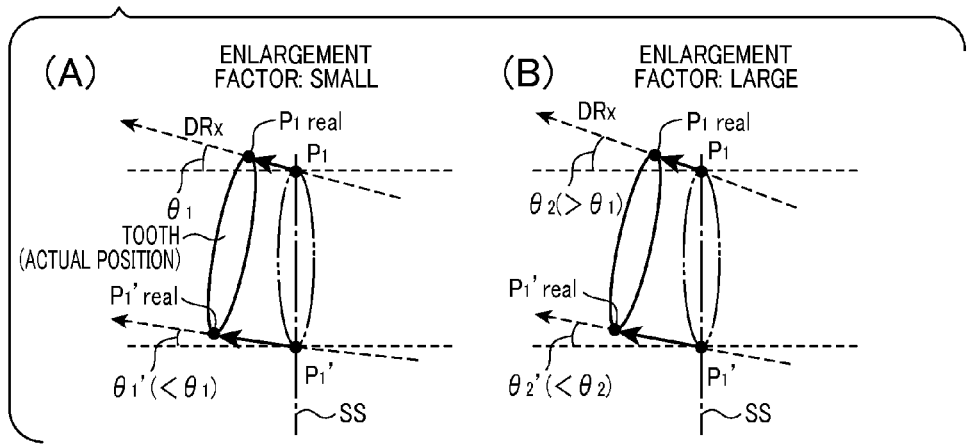
FIG. 35 is a view explaining a state where a tooth is shifted from the position of the 3D referential tomographic image to its real position depending on the largeness of an enlargement factor.

FIG. 32 exemplifies, as typical patterns, a plurality of types of profiles PR1, PR2, PR3 and PR4 respectively showing substances composed of enamel, cancellous bone, air and bite blocks. If there is a substance composed of enamel, i.e., tooth, anywhere in the X-ray radiation direction $DR_x$ that passes through the currently designated position P(x, y, z), the profile PR1 has a sharp peak. If there is cancellous bone in that X-ray radiation direction $DR_x$, the profile PR2 has a gentle convex curve. Similarly, if there exists only air in that X-ray radiation direction $DR_x$, the profile PR3 tends to show a curve having no specific peaks. Moreover, when the bite block is present in that X-ray radiation direction $D_{Rx}$, the profile PR4 exhibits two sharp peaks. Of such two peaks, one appearing inward (on the X-ray tube side) in the X-ray radiation direction $DR_x$ shows that the substance thereat is enamel, while the other appearing outward (on the detector side) shows that the substance thereat is the bite block. Data indicating the patterns of the profiles shown in FIG. 32 are previously stored, as reference profiles, in the ROM 61 in the form of a reference table.

Hence, the image processor 56 refers to the reference table to specify an optimum focused position of the tooth in the X-ray radiation direction $DR_x$ passing through the currently designated position P(x, y, z) (step S66).

That is, a pattern recognition technique is used to determine that the profile obtained in the last step S65 corresponds to which of the reference profiles PR1-PR4.

First, when the obtained profile is the reference profile PR2 or PR4, such a profile is withdrawn from the consideration. In contrast, when the obtained profile corresponds to the reference profile PR1 (i.e., enamel), it is identified that the section position showing its peak, i.e., the position of any of the plural tomographic planes $SF_1$-$SF_m$, SS, $FR_1$-$FR_n$, is optimally focused. Moreover, when the obtained profile is fit to the reference profile PR4, it is also identified that an inward sectional position expressing a peak (a sectional position showing enamel on the X-ray tube side), in other words, the position of any of the plural tomographic planes $SF_1$-$SF_m$, SS, $FR_1$-$FR_n$, is optimally focused.

By the foregoing specifying steps, it is identified that a portion of the tooth depicted at the currently designated position P(x, y, z) is actually present at which position in the depth direction. In effect, a tooth portion depicted on the 3D referential image $PI_{ref}$ along the 3D referential tomographic plane SS may be present on the front or rear sides of the plane SS. The real position of the tooth portion in the imaging space is specified precisely by the foregoing specifying steps. In other words, it can be understood that a tooth portion depicted on the 3D referential image $PI_{ref}$ under the condition that the tooth portion is on and along the 3D referential tomographic plane SS is shifted to its real special position by the foregoing specifying steps.

Figure 36:
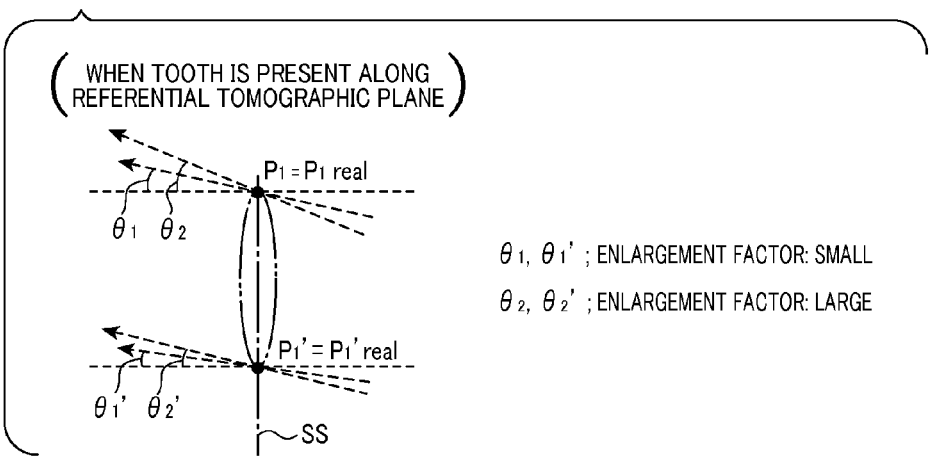
FIG. 36 is a view explaining a state where a tooth is shifted from the position of the 3D referential tomographic image to its real position depending on the largeness of an enlargement factor.

As a result, as shown in FIGS. 33-36, every time the position P(x, y, z) is designated, a position P1 on the 3D referential tomographic plane SS (i.e., in the 3D referential image $PI_{ref}$) is shifted to a position $P1_{real}$ (or a position P2 is shifted to a position P2real). In particular, the positions of the line segments $L_{fm}$-$L_{f1}$ and $L_{r1}$-$L_{rn}$ which are set on the plural added tomographic planes $SF_m$-$SF_1$ and $FR_1$-$FR_n$ are set in consideration of the oblique angle θ of each of the X-ray radiation directions $DR_x$. Thus, the shifted position $P1_{real}$ in the case of a smaller oblique angle θ (refer to FIGS. 34(A) and 35(A)) becomes lower in the Z-axis direction than in the case of a larger oblique angle θ (refer to FIGS. 34 (B) and 35(B)). Accordingly, the shifted position $P1_{real}$ can be compensated in distortion depending on the oblique X-ray radiation angle θ, i.e., the largeness of the enlargement factor. Incidentally as shown in FIG. 36, when the tooth is present at and along the 3D referential tomographic plane SS, a relationship of $P1=P1_{real}$ is met. In this case, the 3D referential tomographic plane SS, at and along which it is assumed that the tooth is present, provides a real position, thus providing a shift amount of zero.

The image processor 56 then proceeds to step S65, at which data indicating the real position of the tooth portion is stored every position P(x, y, z) in the work area thereof.

In this way, as to the currently designated position P(x, y, z) on the 3D referential image $PI_{ref}$ (i.e., the 3D referential tomographic plane SS), practically, in this description, the first designed initial position P(0, 0, 0), the specification is performed in the depth direction passing through the initial position P(0, 0, 0). This specification is filtering to check whether or not there is a portion of the tooth (enamel). And when it is checked that there is such a tooth portion, an optimally focused position for the tooth part is specified in the depth direction.

Figure 37:
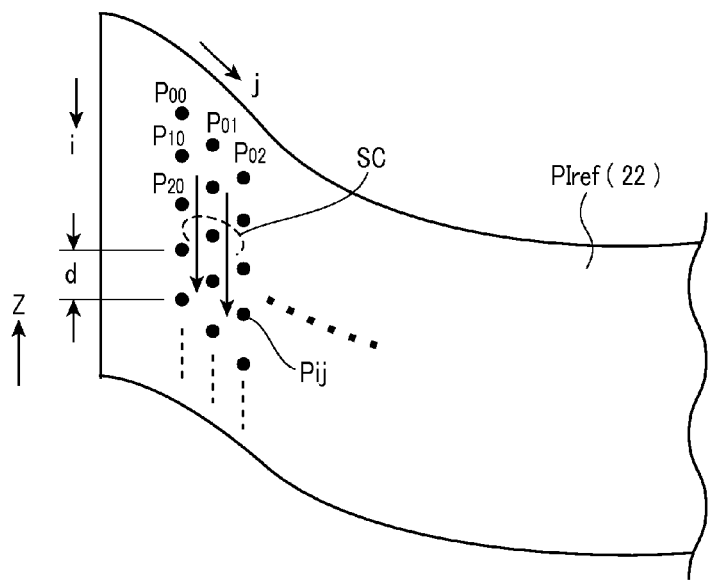
FIG. 37 is a perspective view explaining a process for moving processing points on the 3D reference image in order to perform the position identifying process.

After this, as shown in FIG. 37 for example, the image processor 56 determines whether or not the foregoing specifying steps has been completed at all determination points (sampling points) P previously set on the 3D referential image $PI_{ref}$ (step S67). This determination is executed by checking whether or not the currently processed position P(x, y, z) is the last position P(p, q, r). If this determination is NO which shows the specifying steps have not been competed at all the determination points P, the image processor 56 shifts the determination point P(x, y, z) by one (step S68), before returning to the foregoing step S55 to repeat the foregoing series of specifying steps.

As shown in FIG. 37, the plural determination points P are previously mapped with given intervals on the 3D referential image $PI_{ref}$ (i.e., the 3D referential tomographic plane SS). In the example shown here, along both the vertical direction i and the horizontal direction j of the 3D referential image $PI_{ref}$, the positions P are mapped at the same given intervals d in the vertical and horizontal directions. Alternatively, the internals d may be differentiated between the vertical and horizontal directions i and j from each other. The direction along which the shift is carried out at step S68 may be any of the vertical, horizontal and oblique directions on the 3D referential image $PI_{ref}$. As shown in FIG. 37, the shift can be made along the first vertical direction i, and the line is transferred in the horizontal direction j to repeat the shift in the second vertical direction i. This shifting manner is repeated regularly (refer to a reference numeral SC in the figure). Oppositely to this, the shift can be made along the horizontal direction j, and the line is transferred in the vertical direction i to repeat the shift in the horizontal direction. Moreover, the shift may be performed obliquely.

Meanwhile, when the foregoing specifying steps have completed for all the plural determination points P, the determination at step S67 reveals YES during the repeated processing. This means that, every determination point P, an optimally focused sectional position has been detected in the depth direction passing through the position P on the 3D referential tomographic plane SS (including determination whether or not there is an optimally focused position). In this case, the processing proceeds to a connection process of the optically focused sectional positions.

<Process to Connect Optimally Focused Sectional Positions>

Figure 38:
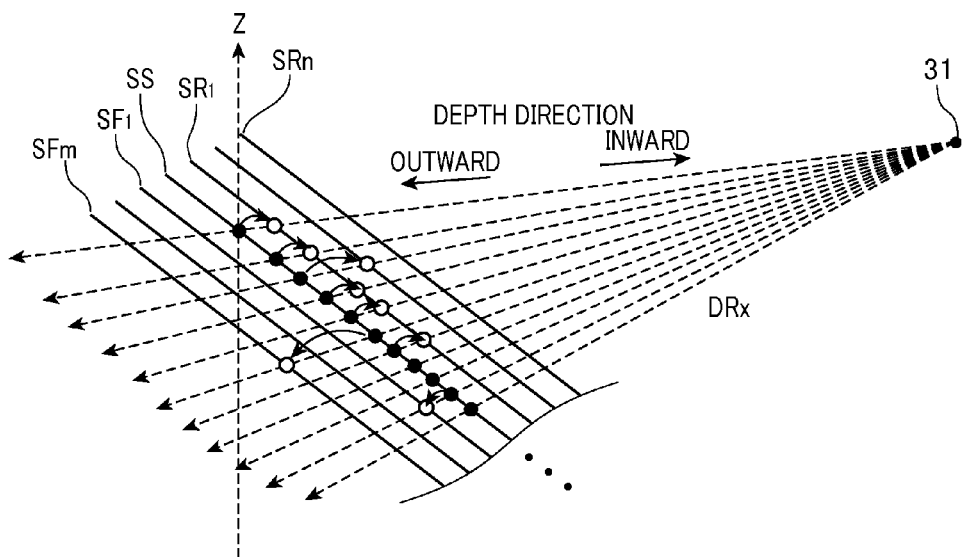
FIG. 38 is a perspective view explaining identification of the position of an optimally focused tomographic plane being identified every processing point and its abnormal identification.

When it is determined YES at the foregoing step S67, the image processor 56 reads data indicative of the optimally focused sectional positions specified and stored at step S65 (step S68). The data of these sectional positions show positions in each of the X-ray radiation directions $DR_x$ passing through each of the determination points P(x, y, z). This is pictorially exemplified in FIG. 38. In this drawing, filled circles indicate determination points P(x, y, z) on the 3D referential image $PI_{ref}$ (i.e., the 3D referential tomographic plane SS). In this case, the vertical and horizontal directions of the curved 3D referential image $PI_{ref}$ are denoted by (i, j). In FIG. 38, as shown by open circles, for example, an optimally focused sectional position at a determination point $P(x_{00}, y_{00}, z_{00})$ for i, j=0, 0 is read as a position actually preset at the position of a tomographic plane SR1, which is shifted inwardly by one section (toward the X-ray tube side). An optimally focused sectional position at a determination point $P(x_{01}, y_{01}, z_{01})$ for i, j=0, 1, which is next to the determination point for i, j=0, 0, is read as a position also actually present at the position of the tomographic plane SR2, which is shifted inwardly by one section. Furthermore, an optimally focused sectional position at a determination point $P(x_{02}, y_{02}, z_{02})$ for i, j=0, 2, which is next to the determination point for i, j=0, 1, is read as a position actually present at the position of a tomographic plane SR3, which is shifted inwardly by a further one section. In FIG. 38, for the sake of an easier understanding the process at step S68, only one position in the Z-axis direction (i.e., the vertical direction) are shown, but, at each of the positions in the Z-axis direction, the process at step S68 is performed.

The image processor 56 then performs removal of noise (i.e., singularities) (step S70). In the example shown in FIG. 38, an optimally focused sectional position at a determination point $P(x03\ y03, z03)$ for i, j=0, 3 is read as a position actually present at the position of a tomographic plane $SF_m$, which is shifted outwardly by no less than m-piece sections (toward the detector side). In such a case, the image processor 56 applies, for example, a threshold checking to a difference between the sectional positions to find out noise, thus regarding it abnormal data. Hence, the data of mutually adjacent sections are for example smoothed to smoothly connect the sections and replaced with a new set of smoothed positional data. Alternatively, data used for the data replacement may be produced by selectively giving priority to sectional data closer to the outside of the detector. Still alternatively, instead of such compensation using the data replacement, abnormal data may simply be removed from data being processed. It is also possible that the abnormal data to be removed include data abnormal in the Z-axis direction.

The image processor 56 then connects the positions with noise removed (that is, the positions showing the enamel) and three-dimensionally smoothens the connected positional data, whereby a surface image tracing the enamel is produced (step S71). Furthermore, the image processor 56 displays the produced surface image, as a 3D autofocus image $PI_{focus}$ which is a three-dimensional panoramic image all portions of which are automatically optimally focused, on the monitor 60 at a desired view angle (step S72).

Figure 39:
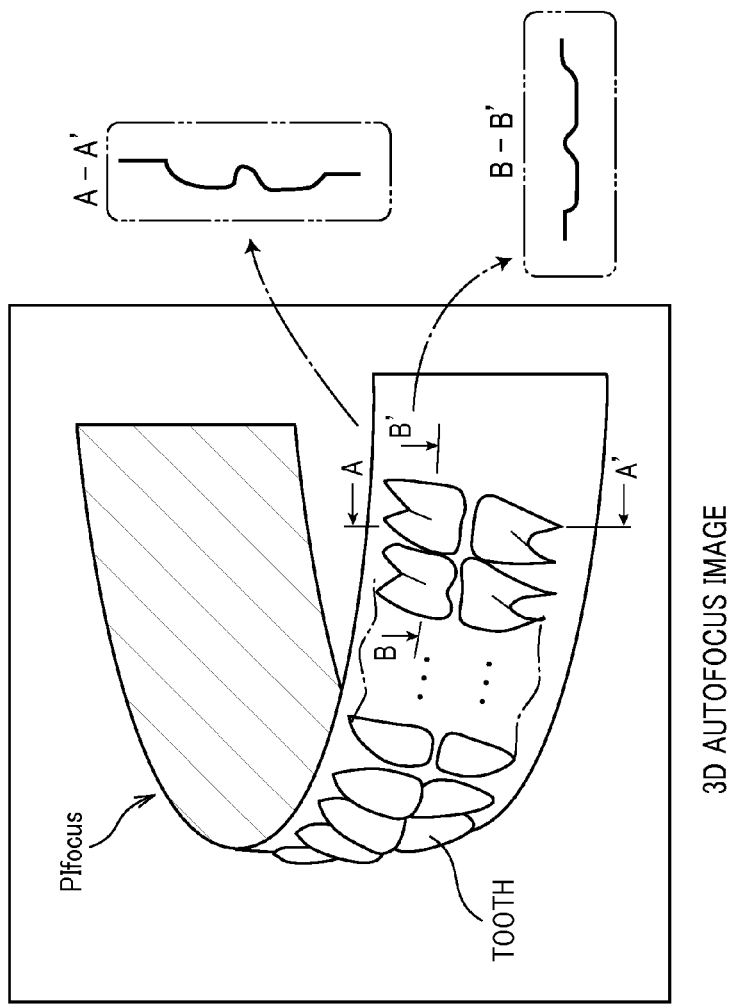
FIG. 39 is a view pictorially showing identification of the position of an optimally focused tomographic plane and a 3D autofocus image produced through smoothing.

Hence, as shown in FIG. 39, it is possible to provide the 3D autofocus image $PI_{focus}$ at the desired view angle, where the 3D autofocus image structurally shows the tooth row of the oral cavity of the object P in the clearest manner. In the drawing, the curved horseshoe-shaped range shows a range to display the 3D autofocus image $PI_{focus}$ and solid lines show the real positions and shapes of the tooth row. As shown by an A-A' line and a B-B' line, portions such as part of the gum (alveolar bone), the mandibular antra, the articulation of jaw, and the carotid artery can be depicted by a tomographic plane produced apart a given distance from the edges of the teeth (mainly the enamel) and the tomographic plane is projected three-dimensionally. In such a case, although it is not guaranteed that such portions other than the teeth are optimally focused, there cannot provide an unnatural feeling to 3D panoramic images. Of course, the calculation for optimal focusing may be improved to optimally focus such portions other than the teeth in the whole calculation, depending on purposes of diagnosis.

In this way, the produced 3D autofocus image $PI_{focus}$ is entirely curved to trace the tooth row and its surface is rough. This "roughness" depicts the real position and shape (contour) of each of the teeth by densities of pixel values. The remaining parts can also be depicted with no unnatural feeling.

Hence, the autofocus image $PI_{focus}$ indicating the real position and shape of the tooth row of each object P.

<Various Display Processes>

The image processor 56 then provides the operator with chances to observe the produced 3D autofocus image $PI_{focus}$ in other modes. Practically, in response to operation information from the operator, the image processor 56 determines whether or not it is desired to display the 3D autofocus image $PI_{focus}$ in other modes, in an interactive manner.

Figure 40:
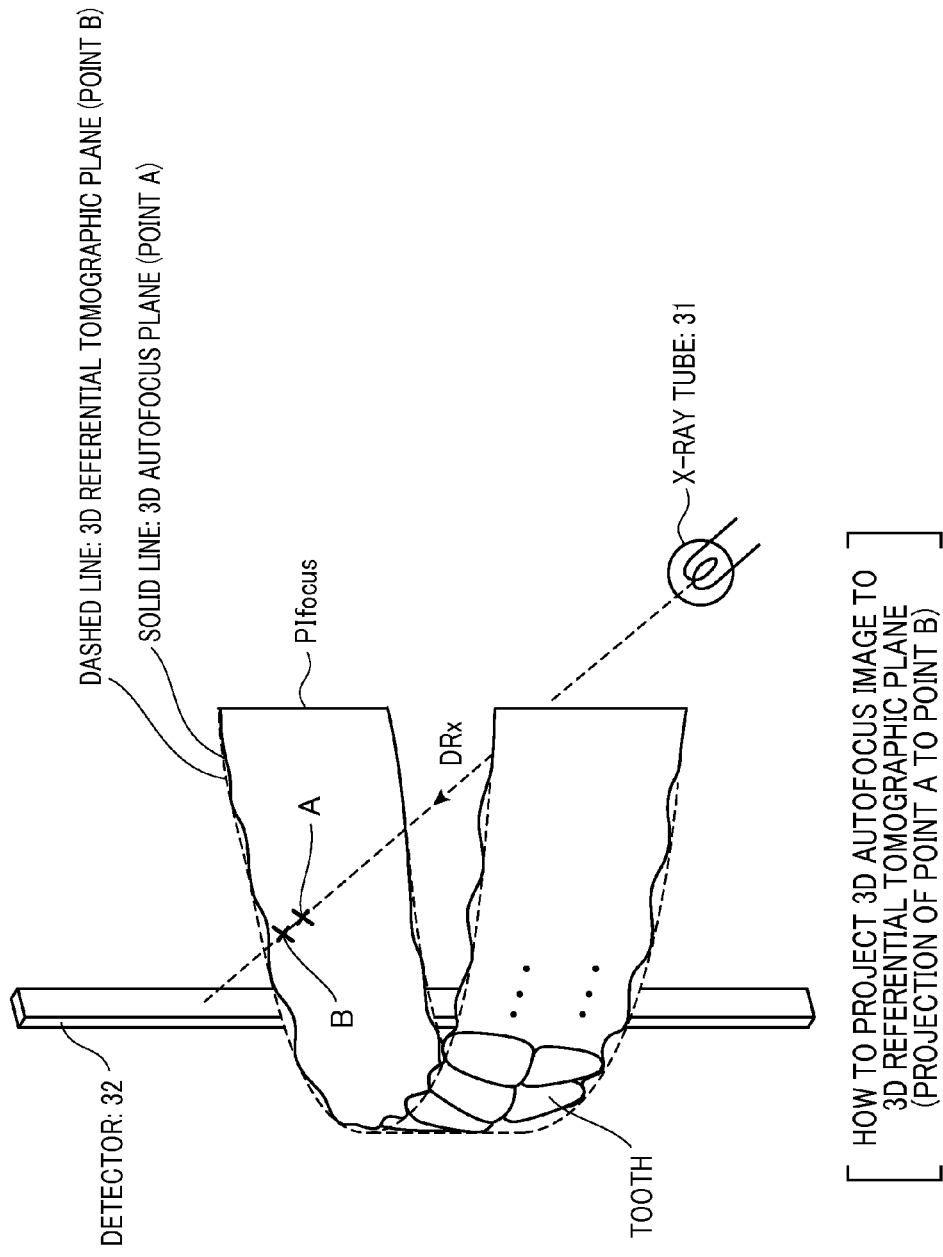
FIG. 40 is a view explaining a concept of processing for projecting the 3D autofocus image onto the 3D referential tomographic plane.

By way of example, the image processor 56 determines whether or not it is desired to observe a partial region of the 3D autofocus image (3D panoramic image) $PI_{focus}$ (in FIG. 5, step S10). When the determination at this step S10 is YES, it is further determined based on information from the operator whether the partial region is desired to be observed using a 3D referential tomographic plane SS or the rectangular plane (two-dimensional) of a referential panoramic image (step S11). When it is determined at this step S11 that the 3D referential tomographic plane SS is used, the image processor 56 re-projects the 3D autofocus image $PI_{focus}$ to the 3D referential tomographic plane SS in the X-ray radiation directions $DR_x$ passing through the pixels of the plane SS respectively (step S12). This re-projection is shown in FIG. 40. This re-projection can be performed by a sub-pixel method, by which each pixel of the 3D referential tomographic plane is sectioned by sub-pixels corresponding to the three-dimensional pixels and then subjected to the re-projection.

A re-projected image to the 3D referential tomographic plane SS is displayed on the monitor 60 as a 3D reference image $PI_{proj-3D}$ (step S13). An example of this 3D reference image $PI_{proj-3D}$ is shown in FIG. 41.

Meanwhile, when it is determined at step S11 that the rectangular plane of the referential panoramic image $PI_{st}$ is desired, the image processor 56 re-projects the 3D autofocus image $PI_{focus}$ to the rectangular plane, that is, the plane of a referential panoramic image (step S14). This re-projection is also performed by the known sub-pixel method, by which each pixel of the plane of the referential panoramic image is sectioned by sub-pixels corresponding to the three-dimensional pixels and then subjected to the re-projection. This re-projection is conceptually shown in FIG. 42. This re-projected image is displayed as a 2D reference image $PI_{proj-2D}$ on the monitor (step S15). An example of this 2D reference image $PI_{proj-2D}$ is shown in FIG. 43.

Figure 41:
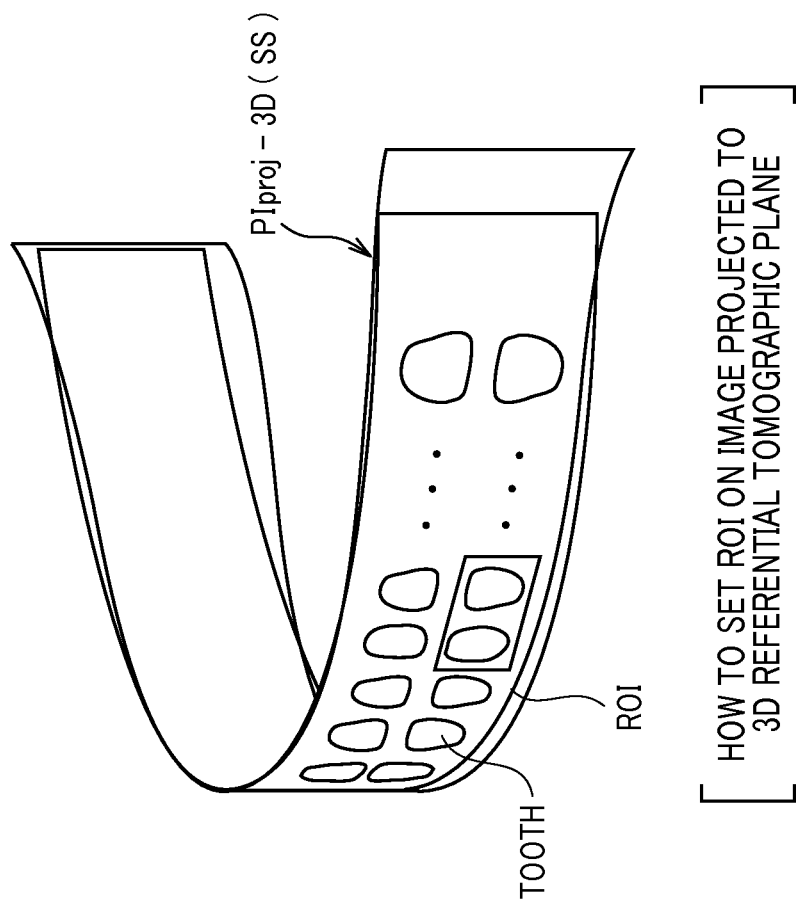
FIG. 41 is a pictorial view explaining an image projected to the 3D referential tomographic plane and a RPI set on the image.
Figure 42:
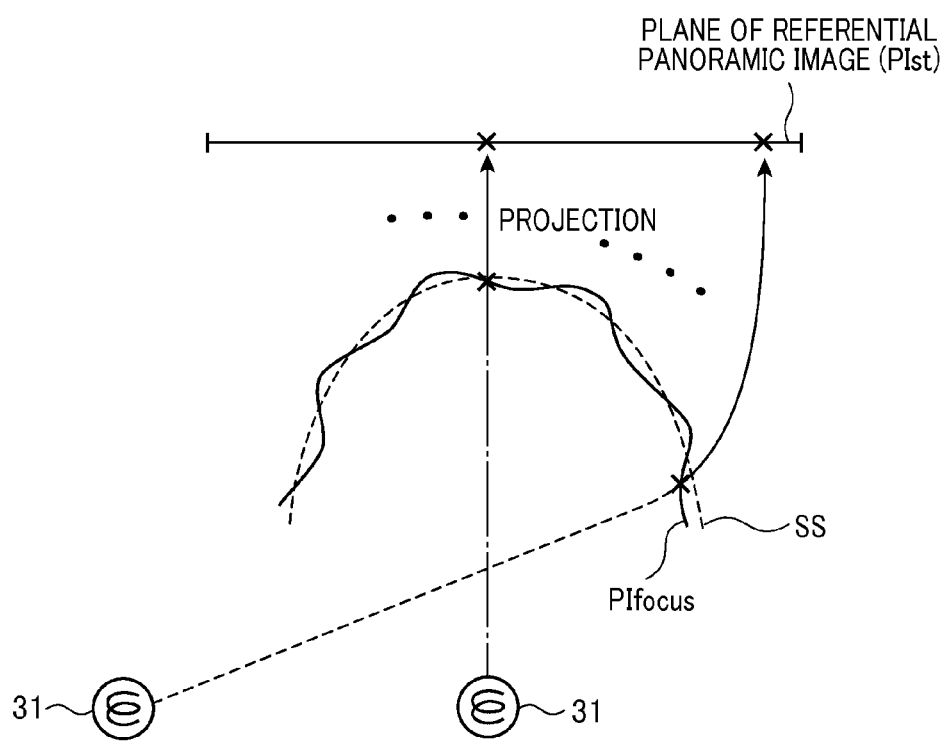
FIG. 42 is a view explaining a concept of processing for projecting the 3D autofocus image to a two-dimensional plane owned by a referential panoramic image.
Figure 43:
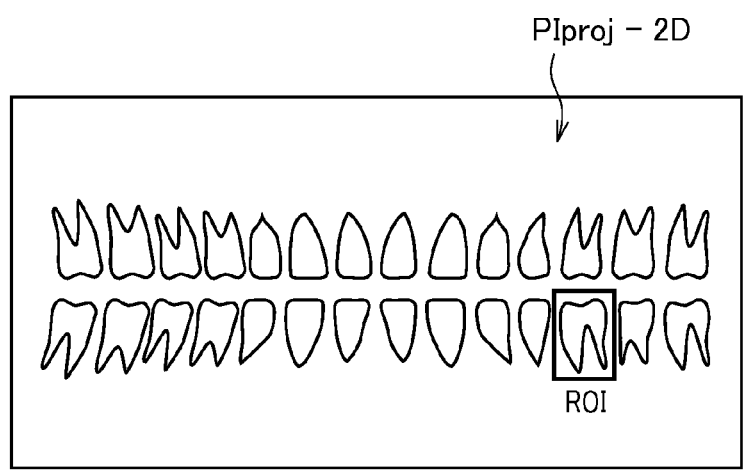
FIG. 43 is a view pictorially explaining a 2D reference image and a ROI which is placed thereon.

The operator sets a desired ROI (region of interest) of, for example, a rectangle on either the 3D reference image $PI_{proj-3D}$ or the 2D reference image $PI_{proj-2D}$ (Step S16; refer to FIGS. 41 and 42). A partial region designated by this ROI is enlarged, and superposed on the currently displayed 3D reference image $PI_{proj\text{-}3D}$ or the 2D reference image $PI_{proj\text{-}2D}$, for example (step S17). Of course, such a re-projected image may be displayed differently from the panoramic image, displayed together with the panoramic image in a divided manner, or displayed using a template consisting of a plurality of display blocks mapped along the tooth row.

The image processor 64 then determines whether or not the foregoing set of processes should be ended, using information from the operator (step S18). When being determined YES, the processing is returned to step S7, while being determined NO, the processing is returned to step S10 for repeating the foregoing processing.

By the way, when it is determined at step S10 that the partial region will not be observed, the image processor 56 further determines interactively whether or not the currently displayed 3D automatic image $PI_{focus}$ is necessary to be rotated, moved, and/or enlarged or reduced for display (step S19). If this determination is YES, the image processor responds to a command to rotate, move, and/or enlarge or reduce the 3D autofocus image $PI_{focus}$, and displays such a processed image (steps S20, S21). Then the processing proceeds to step S81 for repeating the foregoing steps.

Of course, the display modes will not be limited to the foregoing, but can adopt various other modes such as color representation.

When the operator commands to end the foregoing processing, the image processor 64 ends the processing via performance at steps S18 and S7.

Incidentally, after setting at step S16, the processing may skip the display at step S17 to directly proceed to step S19. In such a case, the ROI which has been set may be displayed together with the rotated, moved, and/or enlarged or reduced image at step S21.

As stated above, in the present embodiment, the structure of the panoramic imaging space can be analyzed three-dimensionally, which represents the projection directions three-dimensionally. Hence, as long as a panoramic image is focused, a 3D image produced from the panoramic image is prevented from being blurred and is accurately presented. This makes it possible to display the panoramic image reliably regardless of quality of positioning an object being imaged and to provide the entire images with clearer depiction.

Furthermore, using the phantom according to the present embodiment, the parameters necessary for the structural analysis of the imaging space and the 3D reconstruction of panoramic images can be calibrated. This calibration can be selected between the simplified calibration with the radiation angles θ disregarded from the calibration and the detailed calibration with the radiation angles θ taken into account. Thus, the calibration can be performed easily at appropriate timing depending as need arises, every apparatus, and even after being installed in medical facilities. In addition, the structural analysis and the calibration take into account positional changes $\alpha\theta_1$ in the rotation center RC of the pair of the X-ray tube 31 and the detector 32. The 3D image reconstruction is performed using the parameters in which such positional changes $\alpha\theta_1$ is compensated. Accordingly, since individual differences of the parameters possessed by apparatuses and temporal changes in those parameters are compensated reliably, it is possible to provide three-dimensional surface images which depict the actual position of a teeth row, i.e., which three-dimensionally provide more accurate distances on the surface images.

In addition, even when a trajectory produced by the referential tomographic plane of a panoramic imaging apparatus is unknown, it is possible to measure the constant parameters and the functional parameters, which feature the imaging space, through imaging using the phantom 101.

(Modifications of Phantom)

The phantom adoptable in the radiation imaging apparatus according to the present invention is not limited to the foregoing one, but may be modified into various other configurations.

In the foregoing phantom 101, the outer-plane trajectory $OR_{outer}$ is set which is located outside of the reference-plane trajectory $OR_s$. However, an inner-side path may be set which is located inward by a predetermined distance from the reference-plane trajectory $OR_s$.

Figure 44:
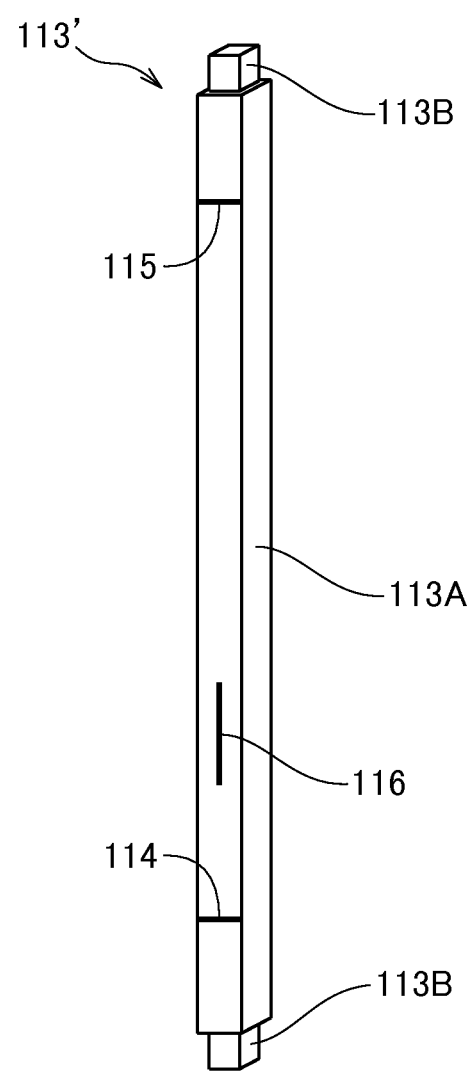
FIG. 44 is an illustration showing a modification of the phantom.

Additionally the phantom 101 is equipped with pillars 113 and 113', which are planted along the different two paths $OR_s$ and $OR_{outer}$, have the same shape and size, whereby productivity of the pillars can be higher, since one of the two sets of pillars can be planted upside down in assembling the phantom. Further, of the pillars 113 and 113' planted the angles other than the X-ray radiation angle θ=0 degrees, one of the two sets of pillars, for example, the pillars 113' planted along the outer-plane trajectory $OR_{outer}$ are just for measurement of the gain $\Delta X/\Delta F_i$ and the X-ray radiation angles θ. Hence the first and second markers 114 and 115 may be removed therefrom. This simplified phantom is exemplified in FIG. 44.

There is provided a modification of the pillars 113 and 113'. In the foregoing embodiment, the pillars are produced as long and rectangular cylinders, but may be long and round bars 201 (refer to (A) of FIG. 45). Alternatively instead of using the pillars 113 and 113', band-shaped suspension members 202 can be used, in which markers are arranged on the suspension members (refer to (B) of FIG. 45).

There are still modifications of the first, second and third markers 114, 115 and 116. Such markers are necessarily not liner, but may be a point-sequence marker which is composed of plural points which form a line (refer to (C) of FIG. 45). In particular, since it is sufficient that the first and second markers 114 and 115 are able to represent positions in the vertical direction, such markers may be composed of a single point-like marker (refer to (D) of FIG. 45). Moreover, the first, second and third markers 114, 115 and 116 can be produced as a single marking member. For example, in the structure shown in FIG. 32, there is provided a thin and long marking plate 203 which connects the first and second markers 114 and 115 in the vertical direction and there is formed a slit S along a portion positionally corresponding to the third marker 116 (refer to (E) of FIG. 45). The upper and lower ends of this marking plate function as the first and second markers and the slit S functions as the third marker 116, so that this marking plate can be affixed at a predetermined position of the pillar 113.

Further, it is sufficient that the markers 114 to 116 differ in the X-ray transmittance from the other portions of the phantoms. Hence, for example, the pillars 113 and 113' may be made of metal and portions positionally corresponding to the markers may be made of materials of which X-ray transmittance differ from the metal (mere recesses is acceptable as the markers, in this case).

In this way, needless to say, there are many variations of structures of the phantom 101 necessary for acquiring information indicative of necessary positions and distances. Instead of using the structures according to the embodiment and modifications thereof, which enable all necessary information to be measured at one time, a plurality of different phantoms may be prepared which are dedicated to acquisition of information specialized to each item. The gist of the present invention includes a set of such specialized plural phantoms. For example, the foregoing universal type phantom 101 may be prepared as a first phantom equipped with a set of pillars 113 planted along the reference-plane trajectory $OR_s$ only and a second phantom equipped with a set of pillars 113' planted along the outer-plane trajectory $OR_{outer}$ (or an inner-plane trajectory, although not shown). In this example, two-time scans are performed for the first and second phantoms and two panoramic images are reconstructed from results obtained by the respective scans, so that the foregoing measurement can be performed.

Furthermore, these first and second phantoms may be produced separately from each other but can be assembled into the one universal type phantom 101. In this configuration, the first and second phantoms themselves are stored separately from each other until measurement, but can be used as one phantom the measurement is performed.

The present invention will not be limited to the foregoing embodiment, and, needless to say, the embodiment can be modified into various types as long as modifications depart from the gist of the present invention. For example, the rotation unit 24 may be structurally modified such that, when the X-ray tube 31 and the detector 32 are driven to rotate (move) around the oral cavity of the patient P, the X-ray tube 31 and the detector 32 are obliquely to each other during which the X-ray beam is scanned. Alternatively, a scan based on this "mutually-oblique opposition" and a further scan based on the "mutually-direct opposition" described in the foregoing embodiment may be combined appropriately with each other. This combination can be selectively applied depending on which portion of the tooth row in a patient's oral cavity is scanned. This makes it possible to enable the X-ray beam to, as much as possible, perpendicularly pass through each portion of the tooth row at any time, whereby the X-ray beam can be radiated at angles where overlaps of teeth and/or undesired imaging of the cervical spine are prevented as much as possible. Accordingly, it is possible to reconstruct panoramic images with fewer artifacts.

By the way, the radiation imaging apparatus according to the present invention is not restricted to dental panoramic imaging apparatuses, but can be produced as apparatuses which three-dimensionally examine actual shapes (positions) of an object using the tomosynthesis method. Such applications include, as medical modalities, a mammography apparatus and a scanner for examining lung cancer, which are based on this tomosynthesis method.

INDUSTRIAL APPLICABILITY

According to the present invention, for imaging, measurement of the phantom makes it possible to easily and accurately analyze and calibrate parameters structurally defining the imaging space, which parameters concern with positions, distances, and angles of the X-ray tube, the 3D referential tomographic plane, and the detector. It is therefore possible to provide a radiation-based imaging apparatus which is capable of three-dimensionally imaging objects at higher accuracy.

DESCRIPTION OF REFERENCE NUMBERS

1 Dental panoramic imaging apparatus (radiation imaging apparatus)
12 Computer
14 Imaging unit
31 X-ray tube (radiation source)
32 Detector
33 Collimator
41 High-voltage generator
53 Buffer memory
54 Image memory
55 Frame memory
56 Image processor
57 Controller
58 Operation device
60 Monitor
101 Phantom
111 Base
113, 113' Support pillar member
114 to 116 Phantom

What is claimed is:

1. A radiation imaging apparatus comprising:
a radiation source that radiates X-rays;
a detector that is arranged to be opposed to the radiation source and that outputs, frame by frame, a frame of digital electric two-dimensional data corresponding to the X-rays entering the detector;
rotating means for relatively rotating the radiation source and the detector to the object, such that an object being imaged is located between the radiation source and the detector and a predetermined fixed point on a virtual line connecting the radiation source and the detector at each rotation angle is positionally changed to the object during the rotation in an imaging space provided between the radiation source and the detector;
data acquiring means for acquiring, frame by frame, the data outputted from the detector while the radiation source and the detector, the detector, or the object is moved by the rotating means,
the data acquired being produced into a three-dimensional image of an imaging portion of the object;
a phantom arranged in the imaging space to be located at predetermined tomographic planes in the imaging space and configured to have markers with which known positional information in the imaging space is imaged with the X-rays;
image producing means for producing, based on a tomosynthesis technique, an image from the data acquired by the data acquiring means in response to the X-rays emitted from the radiation source in a state where the phantom is arranged in the imaging space;
first calculating means for calculating, based on the known positional information of the markers and information indicative of positions of the markers obtained from the image, information indicative of a distance between the radiation source and the detector and information indicative of a height of the radiation source relative to the detector; and
second calculating means for calculating, based on results calculated by the first calculation means and the data, a parameter defining a positional relationship among the radiation source, the detector, and the tomographic planes in the imaging space by taking into account positional changes of the fixed point on the virtual line to the object when the radiation source and the detector are relatively rotated around the object.

2. The radiation imaging apparatus of claim 1, wherein
the radiation source is an X-ray tube that radiates an X-ray as the X-rays,
the detector is a detector that detects the X-rays,
the rotating means rotates the pair of the radiation source and the detector around the object along orbits having mutually different curvature factors and at angular velocities, the orbits including circular orbits or ellipsoidal orbits, and rotates the pair such that the X-ray tube and the detector are always directly opposed to each other, and the image producing means produces a panoramic image, as the image, by applying the tomosynthesis technique to the data acquired by the data acquiring means.

3. The radiation imaging apparatus of claim 2, wherein the orbits are circular orbits, and
the amount of the rotational changes of the rotation center is provided when the radiation source and the detector rotate along the mutually different circular orbits with the rotation center used in common by the circular orbits.

4. The radiation imaging apparatus of claim 3, wherein the first calculating means is configured as means for calculating, as the information indicative of the distance, a first distance between the X-ray tube and the rotation center and a second distance between the rotation center and the detector, and, as the information indicative of the height, a height of the height of the X-ray tube with reference to a reference position of the detector in a direction of the height.

5. The radiation imaging apparatus of claim 4, wherein the second calculating means is configured as means for calculating, as the parameter, a rate of changes between a movement distance of a detection surface of the detector and frame numbers of the data, a projection angle of an X-ray flux radiated from the X-ray tube to the object, a rate of changes between the projection angle and the frame numbers, a third distance from the rotation center to the imaging portion, an amount of positional changes in the rotation center, and coordinate positions of the rotation center, which are all functions of which inputs are the frame numbers of the data.

6. The radiation imaging apparatus of claim 1, wherein the predetermined fixed point on the virtual line is a physical rotation center around which the radiation source and the detector are rotated by the rotating means with the object positioned therebetween, and
the parameter includes a gain with which the frame data are shifted from each other and pixel values of the shifted frames are added pixel by pixel to each other in the tomosynthesis technique.

7. The radiation imaging apparatus of claim 6, wherein the apparatus comprises storage means configured to store, as calibration data, the parameter calculated by the second calculating means.

8. The radiation imaging apparatus of claim 7, wherein the apparatus comprises third calculating means for reading the calibration data from the storage means and three-dimensionally calculating an actual position of the imaging portion based on the read calibration data, when the imaging portion of the object is imaged by the X-rays.

9. The radiation imaging apparatus of claim 6, wherein the second calculating means calculates the parameter by taking into account an amount of movement of the rotation center on the virtual line, the amount of the movement serving as the positional changes.

10. The radiation imaging apparatus of claim 9, wherein the rotating means is configured to rotate the pair of the radiation source and the detector around the object along orbits having mutually different curvature factors and at angular velocities, the orbits including circular orbits or ellipsoidal orbits.

11. The radiation imaging apparatus of claim 6, wherein the phantom is equipped with a base,
a plurality of pillars planted, trajectory by trajectory, at positions on each of a reference-plane trajectory and a further trajectory which is set to be separated from the reference-plane trajectory but runs parallel with the reference-plane trajectory, the reference-plane trajectory being produced by a referential tomographic plane to the base, the referential tomographic plane being set as a tomographic plane in the imaging space, and
the markers are arranged at each of the plurality of pillars and formed to be different in an X-ray transmittance from the pillars themselves.

12. The radiation imaging apparatus of claim 11, wherein the pillars of the phantom are planted, trajectory by trajectory, at the positions on each of the reference-plane trajectory and the further trajectory which is set to be separated from the reference-plane trajectory but runs parallel with the reference-plane trajectory, the reference-plane trajectory being produced by projecting an approximately horseshoe-shaped referential tomographic plane to the base, the referential tomographic plane following a tooth row which is the imaging portion, the further trajectory being approximately horseshoe-shaped.

13. The radiation imaging apparatus of claim 11, wherein the markers include first markers located at the positions on each of the reference-plane trajectory and the further trajectory in order to obtain information showing a first distance between the X-ray tube and the rotation center, a second distance between the rotation center and the detector, the height, and a third distance from the rotation center to the imaging portion at a reference angle among predetermined radiation angles of the X-ray beams and measure an enlargement factor in a height direction in an image, the reference angle not being given changes in the position of the rotation center by the X-ray radiation angles.

14. The radiation imaging apparatus of claim 13, wherein the markers include second markers located at the positions on either the reference-plane trajectory or the further trajectory in order to obtain information showing the third distance and measure the enlargement factor in the height direction in the image at the radiation angles other than the reference angle.

15. The radiation imaging apparatus of claim 14, wherein the markers further include third markers located at the positions on the reference-plane trajectory and the further trajectory at every predetermined rotation angle of the X-ray beam in order to obtain information showing actual values of the projection angles.

16. The radiation imaging apparatus of claim 14, wherein the first and second markers are provided as markers that provide positional information at known two points in a height direction,
the third markers are composed as linear markers or markers providing lines, the third markers being located along the height direction and are mutually different in positions in the height direction between the reference-plane trajectory and the further trajectory.

17. The radiation imaging apparatus of claim 13, wherein the first calculating means comprises
first change rate calculating means configured to calculate, from the image, at the reference angle of the X-ray radiation, the rate of changes between the movement distance of the detection surface of the detector and the frame numbers of the data, and the rate of changes between the projection angle of the X-ray flux radiated from the X-ray source to the object and the frame numbers, which are all functions of which inputs are the frame numbers of the data, and
first information calculating means configured to calculate the first distance, the second distance, and the height based on results calculated by the first change rate calculating means and the enlargement factor of the first markers.

18. The radiation imaging apparatus of claim 17, wherein the second calculating means comprises angle calculating means configured to calculate, at every value of the predetermined radiation angles, actual values of the radiation angles of the X-ray beam based on information of the third markers imaged in the image, second change rate calculating means configured to calculate the rate of changes between the movement distance of the detection surface of the detector and the frame numbers of the data and the rate of changes between the projection angles of the X-ray flux radiated from the X-ray source to the object and the frame numbers, at each of the actual values of the radiation angles of the X-ray beam, and second information calculating means configured to calculate, based on results calculated by the second change rate calculating means and the enlargement factor of the second markers, every one of the actual values of the radiation angles of the X-ray beam, the third distance from the rotation center to the imaging portion, an amount of positional changes of the rotation center, and the coordinate position of the rotation center.

19. The radiation imaging apparatus of claim 18, wherein the apparatus comprises a third calculating means, the third calculating means comprising tomographic plane setting means configured to set a plurality of tomographic planes which are positionally different from the referential tomographic plane in consideration with the first distance, the second distance, the rate of changes of the projection angles to the frame numbers, the third distance, and the amount of positional changes of the rotation center, reconstructing means configured to use data of the images to reconstruct an image of each of the plurality of tomographic planes set by the tomographic plane setting means, and identifying means configured to three-dimensionally identify actual positions showing the imaging portion using the reconstructed plural images, along a direction viewing the X-ray source, based on the actual values of the radiation angles and the coordinate positions of the rotation center.

20. The radiation imaging apparatus of claim 17, the second calculating means comprises second change rate calculating means configured to calculate the rate of changes between the movement distance of the detection surface of the detector and the frame numbers of the data and the rate of changes between the projection angles of the X-ray flux radiated from the X-ray source to the object and the frame numbers, at each of the predetermined radiation angles of the X-ray beam, and second information calculating means configured to calculate, based on results calculated by the second change rate calculating means and the enlargement factor of the second markers, every one of the actual values of the radiation angles of the X-ray beam, the third distance from the rotation center to the imaging portion, an amount of positional changes of the rotation center, and the coordinate position of the rotation center.

\* \* \* \* \*